US009962700B2

(12) United States Patent
Saiki

(10) Patent No.: US 9,962,700 B2
(45) Date of Patent: May 8, 2018

(54) ANALYZING DEVICE

(71) Applicant: Panasonic Healthcare Co., Ltd., Toon-shi, Ehime (JP)

(72) Inventor: Hiroshi Saiki, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 29 days.

(21) Appl. No.: 14/692,315

(22) Filed: Apr. 21, 2015

(65) Prior Publication Data

US 2015/0251183 A1    Sep. 10, 2015

Related U.S. Application Data

(62) Division of application No. 13/001,507, filed as application No. PCT/JP2009/003007 on Jun. 30, 2009, now Pat. No. 9,046,503.

(30) Foreign Application Priority Data

Jul. 17, 2008   (JP) .................. 2008-185445
Jul. 31, 2008   (JP) .................. 2008-197121
        (Continued)

(51) Int. Cl.
    *B01L 3/00*      (2006.01)
    *G01N 1/10*      (2006.01)
        (Continued)

(52) U.S. Cl.
    CPC ..... *B01L 3/502753* (2013.01); *B01L 3/50273* (2013.01); *B01L 3/502715* (2013.01);
        (Continued)

(58) Field of Classification Search
    USPC .................. 422/500–504, 506, 507; 436/180
    See application file for complete search history.

(56) References Cited

U.S. PATENT DOCUMENTS

| 4,557,600 A | 12/1985 | Klose et al. |
| 4,883,763 A | 11/1989 | Nolen et al. |

(Continued)

FOREIGN PATENT DOCUMENTS

| CN | 1613542 | 5/2005 |
| CN | 1618020 | 5/2005 |

(Continued)

OTHER PUBLICATIONS

International Search Report, dated Sep. 29, 2009; PCT/JP2009/003007.

(Continued)

*Primary Examiner* — Dean Kwak
(74) *Attorney, Agent, or Firm* — Hamre, Schumann, Mueller & Larson, P.C.

(57) ABSTRACT

An analyzing device includes: an operation cavity that is adjacent to a first reserving cavity retaining a sample liquid, in a circumferential direction of rotational driving; a connecting section provided on a side wall of the first reserving cavity to suck the sample liquid by a capillary force and transfer the sample liquid to the operation cavity; and second reserving cavities that are disposed outside the operation cavity in the circumferential direction of the rotational driving and communicate with the outermost position of the operation cavity through a connecting passage. The connecting section is circumferentially extended farther than the liquid level of the sample liquid retained in the first reserving cavity.

5 Claims, 56 Drawing Sheets

(30) Foreign Application Priority Data

Nov. 19, 2008 (JP) .................................. 2008-295003
Dec. 24, 2008 (JP) .................................. 2008-326739

(51) Int. Cl.
*G01N 35/00* (2006.01)
*G01N 35/04* (2006.01)

(52) U.S. Cl.
CPC ............................. *G01N 35/00069* (2013.01);
*B01L 2200/0605* (2013.01); *B01L 2200/0621*
(2013.01); *B01L 2200/0652* (2013.01); *B01L
2300/0803* (2013.01); *B01L 2300/087*
(2013.01); *B01L 2300/0867* (2013.01); *B01L
2400/0406* (2013.01); *B01L 2400/0409*
(2013.01); *B01L 2400/0457* (2013.01); *G01N
2035/0449* (2013.01); *Y10T 436/25375*
(2015.01)

(56) References Cited

U.S. PATENT DOCUMENTS

| | | | |
|---|---|---|---|
| 5,472,603 | A | 12/1995 | Schembri |
| 6,235,531 | B1 * | 5/2001 | Kopf-Sill .......... B01L 3/502738 422/549 |
| 7,238,269 | B2 | 7/2007 | Gason et al. |
| 7,384,561 | B2 | 6/2008 | Utsunomiya |
| 7,727,472 | B2 | 6/2010 | Nagaoka et al. |
| 7,749,442 | B2 | 7/2010 | Koike et al. |
| 8,172,455 | B2 | 5/2012 | Noda |
| 8,512,638 | B2 * | 8/2013 | Saiki ................ B01L 3/502715 422/209 |
| 2002/0151078 | A1 | 10/2002 | Kellogg et al. |
| 2006/0153735 | A1 * | 7/2006 | Nagaoka ............. G01N 21/07 422/547 |
| 2007/0003433 | A1 * | 1/2007 | Horike ............. B01L 3/502753 422/533 |
| 2007/0262034 | A1 | 11/2007 | Ducree et al. |
| 2008/0000833 | A1 | 1/2008 | Peters et al. |
| 2009/0246082 | A1 * | 10/2009 | Saiki ................... B01L 3/50273 422/72 |
| 2009/0317896 | A1 * | 12/2009 | Yoo .................. B01L 3/502738 435/287.1 |

FOREIGN PATENT DOCUMENTS

| | | |
|---|---|---|
| CN | 1800858 | 7/2006 |
| JP | 10-501340 | 2/1998 |
| JP | 2005-345160 | 12/2005 |
| JP | 2006-010529 | 1/2006 |
| JP | 2006-145451 | 6/2006 |
| JP | 2006-208183 | 8/2006 |
| JP | 2007-10435 | 1/2007 |
| JP | 2007-033225 | 2/2007 |
| JP | 2007-078676 | 3/2007 |
| JP | 2007-078786 | 3/2007 |
| JP | 2007-093384 | 4/2007 |
| JP | 2007-232673 | 9/2007 |
| JP | 2007-527517 | 9/2007 |
| JP | 2007-330857 | 12/2007 |
| WO | WO 95/033986 | 12/1995 |
| WO | WO 2007/049534 | 5/2007 |
| WO | 2008/053743 A1 | 5/2008 |

OTHER PUBLICATIONS

Japanese Office Action, dated Apr. 16, 2013; Japanese Application No. 2008-85445.
Japanese Office Action, dated Aug. 20, 2013; Japanese Application No. 2008-326739.
Chinese Office Action, dated Aug. 20, 2013; Chinese Application No. 20120464877.7.
Chinese Office Action, dated Aug. 30, 2014; Chinese Application No. 201310470674.3.
Extended European Search Report issued in counterpart European Patent Application No. 09797662.5 dated Sep. 23, 2015 (16 pages).

* cited by examiner

FIG. 1
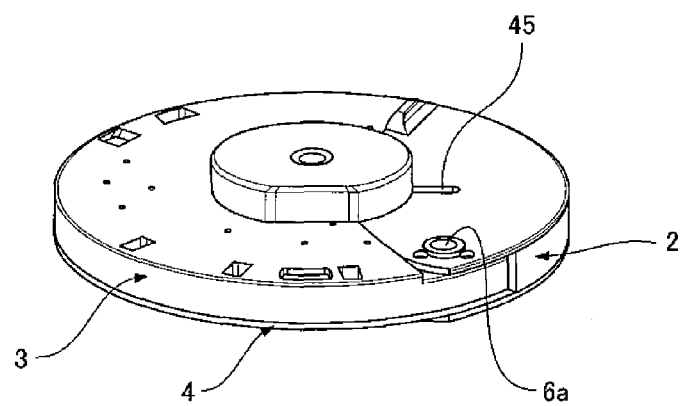
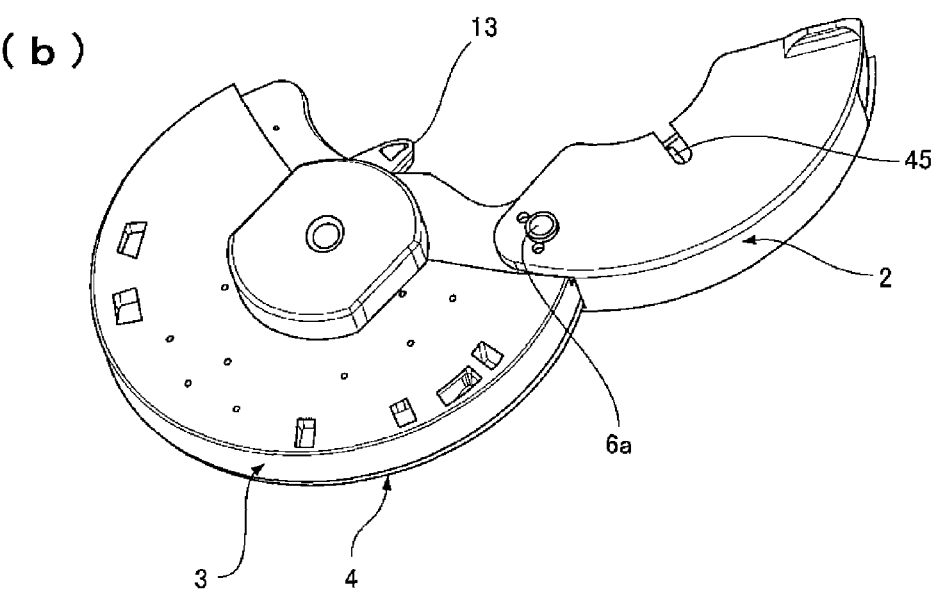

F I G. 2
(a)
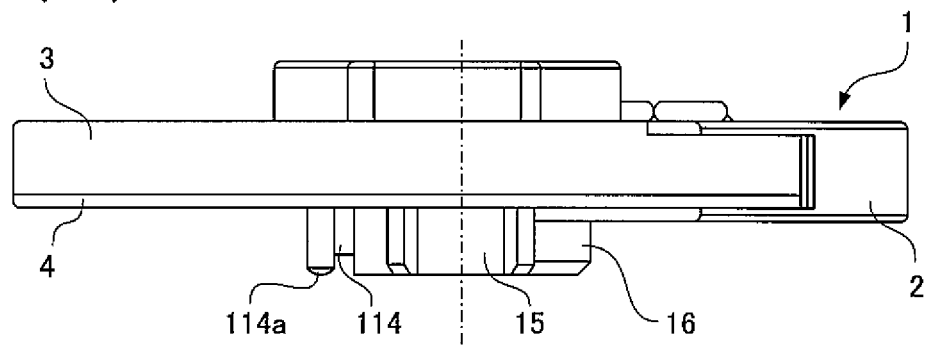
(b)
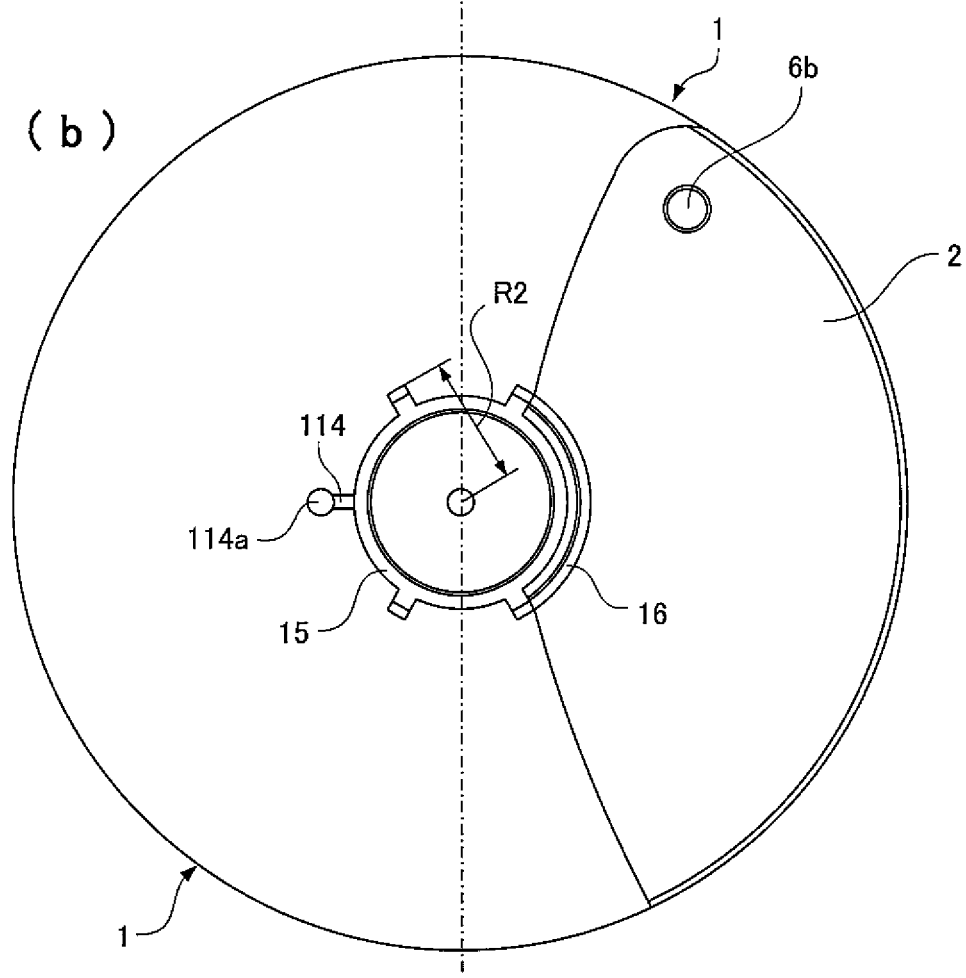

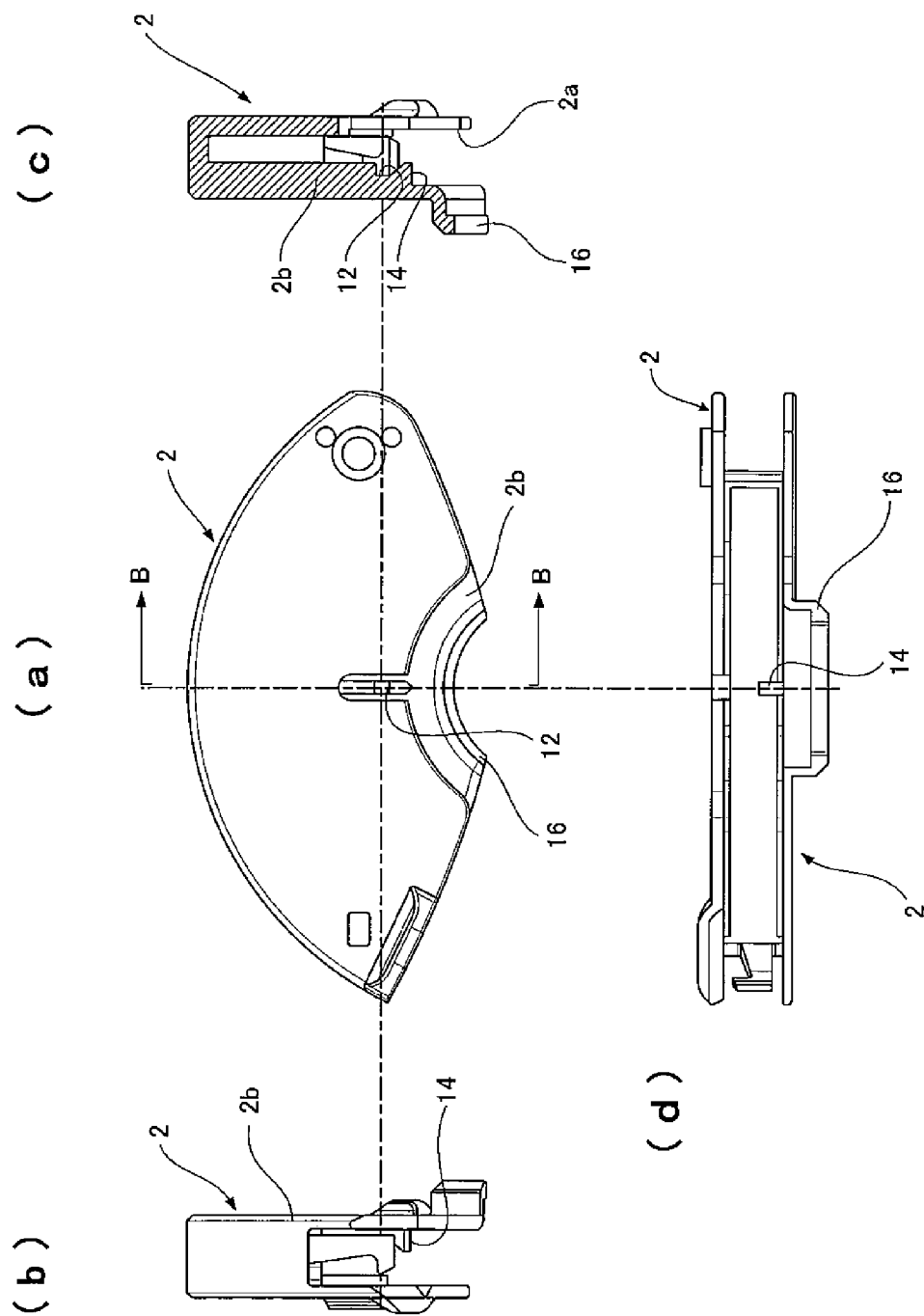

F I G. 1 2
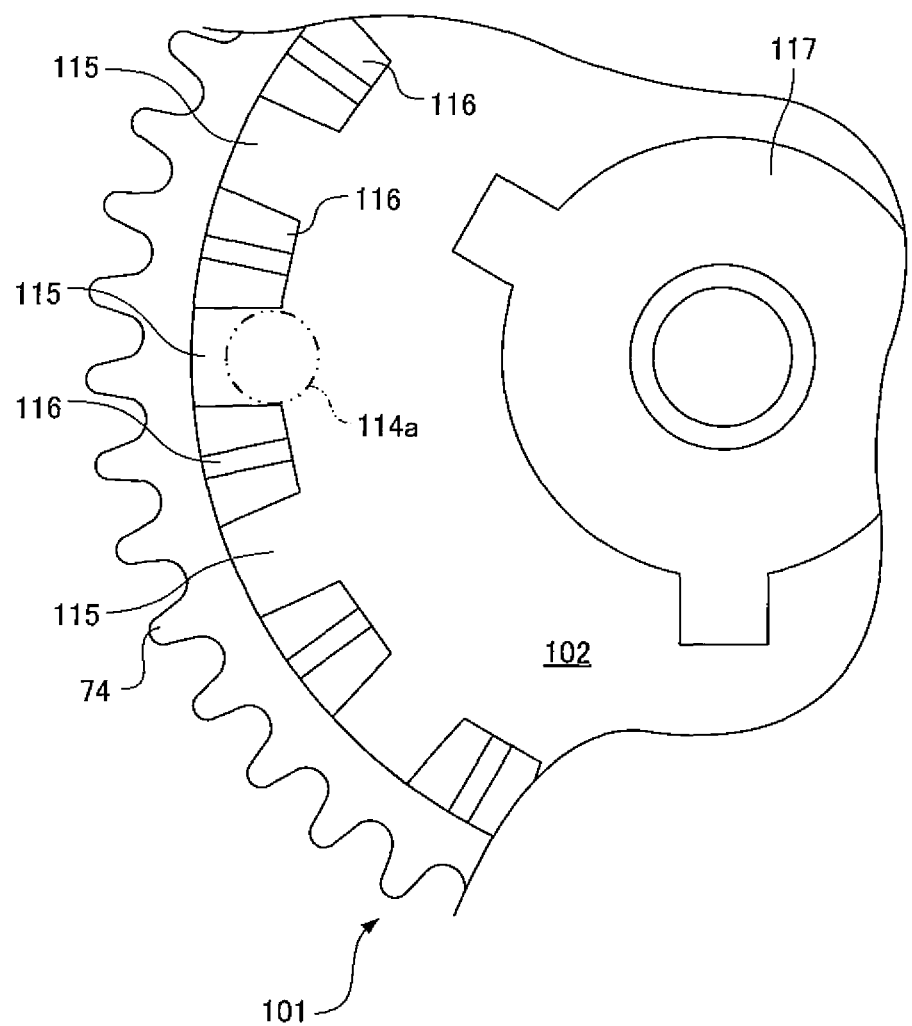

FIG. 16
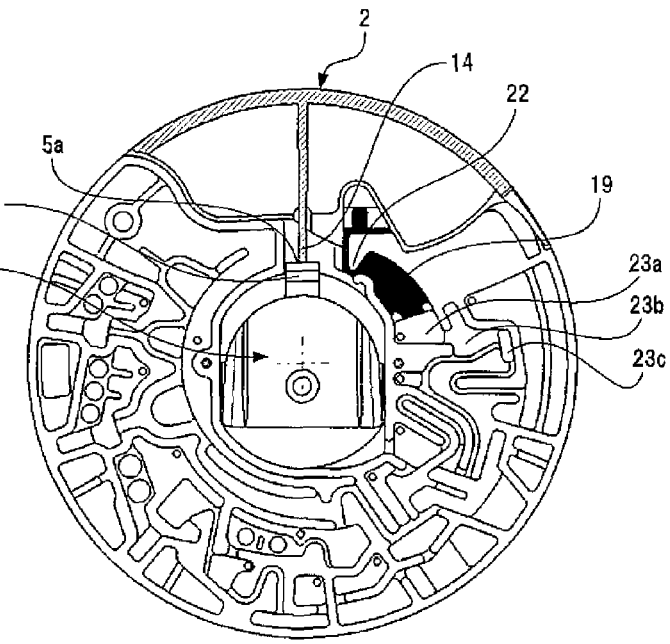
(a)
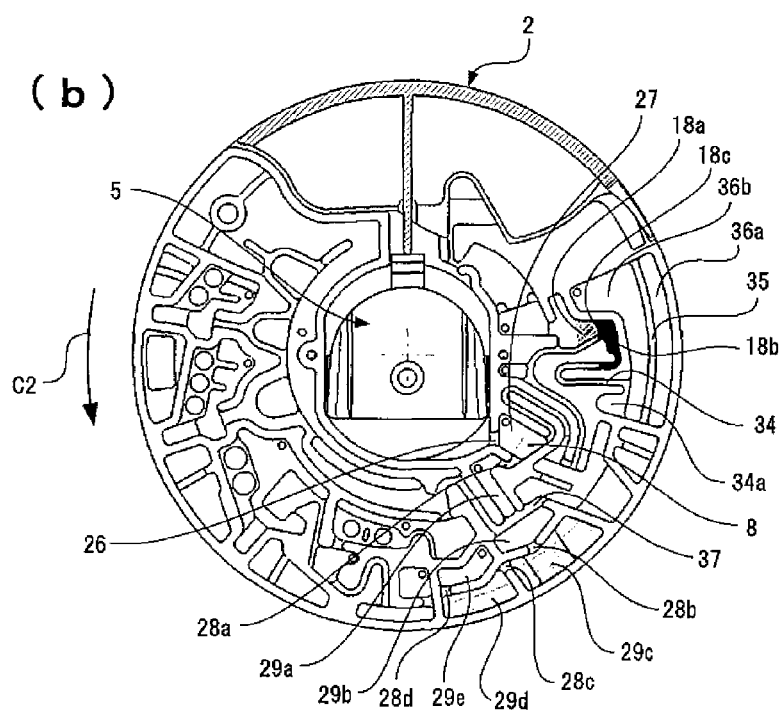
(b)

FIG. 18
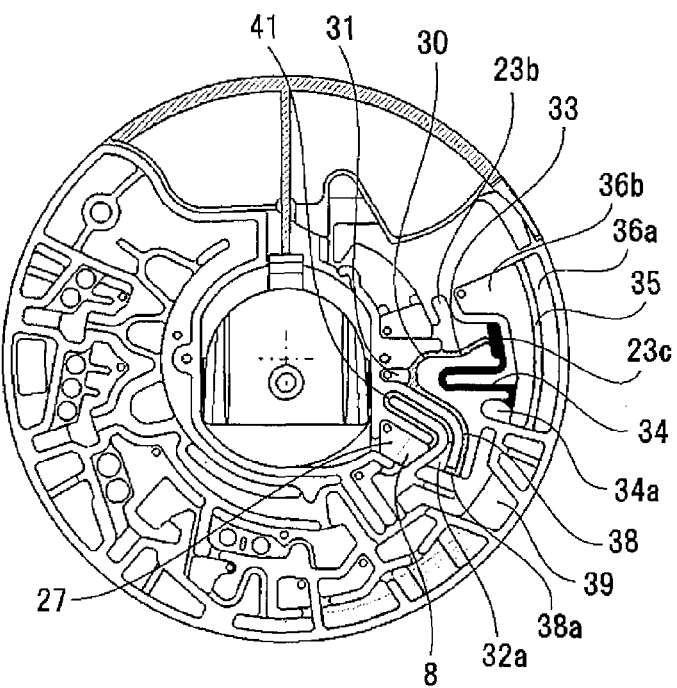
(a)
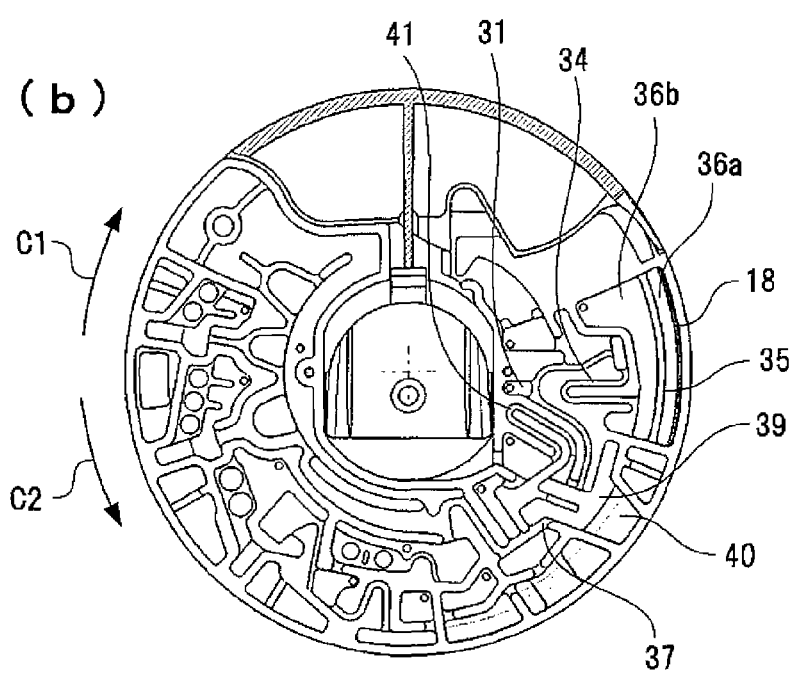
(b)

FIG. 19
(a)
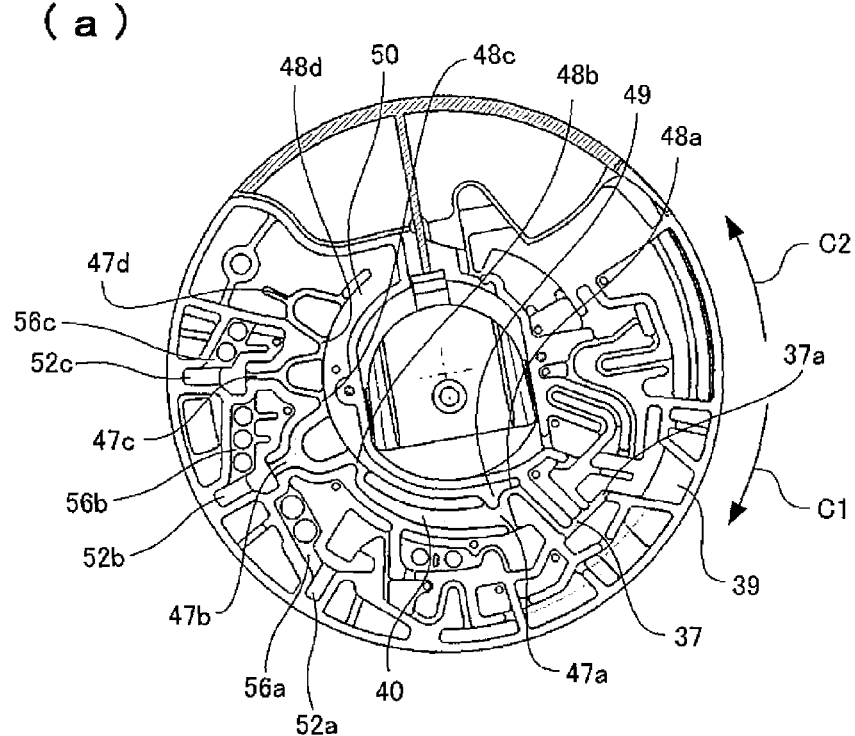
(b)
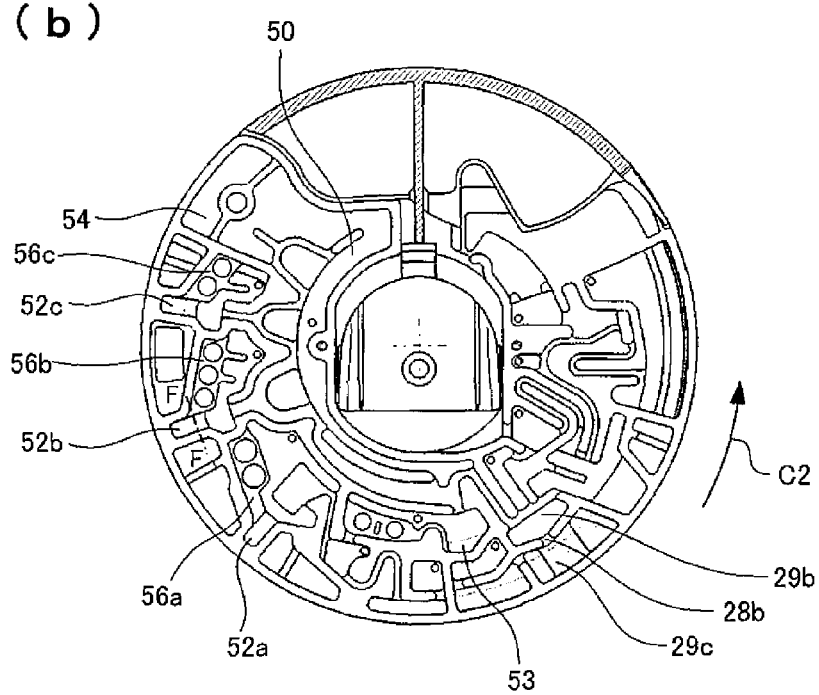

FIG. 20
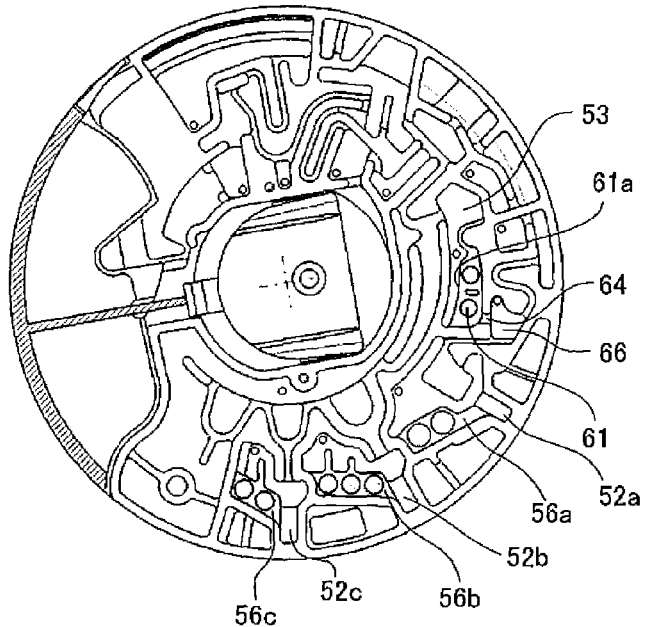
(a)
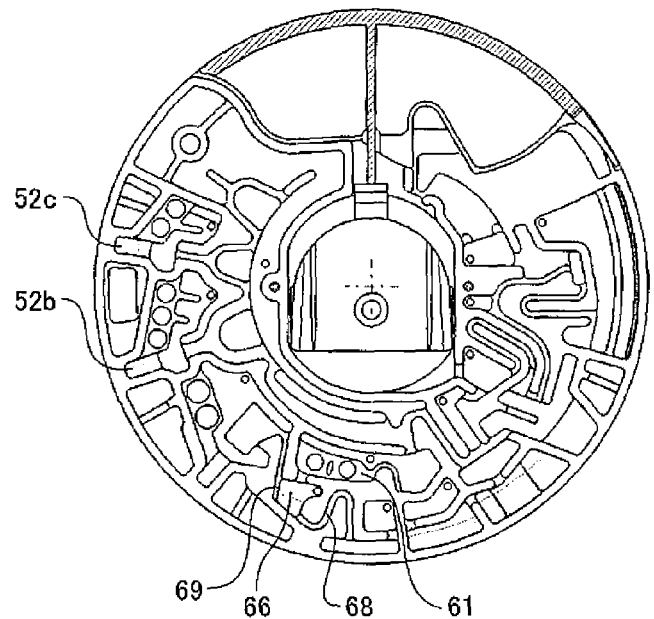
(b)

FIG. 21
(a)
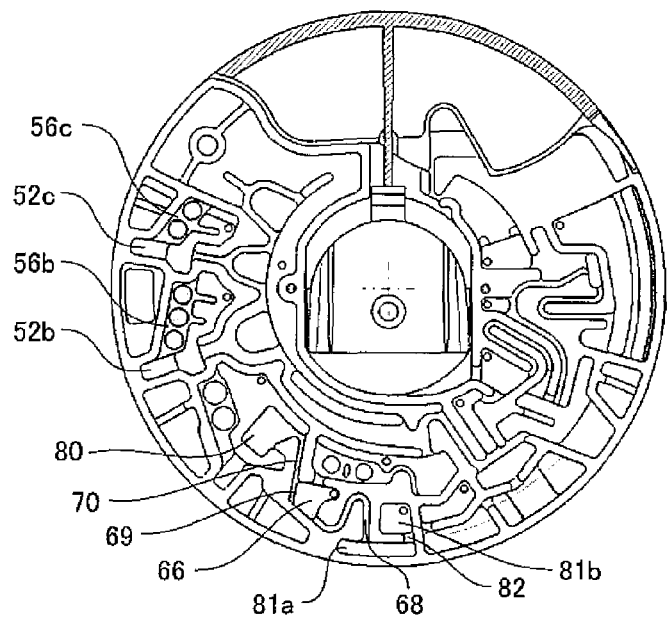
(b)
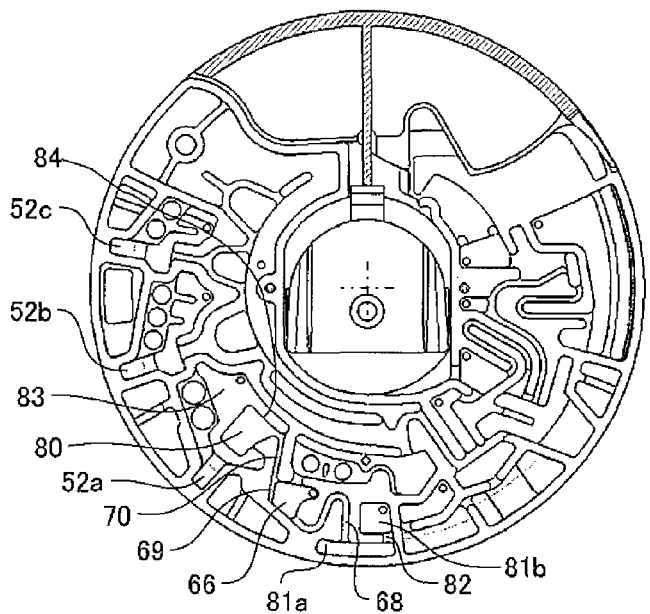

FIG. 22
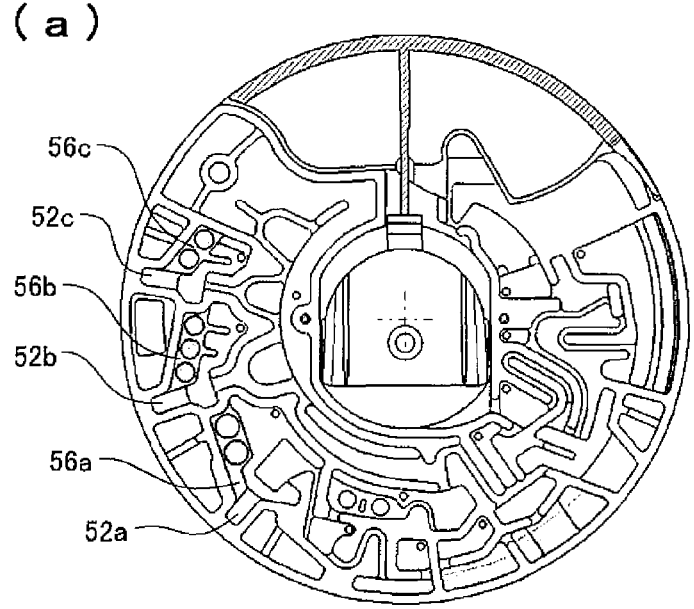
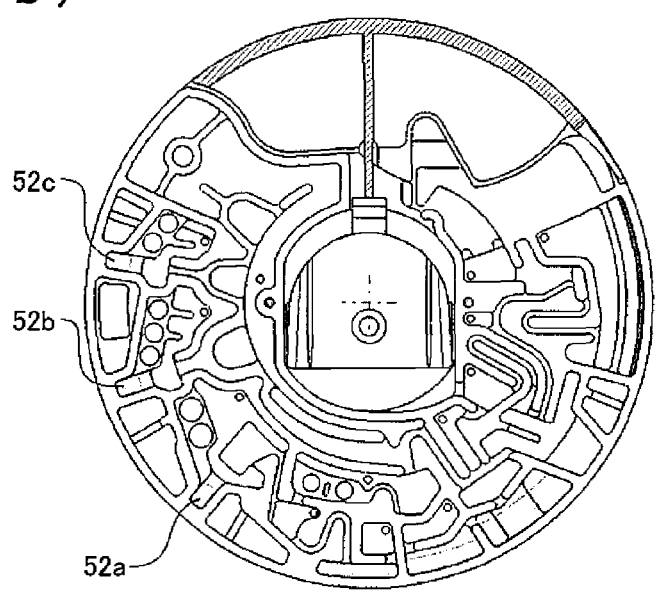

FIG. 23
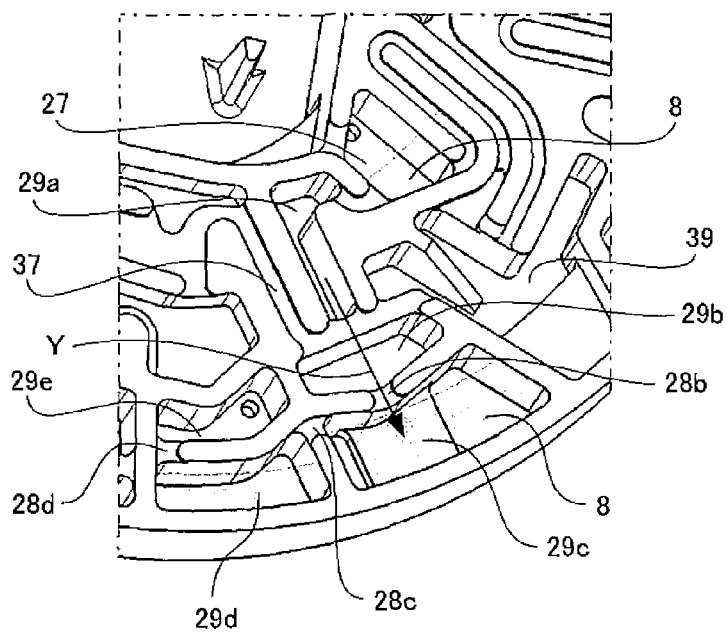
(a)
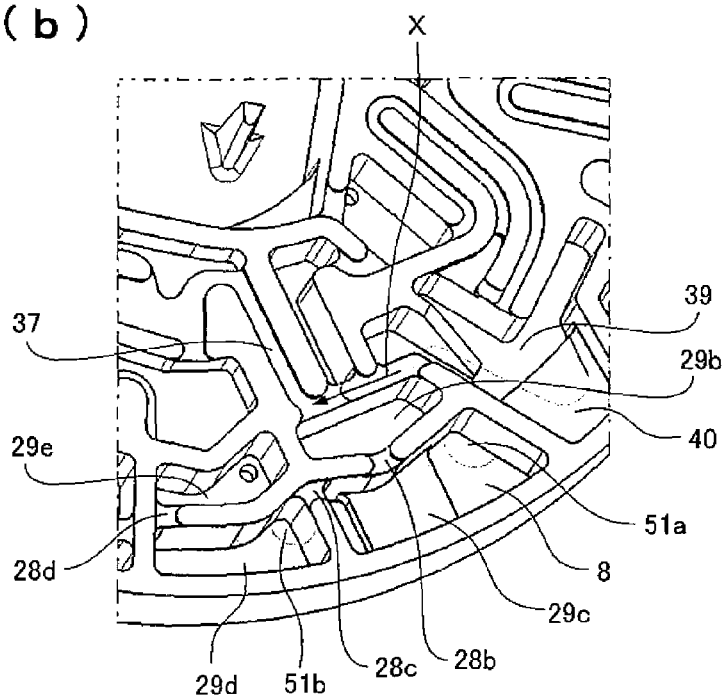
(b)

FIG. 24
(a)
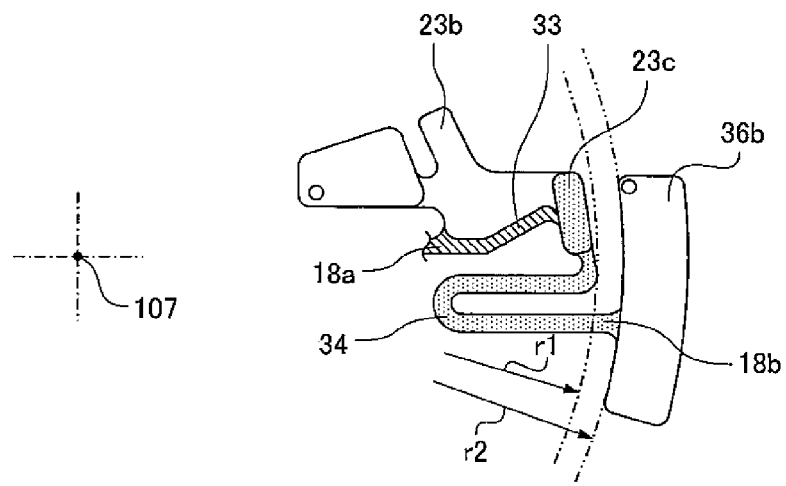
(b)
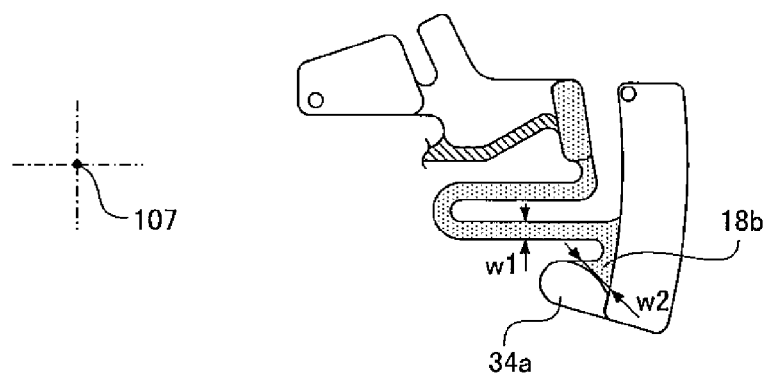
(c)
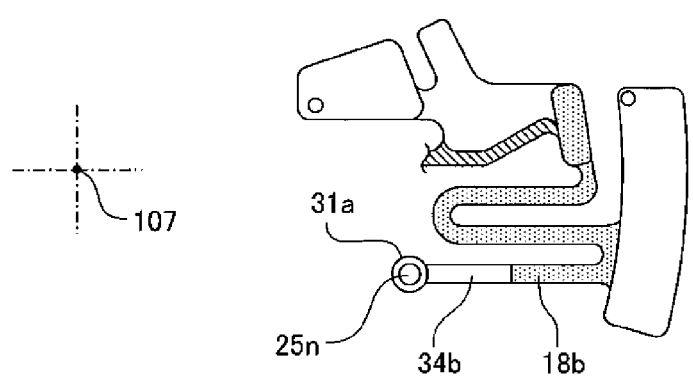

FIG. 28
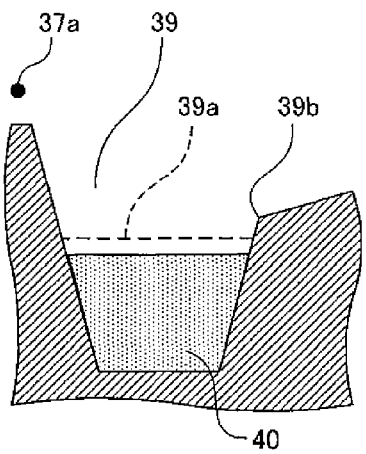
(a)
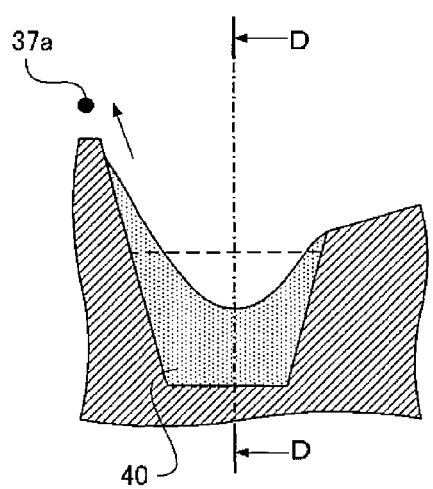
(b)
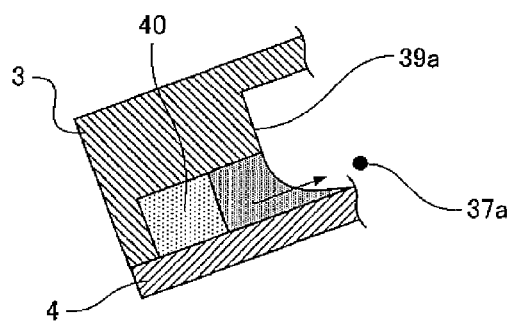
(c)

FIG. 30
(a)
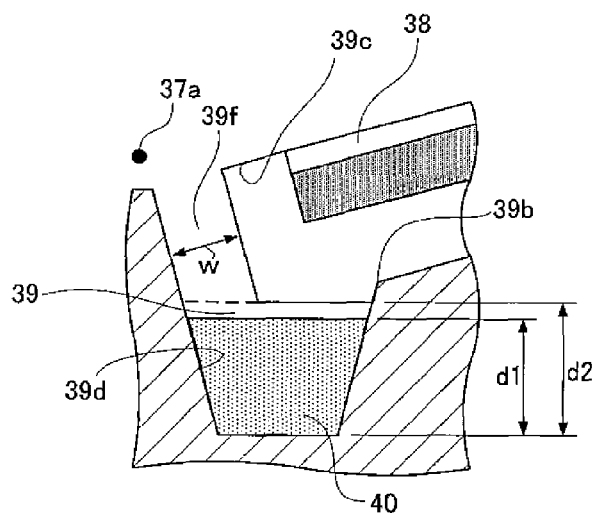
(b)
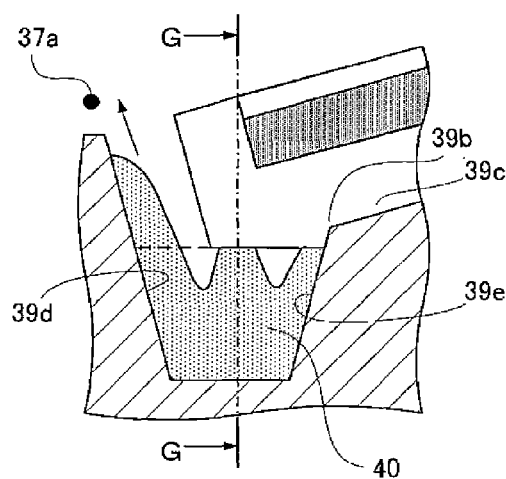
(c)
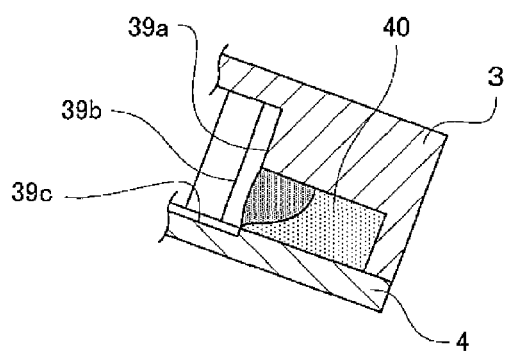

F-F SECTIONAL VIEW

H-H SECTIONAL VIEW

FIG. 37
(a)
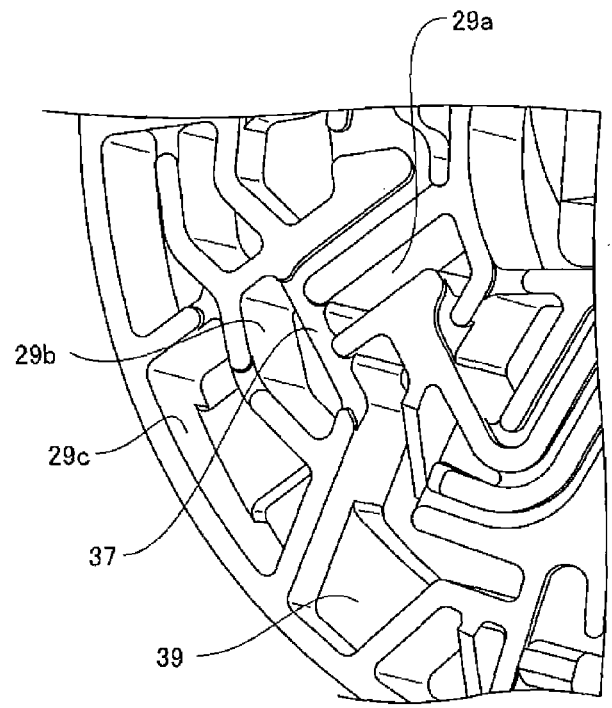
(b)
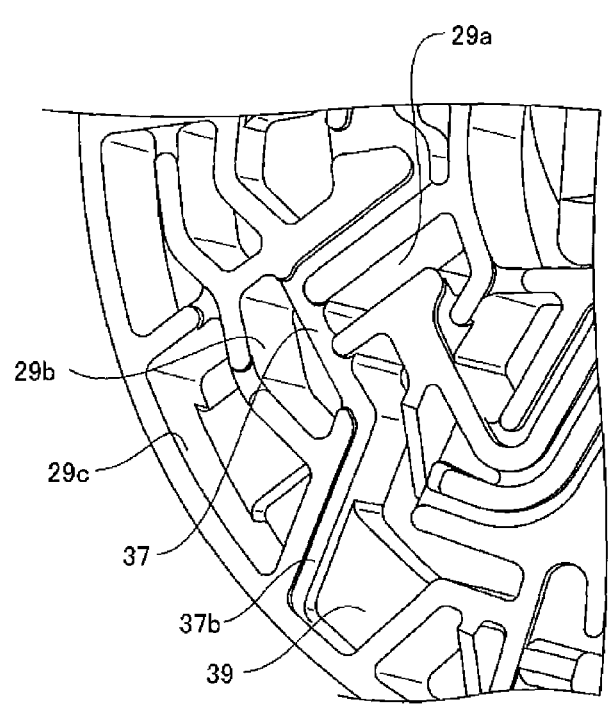

FIG. 38
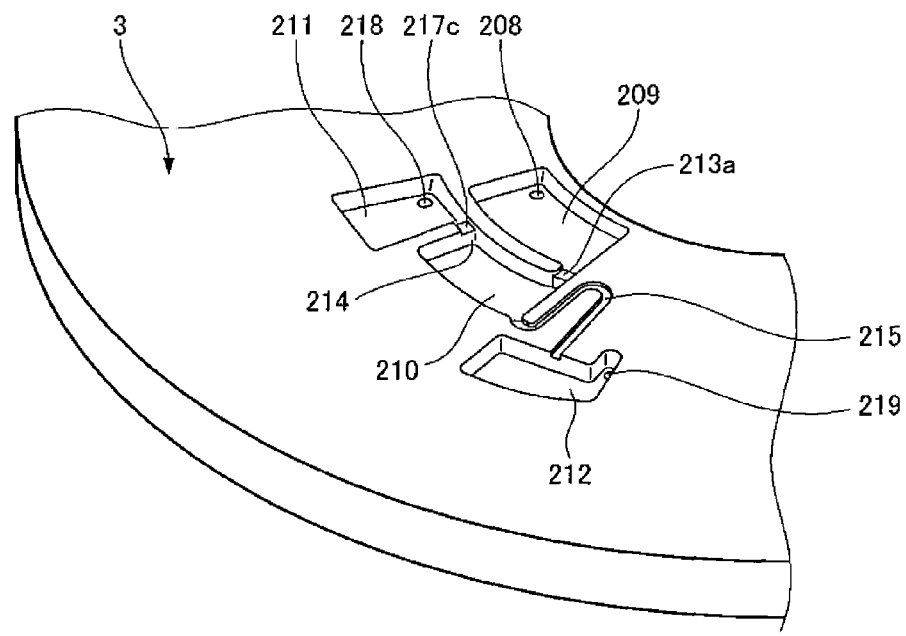
FIG. 39
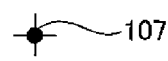
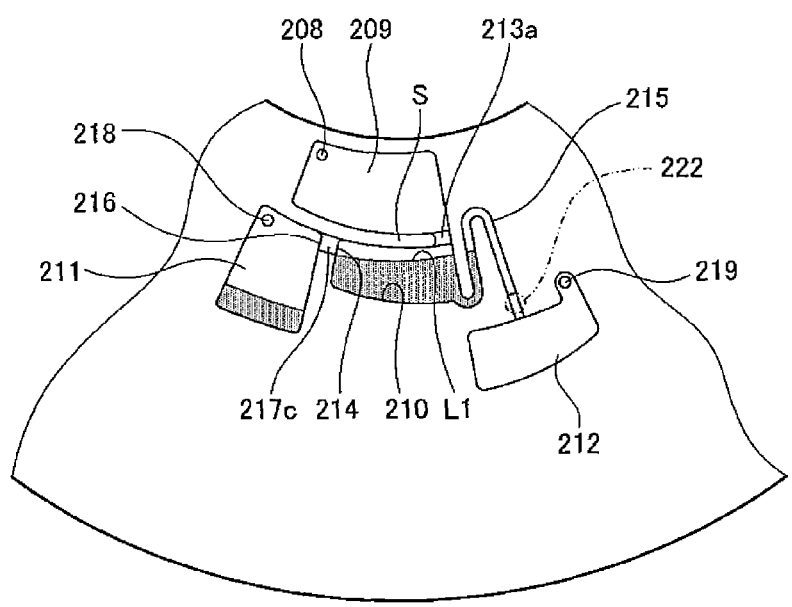

FIG. 40
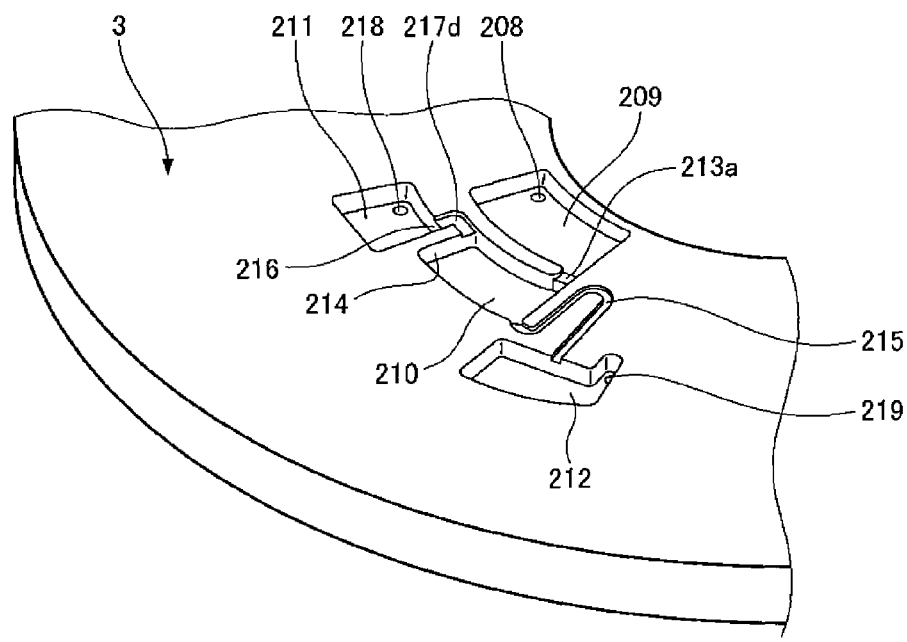
FIG. 41
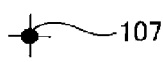
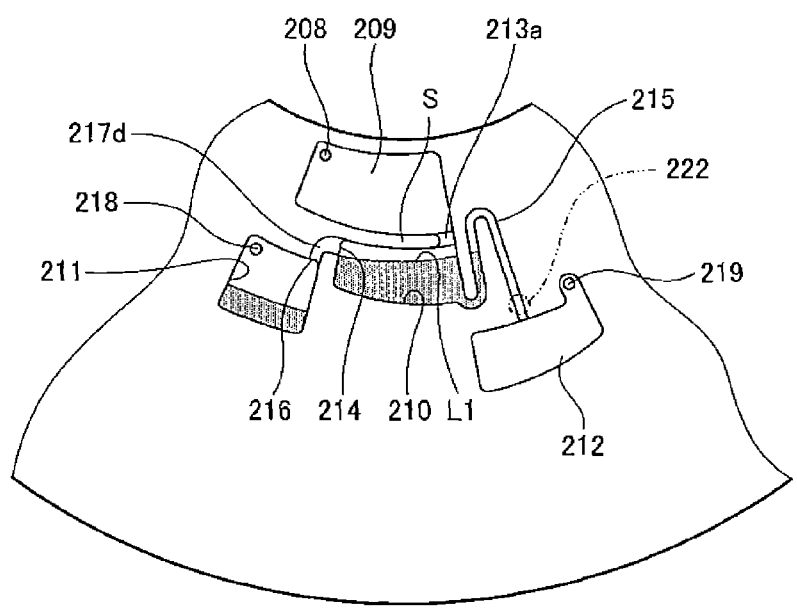

F I G. 4 2
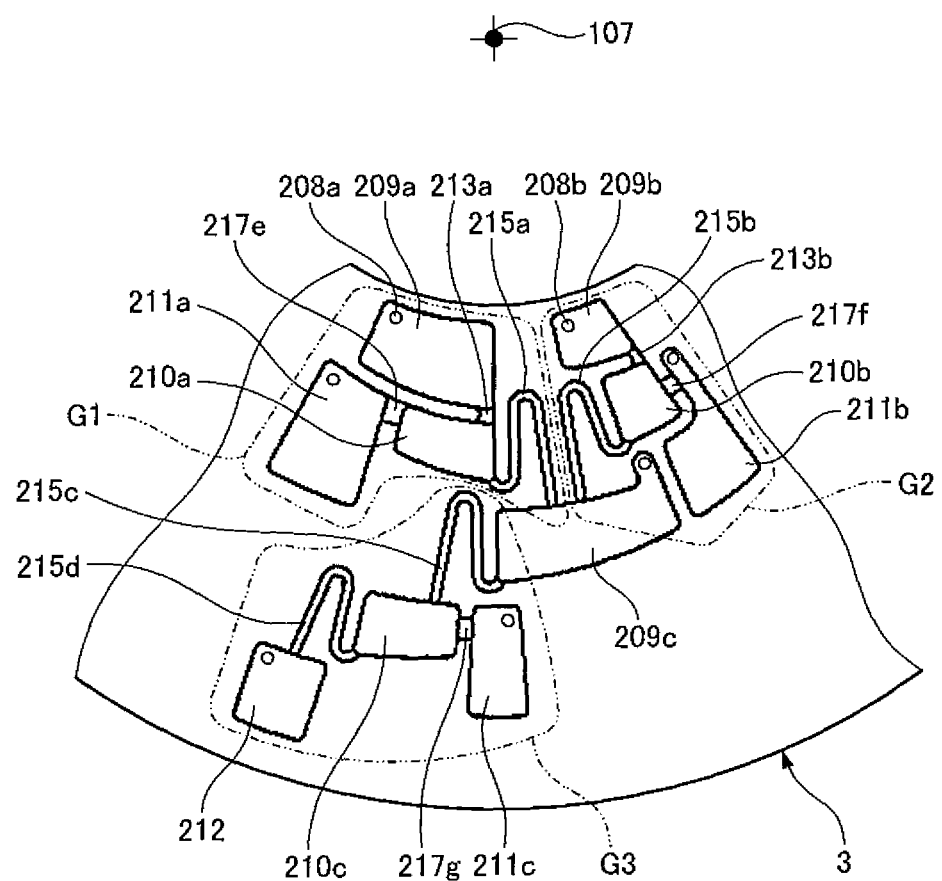

F I G. 4 7
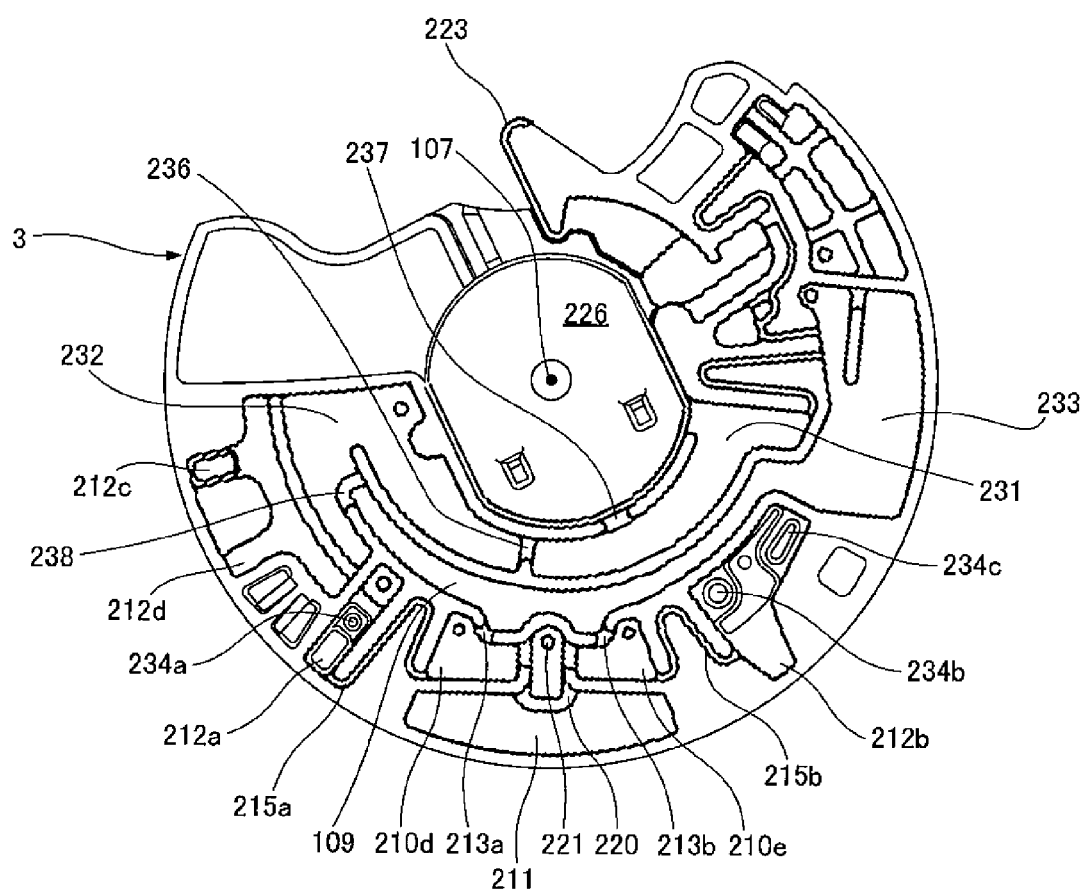

FIG. 53
(a)
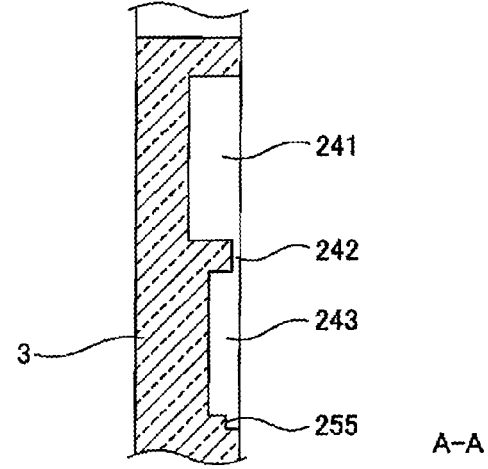
A-A
(b)
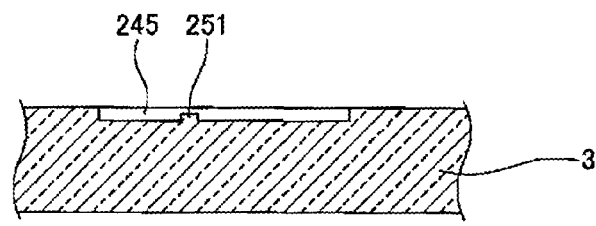
B-B
(c)
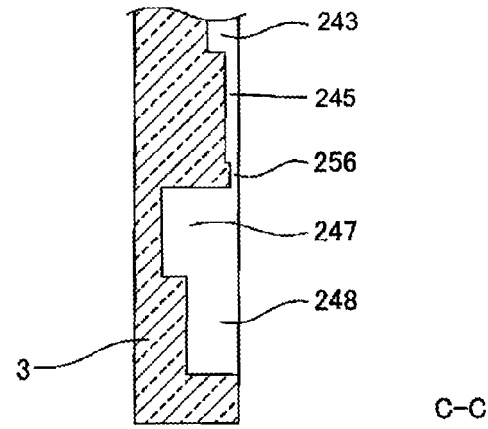
C-C

FIG. 54
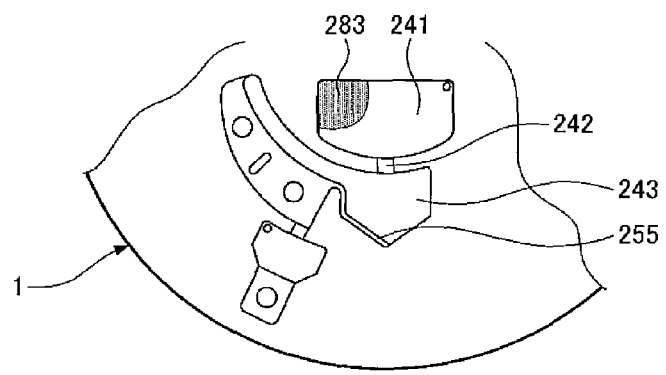
(a)
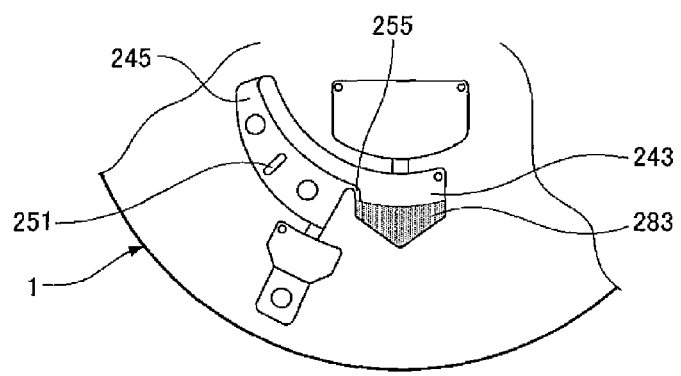
(b)
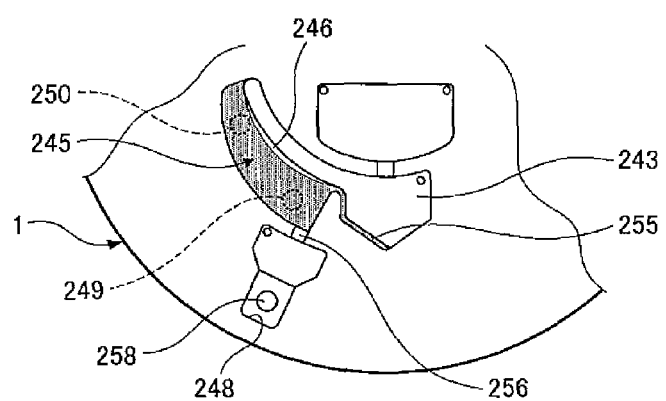
(c)
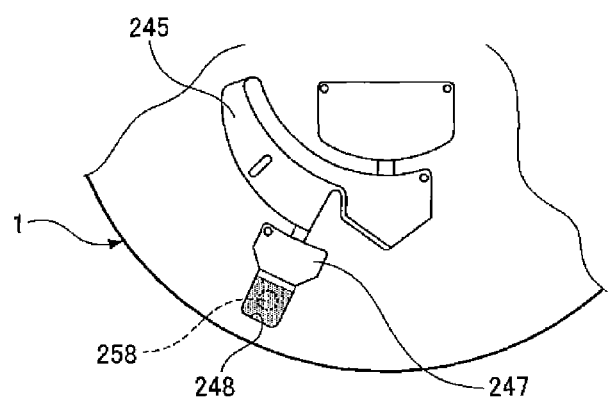
(d)

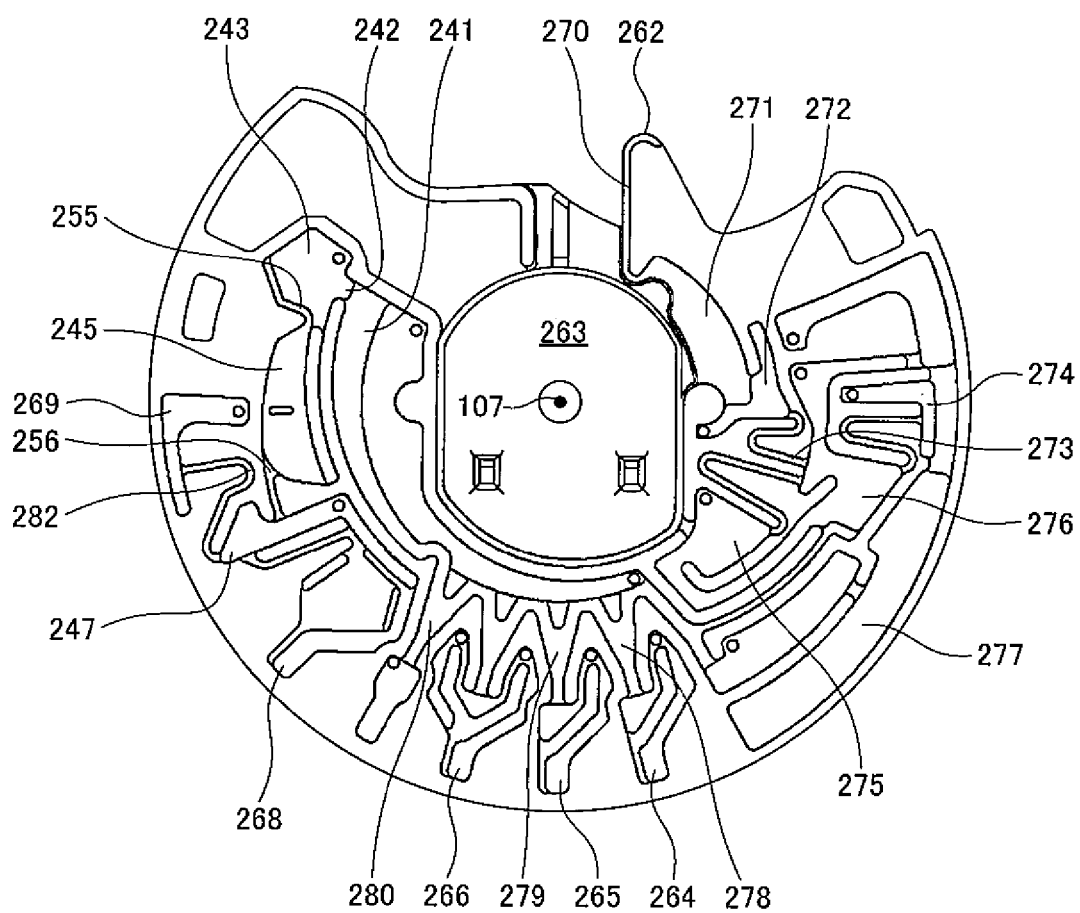
F I G. 5 6

FIG. 60
PRIOR ART
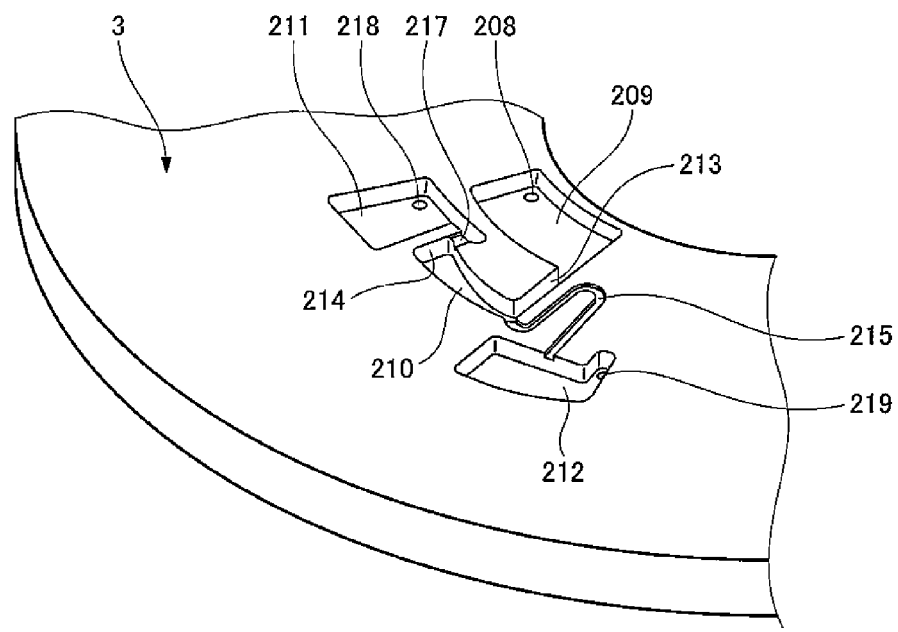
FIG. 61
PRIOR ART
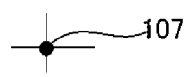
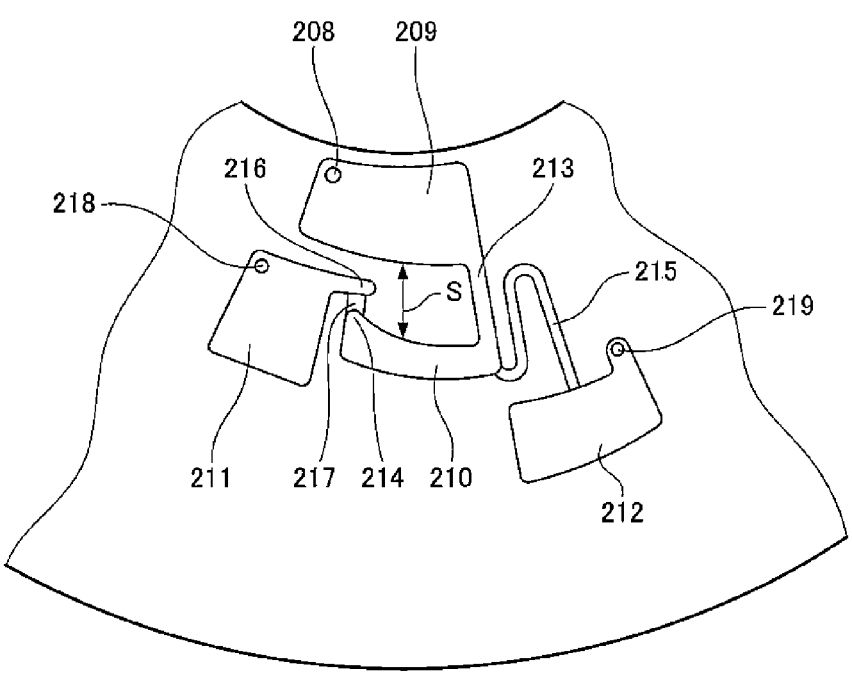

FIG. 62
PRIOR ART
(a) 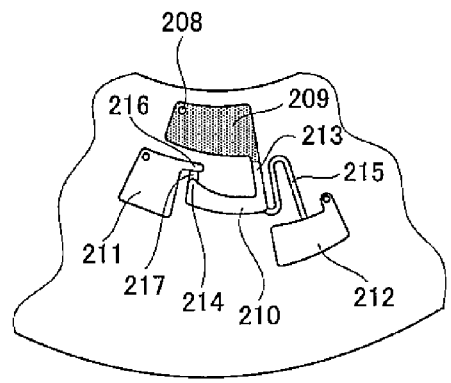
(b) 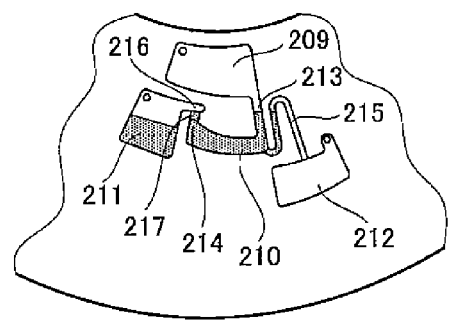
(c) 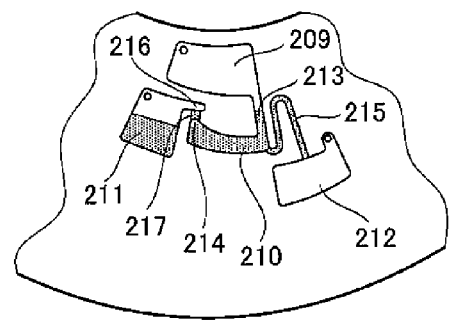
(d) 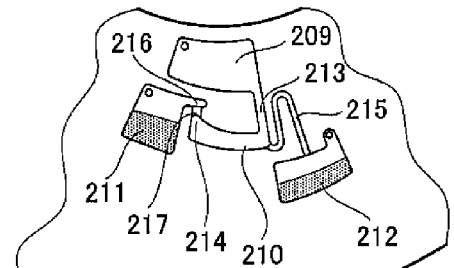

FIG. 63
PRIOR ART
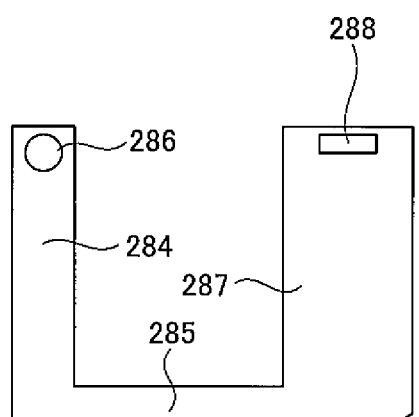
(a)
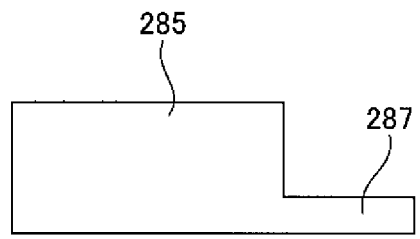
(b)

ANALYZING DEVICE

TECHNICAL FIELD

The present invention relates to an analyzing device used for analyzing a liquid collected from an organism or the like.

BACKGROUND ART

In the related art, a liquid collected from an organism or the like is analyzed by a known analyzing method using an analyzing device having fluid channels formed therein. The analyzing device can control a fluid with a rotator. By using a centrifugal force, the analyzing device can dilute a sample liquid, measure a solution, separate a solid component, transfer and distribute a separated fluid, and mix the solution and a reagent, thereby enabling various biochemical analyses.

Patent Literature 1 describes an analyzing device for transferring a solution by a centrifugal force. As shown in FIG. 57, a sample liquid is injected into a storage cavity 92 from an inlet 91 by an inserting instrument such as a pipette, the sample liquid is transferred to a separating cavity 93 and is centrifugally separated therein by rotations of an analyzing device 90, and then solution components are collected into a measuring passage 95 through a connecting passage 94. At the subsequent rotation of the analyzing device 90, solution components in the measuring passage 95 can be transferred to a measurement spot 96. At this point, in order to prevent whole blood retained in the separating cavity 93 from flowing into the connecting passage 94 and the measuring passage 95 thereafter, a siphon-shaped connecting passage 97 for discharging the whole blood is provided on the outermost part of the separating cavity 93. By using the siphon action of the connecting passage 97, an excessive sample liquid in the separating cavity 93 is discharged into an overflow cavity 98.

Patent Literature 2 describes an analyzing device for transferring a solution by using a centrifugal force. As shown in FIG. 58, a diluent measured by a centrifugal force in a diluent measuring chamber 84 and supernatant plasma centrifugally separated in a separating chamber 80 are transferred into a mixing chamber 86 through siphon passages 82 and 84 by a centrifugal force. After agitation in the mixing chamber 86, the solution is transferred to measurement cells 88, which are provided outside the mixing chamber 86, through a siphon passage 87 and is measured therein.

Patent Literature 3 describes an analyzing device for measuring a sample by using a centrifugal force. The analyzing device is configured as shown in FIGS. 59 to 62.

FIG. 59 shows an analyzing device of the invention. FIG. 60 shows a base substrate on which a microchannel is formed as a principle part of the analyzing device.

In FIG. 59, the analyzing device is made up of a base substrate 3 having microchannels 204a and 204b, a cover substrate 4 closing the opening of the base substrate 3, and an adhesive layer 300.

The microchannels 204a and 204b on the base substrate 3 are formed by injection molding the uneven microchannel pattern of FIG. 60. A sample liquid to be analyzed can be injected into the analyzing device and can be moved by a centrifugal force and a capillary force. In FIG. 61, a rotation axis 107 is the center of rotation of the analyzing device in analysis.

In the analyzing device during measurement, the microchannel 204a is filled with a reaction solution 205 in which a sample liquid has reacted with a reagent. The reaction solution 205 fluctuates in absorbance with a ratio of the sample liquid and the reagent. The microchannel 204a is irradiated with light transmitted from a light source 206 and the quantity of the transmitted light is measured on a light receiving section 207, so that a change of light quantity having passed through the reaction solution 205 can be measured to analyze a state of reaction.

The following will describe the microchannel configuration of the analyzing device and the transfer process of the sample liquid.

FIG. 61 is a plan view showing the microchannel configuration of the analyzing device. FIGS. 62(a) to 62(d) show the transfer process of the analyzing device.

As shown in FIGS. 60 and 61, the microchannel configuration includes a liquid storage chamber 209 for injecting and storing the sample liquid; a measuring chamber 210 for measuring a fixed quantity of the sample liquid and retaining the sample liquid therein; an overflow chamber 211 for receiving an excessive sample liquid when the volume of the sample liquid is larger than the capacity of the measuring chamber 210; and a measurement cell 212 that receives the sample liquid measured in the measuring chamber 210, allows the sample liquid to react with the reagent, and measures absorbance.

The liquid storage chamber 209 is connected to the measuring chamber 210 via a connecting passage 213. As shown in FIG. 62(a), the sample liquid is injected and stored in the liquid storage chamber 209 from an inlet 208 and the analyzing device is rotated, so that the sample liquid can be transferred to the measuring chamber 210 as shown in FIG. 62(b).

The measuring chamber 210 is connected to an inlet 216 of the overflow chamber 211 disposed inside the measuring chamber 210 in the radial direction of rotation, from an overflow port 214 at the innermost position of the measuring chamber 210 in the radial direction of rotation via a capillary passage 217. The measuring chamber 210 is connected to the measurement cell 212 from the outermost position of the measuring chamber 210 in the radial direction of rotation via a connecting passage 215. The overflow chamber 211 has an air hole 218 facilitating the passage of the sample liquid. The measurement cell 212 also has an air hole 219 facilitating the passage of the sample liquid through the connecting passage 215.

The connecting passage 215 has a siphon shape and includes a bent pipe disposed between the rotation axis of the analyzing device and the interface between the inlet 216 of the overflow chamber 211 and the capillary passage 217.

The measuring chamber 210 and the measurement cell 212 are connected thus, so that even when the sample liquid stored in the liquid storage chamber 209 is transferred to the measuring chamber 210 by a rotation of the analyzing device, the sample liquid in the connecting passage 215, as shown in FIG. 62(b), reaches only a position corresponding to a distance from the rotation axis of the analyzing device to the interface between the inlet 216 of the overflow chamber 211 and the capillary passage 217 in the radial direction of rotation.

When the analyzing device is stopped after the measuring chamber 210 is filled with the sample liquid, a capillary force is applied in the connecting passage 215. As shown in FIG. 62(c), the sample liquid reaches the inlet of the measurement cell 212. At this point, the measurement cell 212 has a large depth and the capillary force is quite smaller than that of the connecting passage 215, so that the sample liquid does not flow into the measurement cell 212.

After the connecting passage 215 is filled with the sample liquid, the analyzing device is rotated again, so that as shown in FIG. 62(d), the sample liquid retained in the measuring chamber 210 is transferred to the measurement cell 212 by a siphon action.

Of the wall surfaces of the measuring chamber 210, the inner wall surface in the radial direction of rotation of the analyzing device is formed inward in the radial direction of rotation, from a portion around the connecting passage 213 of the measuring chamber 210 toward a portion around the overflow port 214. In other words, of the wall surfaces of the measuring chamber 210, the inner wall surface in the radial direction of rotation of the analyzing device is positioned closer to the rotation axis in the radial direction of rotation, from the sample liquid inlet of the measuring chamber 210 toward the overflow port. Thus when the sample liquid is transferred from the liquid storage chamber 209, air in the measuring chamber 210 is selectively evacuated to the overflow port 214, so that the measurement of the sample liquid is hardly varied by entrained air when the measuring chamber 210 is filled with the sample liquid.

The capillary passage 217 is 50 µm to 200 µm in depth. During a rotation of the analyzing device, a liquid level is stably measured at a position corresponding to a distance to the interface between the inlet 216 of the overflow chamber 211 and the capillary passage 217 in the radial direction of rotation. At the deceleration/stop of a rotation, the sample liquid is trapped in the capillary passage 217 by a capillary force of the capillary passage 217. Thus it is possible to prevent the sample liquid from flowing into the overflow chamber 211 and achieve precise measurement. Further, the sample liquid trapped in the capillary passage 217 is returned to the measuring chamber 210 by a centrifugal force in the subsequent rotation. Thus the measured sample liquid can be fully transferred to the subsequent process.

The sample liquid injected into the liquid storage chamber 209 is transferred to the measuring chamber 210 thus by a rotation of the analyzing device. The sample liquid exceeding a fixed quantity is discharged into the overflow chamber 211 through the capillary passage 217, so that a predetermined quantity of the sample liquid can be measured.

In Patent Literature 4 shown in FIGS. 63(a) and 63(b), a sample liquid is injected into an inlet passage 284 from an inlet 286 by an inserting instrument such as a pipette, the sample liquid is transferred to a measurement cell 285 by a rotation of an analyzing device, the sample liquid is sucked by a capillary force applied to a passage 287 in response to the deceleration or stop of a rotation, and the rotation is accelerated again to return the sample liquid to the measurement cell 285, so that the sample liquid and a reagent 288 can be stirred.

CITATION LIST

Patent Literature

Patent Literature 1: Japanese Patent Laid-Open No. 2007-078676
Patent Literature 2: National Publication of International Patent Application No. 10-501340
Patent Literature 3: Japanese Patent Laid-Open No. 2007-033225
Patent Literature 4: Japanese Patent Laid-Open No. 2006-145451

SUMMARY OF INVENTION

Technical Problem

In Patent Literature 1, whole blood passing through the connecting passage 97 by a capillary force is varied in transport speed among individuals. Thus sufficient transport time is necessary. However, in the case of a long standby time from the time the sample liquid reaches the outlet of the connecting passage 97 to the subsequent operation, the whole blood of the separating cavity 93 may not be discharged into the overflow cavity 98 because of clogging of the whole blood at the outlet of the connecting passage 97.

An object of the present invention is to provide an analyzing device that can suppress clogging of whole blood at the outlet of the connecting passage 97 and transfer a liquid with higher stability even in the case of a long standby time from the time the sample liquid reaches the outlet of the connecting passage 97 to the subsequent operation.

In Patent Literature 2, it is necessary to dilute plasma. Thus a configuration for collecting plasma and a configuration for measuring a diluent have to be adjacent to the mixing chamber 86 and all the passages for transferring the sample liquid to the subsequent process have to be circumferentially formed, so that the outside diameter of the analyzing device is increased and only a part of a disk shape is used. Disadvantageously, a large unnecessary area indicated by hatching 290 may be generated.

An object of the present invention is to provide an analyzing device that can be reduced in size.

In Patent Literature 3, the inlet 216 of the overflow chamber 211 is disposed inside the overflow port 214 of the measuring chamber 210. Thus it is necessary to provide a space S between the outer periphery of the liquid storage chamber 209 and the inner periphery of the measuring chamber 210, making it difficult to reduce the size of the analyzing device.

The measuring chamber 210 and the overflow chamber 211 are connected via the capillary passage 217 and the flow rate of a liquid transferred to the measuring chamber 210 is larger than the flow rate of a discharged liquid. During the measurement of the sample liquid, the sample liquid in the siphon-shaped connecting passage 215 may be transferred over the innermost bent section of the connecting passage 215 and the unmeasured sample liquid may be transferred to the measurement cell 212.

Further, a fixed quantity of, e.g., several tens µl of the sample liquid is supplied into the measurement cell 212 and absorbance can be measured with a long optical path. However, the fixed quantity of, e.g., several tens µl of the sample liquid is supplied only to the single measurement cell 212, so that multiple items may not be analyzed.

When the sample liquid is obtained by diluting a test object with a diluent, it is necessary to provide a mixing device for mixing a fixed quantity of the test object and a fixed quantity of the diluent, a measuring chamber for measuring a fixed quantity from the diluent, and an overflow chamber for receiving an excessive diluent, upstream of the liquid storage chamber 209 of the base substrate 3. Thus at present, it is further difficult to reduce the size of the analyzing device.

The present invention has been devised to solve the problems of the related art. An object of the present invention is to provide an analyzing device having a measuring mechanism that can be easily reduced in size.

Another object of the present invention is to provide an analyzing method that can simultaneously analyze multiple items by measuring absorbance.

In Patent Literature 4, the measurement cell 285 is disposed orthogonally to the centrifugal direction. Thus in optical measurement of the sample liquid in the measurement cell 285, the measurement cell 285 has to be filled with a large quantity of the sample liquid, making it difficult to reduce the quantity of the sample liquid.

In the case of incorrect control of the quantity of the sample liquid of the measurement cell 285, the volume of the passage 287, and the position of the applied reagent 288 in the passage 287, irregular agitation may occur. When the reagent has a large specific gravity, the reagent may precipitate on the outer periphery of the measurement cell 285, so that the accuracy of measurement may decrease.

Further, an agitating mechanism for agitating the sample liquid and the reagent is U-shaped and is made up of the inlet passage 284, the measurement cell 285, and the passage 287. An area between the inlet passage 284 and the passage 287 is formed as an unnecessary space and thus the agitating mechanism is not suitable for size reduction of the analyzing device.

The present invention has been devised to solve the problems of the related art. An object of the present invention is to provide an analyzing device that can reduce the quantity of a sample liquid, eliminate irregular agitation of the sample liquid and a reagent, and can be properly reduced in size.

Solution to Problem

An analyzing device according to a first aspect of the present invention is an analyzing device having a microchannel structure for transferring a sample liquid to a measurement spot by a centrifugal force generated by rotational driving, the analyzing device being used for reading that accesses a reaction liquid at the measurement spot, the analyzing device including: a first reserving cavity for retaining a sample liquid transferred by the centrifugal force; an operation cavity adjacent to the first reserving cavity in the circumferential direction of the rotational driving; a connecting section provided on the side wall of the first reserving cavity, the connecting section sucking, by a capillary force, the sample liquid retained in the first reserving cavity and transferring the sample liquid to the operation cavity; and a second reserving cavity that is disposed outside the operation cavity in the circumferential direction of the rotational driving, communicates with the outermost position of the operation cavity via a connecting passage, and retains the sample liquid transferred from the operation cavity by the centrifugal force, wherein the connecting section of the operation cavity is circumferentially extended farther than the liquid level of the sample liquid retained in the first reserving cavity, with respect to a rotation axis for generating the centrifugal force.

An analyzing device according to a second aspect of the present invention, in the first aspect, wherein the operation cavity and the connecting section have cross sectional dimensions in the thickness direction and the cross sectional dimensions are regulated to enable the application of the capillary force.

An analyzing device according to a third aspect of the present invention, in the first aspect, further including a cavity on the inner periphery side of the operation cavity, the cavity being opened to the atmosphere.

An analyzing device according to a fourth aspect of the present invention, in the third aspect, wherein the cavity is connected to the first reserving cavity.

An analyzing device according to a fifth aspect of the present invention, in the first aspect, wherein the connecting passage has cross sectional dimensions in the thickness direction and the cross sectional dimensions are regulated such that a capillary force applied to the connecting passage is larger than a capillary force applied to the operation cavity.

An analyzing device according to a sixth aspect of the present invention, in the first aspect, wherein the operation cavity contains reagents and an agitating rib extended around the reagents in the radial direction.

An analyzing method according to a seventh aspect of the present invention, when a sample liquid is transferred to a measurement spot of an analyzing device by a centrifugal force generated by rotational driving, the analyzing method including: transferring the sample liquid to a first reserving cavity by the centrifugal force through a communicating passage to which a capillary force is applied; transferring the sample liquid of the first reserving cavity to an operation cavity adjacent to the first reserving cavity in the circumferential direction of the rotational driving, through a connecting section that is provided on the side wall of the first reserving cavity and receives a capillary force, and metering the sample liquid in the operation cavity, the sample liquid being transferred by stopping or decelerating the rotational driving; oscillating the analyzing device so as to agitate the sample liquid in the operation cavity and dissolving reagents in the operation cavity; and transferring the sample liquid of the operation cavity containing the dissolved reagents to a subsequent measurement spot disposed outside the operation cavity in the circumferential direction of the rotational driving, through the connecting passage receiving the capillary force, the sample liquid being transferred by the centrifugal force generated by the rotational driving.

An analyzing device according to a eighth aspect of the present invention is an analyzing device having a microchannel structure for transferring a sample liquid to a measurement spot by a centrifugal force, the analyzing device being used for reading that accesses a reaction liquid at the measurement spot, the analyzing device including: a separating cavity for separating the sample liquid into a solution component and a solid component by using the centrifugal force; a measuring passage that receives a portion of the solution component separated in the separating cavity and retains the portion of the solution component; a connecting passage whose proximal end is connected to the bottom of the separating cavity, the connecting passage transferring the sample liquid of the separating cavity; an overflow cavity connected to the other end of the connecting passage; and a liquid retaining section provided from the outlet of the connecting passage in the circumferential direction and toward the inner periphery of the analyzing device.

An analyzing device according to a ninth aspect of the present invention, in the eighth aspect, wherein the liquid retaining section has a width w2 that is larger than a width w1 of the connecting passage.

An analyzing device according to a tenth aspect of the present invention is an analyzing device having a microchannel structure for transferring a sample liquid to a measurement spot by a centrifugal force, the analyzing device being used for reading that accesses a reaction liquid at the measurement spot, the analyzing device including: a separating cavity for separating the sample liquid into a solution component and a solid component by using the centrifugal force; a measuring passage that receives a portion of the solution component separated in the separating cavity and retains the portion of the solution component; a connecting passage whose proximal end is connected to the bottom of the separating cavity, the connecting passage transferring the sample liquid of the separating cavity; an overflow cavity connected to the other end of the connecting passage; and a liquid retaining connecting passage provided from the outlet of the connecting passage in the circumferential direction.

An analyzing method according to an eleventh aspect of the present invention includes: separating a sample liquid received by a separating cavity into a solution component and a solid component by a centrifugal force; transferring the solution component, which has been separated in the separating cavity, to a measurement spot by a centrifugal force and analyzing the solution component by accessing a reaction liquid at the measurement spot; sucking the sample liquid left in the separating cavity, by a capillary force of a connecting passage whose proximal end is connected to the bottom of the outer periphery of the separating cavity and front end is opened at an overflow cavity; and storing the sample liquid in a state in which a width w2 of the opening of the connecting passage at the overflow cavity is larger than a width w1 of a passage to the front end of the connecting passage, and then discharging the sample liquid of the separating cavity to the overflow cavity by applying the largest centrifugal force to the separating cavity.

An analyzing method according to a twelfth aspect of the present invention includes: separating a sample liquid received by a separating cavity into a solution component and a solid component by a centrifugal force; transferring the solution component, which has been separated in the separating cavity, to a measurement spot by a centrifugal force and analyzing the solution component by accessing a reaction liquid at the measurement spot; sucking the sample liquid left in the separating cavity, by a capillary force of a connecting passage whose proximal end is connected to the bottom of the outer periphery of the separating cavity and front end is opened at an overflow cavity; and further sucking the sample liquid at the opening of the connecting passage at the overflow cavity through a liquid retaining connecting passage by a capillary force, and then discharging the sample liquid of the separating cavity to the overflow cavity by applying the largest centrifugal force to the separating cavity.

An analyzing device according to a thirteenth aspect of the present invention is an analyzing device having a microchannel structure for transferring a sample liquid to a measurement spot by a centrifugal force, the analyzing device including a capillary passage for feeding a liquid in the circumferential direction from an upstream process to a downstream process, the capillary passage crossing an overflow cavity for feeding a liquid in a direction along which the centrifugal force is applied from the rotation axis to the outer periphery of the analyzing device, wherein the liquid of the overflow cavity is discharged over the capillary passage by the centrifugal force.

An analyzing device according to a fourteenth aspect of the present invention is an analyzing device having a microchannel structure for transferring a sample liquid to a measurement spot by a centrifugal force, the analyzing device being used for measuring a fixed quantity of a diluent in a reserving cavity, discharging an excessive diluent from the reserving cavity to a chamber through an overflow cavity, diluting the sample liquid by mixing the sample liquid and the fixed quantity of the diluent in a mixing cavity, transferring the sample liquid diluted in the mixing cavity to the measurement spot through a capillary passage, and reading that accesses a reaction liquid at the measurement spot, wherein the reserving cavity and the mixing cavity are arranged in the circumferential direction from the center to the outer periphery of the analyzing device, the overflow cavity and the chamber are arranged on the sides of the reserving cavity and the mixing cavity in the circumferential direction, the capillary passage is disposed at a point of the overflow cavity so as to cross the flowing direction of the excessive diluent toward the chamber, and the excessive diluent of the overflow cavity is supplied into the chamber over the capillary passage by the centrifugal force.

An analyzing device according to a fifteenth aspect of the present invention further includes a sealing overflow cavity between an atmospheric-side overflow cavity communicating with the atmosphere and the chamber, the sealing overflow cavity communicating with the chamber via a first overflow passage and communicating with the atmospheric-side overflow cavity via a second overflow passage, wherein the outlets of the chamber and the sealing overflow cavity are sealed from the atmosphere and a negative pressure is generated in the chamber and the sealing overflow cavity when the sample liquid is transferred from the mixing cavity through the capillary passage.

An analyzing method using an analyzing device according to a sixteenth aspect of the present invention, the analyzing device having a microchannel structure for transferring a sample liquid to a measurement spot by a centrifugal force, wherein a fixed quantity of a diluent is measured in a reserving cavity by the centrifugal force, an excessive diluent is discharged from the reserving cavity to a chamber through an overflow cavity over a capillary passage disposed at a point of the overflow cavity so as to cross the flowing direction of the excessive diluent toward the chamber, the sample liquid diluted in the mixing chamber is transferred to the measurement spot through the capillary passage while the sample liquid is tilted at a contact position on one end of the capillary passage, and a reaction liquid is accessed and read at the measurement spot.

An analyzing device according to a seventeenth aspect of the present invention includes: a measuring chamber that is connected to a liquid storage chamber via a connecting passage, is disposed outside the liquid storage chamber in the radial direction of rotation, and retains a fixed quantity of a liquid received from the liquid storage chamber; an overflow chamber that is connected to the measuring chamber and receives an excessive quantity of the liquid; and a measurement cell that is disposed in the subsequent stage of the measuring chamber and measures the liquid received from the measuring chamber, wherein the inlet of the overflow chamber and the overflow port of the measuring chamber are connected via a capillary passage extending along the radial direction of rotation.

An analyzing device according to an eighteenth aspect of the present invention includes: a measuring chamber that is connected to a liquid storage chamber via a connecting passage, is disposed outside the liquid storage chamber in the radial direction of rotation, and retains a fixed quantity of a liquid received from the liquid storage chamber; an overflow chamber that is connected to the measuring chamber and receives an excessive quantity of the liquid; and a measurement cell that is disposed in the subsequent stage of the measuring chamber and measures the liquid received from the measuring chamber, wherein the overflow port of the measuring chamber and the inlet of the overflow chamber are connected via a capillary passage extending outside the overflow port in the radial direction of rotation.

An analyzing device according to a nineteenth aspect of the present invention includes: a first measuring chamber that is connected to a liquid storage chamber via a first connecting passage, is disposed outside the liquid storage chamber in the radial direction of rotation, and retains a fixed quantity of a liquid received from the liquid storage chamber; a second measuring chamber that is connected to the liquid storage chamber via a second connecting passage, is disposed outside the liquid storage chamber in the radial direction of rotation, and retains a fixed quantity of the liquid received from the liquid storage chamber; an overflow chamber that is disposed between the first measuring chamber and the second measuring chamber, is connected to the first measuring chamber and the second measuring chamber, and receives an excessive quantity of the liquid; a first measurement cell that is disposed in the subsequent stage of the first measuring chamber and measures the liquid received from the first measuring chamber; and a second measurement cell that is disposed in the subsequent stage of the second measuring chamber and measures the liquid received from the second measuring chamber, wherein the inlet of the overflow chamber and the first overflow port of the first measuring chamber are connected via a first capillary passage extending along the radial direction of rotation, and the inlet of the overflow chamber and the second overflow port of the second measuring chamber are connected via a second capillary passage extending along the radial direction of rotation.

An analyzing method according to a twentieth aspect of the present invention includes: transferring, by rotating an analyzing device, one of a diluent and a sample liquid to be analyzed in a liquid storage chamber to multiple measuring chambers disposed outside the liquid storage chamber of the analyzing device along the radius of rotation, and transferring an excessive quantity of one of the diluent and the sample liquid in metering of the measuring chambers to an overflow chamber disposed outside the measuring chambers of the analyzing device along the radius of rotation; transferring one of the diluent and the sample liquid that have been metered in the measurement chambers to the multiple measurement cells of the analyzing device by rotating the analyzing device after the rotation of the analyzing device is decelerated or stopped, and reacting a fixed quantity of the sample liquid with a reagent set in each of the measurement cells, the measurement cells being disposed in the subsequent stage of the multiple measuring chambers; and passing light through analytes in the respective measurement cells and measuring the absorbance of each of the analytes during the rotation of the analyzing device.

Advantageous Effects of Invention

With the configurations of first to seventh aspects of the present invention, even a small quantity of sample liquid can be moved between a first reserving cavity and an operation cavity via a connecting section by controlling a centrifugal force generated by rotational driving, so that a reagent contained in the operation cavity can be sufficiently agitated with the sample liquid. After the agitation of the reagent and the sample liquid, the sample liquid of the operation cavity can be transferred to a second reserving cavity through a connecting passage by controlling the centrifugal force generated by the rotational driving, and transmittance can be measured and analyzed in the second reserving cavity. Further, the first reserving cavity and the operation cavity are arranged in the circumferential direction, thereby reducing the size of an analyzing device.

With the configurations of eighth to twelfth aspects, an overflow cavity is provided that is connected to the other end of the connecting passage, and a liquid retaining section is provided from the outlet of the connecting passage in the circumferential direction and to the inner periphery of the analyzing device or a liquid retaining connecting passage is provided from the outlet of the connecting passage in the circumferential direction, thereby suppressing clogging of whole blood at the outlet of the connecting passage even in the case of a long standby time.

With the configurations of thirteenth to sixteenth aspects, a capillary passage feeding a liquid from an upstream process to a downstream process in the circumferential direction is disposed at a point of the overflow cavity feeding a liquid in a direction from the rotation axis to the outer periphery of the analyzing device such that the capillary passage crosses the overflow cavity, and the liquid of the overflow cavity is discharged over the capillary passage by the centrifugal force. Thus it is possible to transfer the diluted sample liquid to the measurement spot through the capillary passage, reducing the size of the analyzing device.

With the configurations of seventeenth to twentieth aspects, a space between a liquid storage chamber and a measuring chamber can be reduced. Thus chambers disposed in the radial direction can be arranged close to the inner periphery of the analyzing device, reducing the size of the analyzing device. Further, the sample liquid transferred to the measuring chamber can be regulated to a flow rate smaller than the flow rate of the discharged sample liquid, thereby eliminating errors during measurement. In the case where multiple measurement chambers are provided at the same time, the sample liquid can be measured in the respective measuring chambers, enabling measurement of multiple items.

BRIEF DESCRIPTION OF THE DRAWINGS

FIG. 1 is a perspective view showing an analyzing device with an opened and closed protective cap according to a first embodiment of the present invention.

FIG. 2 shows a front view and a bottom view of the analyzing device according to the first embodiment.

FIG. 5 shows a plan view, a side view, a B-B sectional view, and a front view of the protective cap according to the first embodiment.

FIG. 12 is an enlarged plan view of the turntable, for explanation of engagement between the turntable and a projecting section of the analyzing device according to the first embodiment.

FIG. 16 shows a state diagram in which the analyzing device retaining the sample liquid in a capillary cavity is set on the turntable with a broken aluminum seal of a diluent solution, and a state diagram showing the analyzing device is separated from the turntable according to the first embodiment.

FIG. 18 shows a state diagram in which the sample liquid flows into a measuring passage from a separating cavity and a fixed quantity of the sample liquid is retained in the measuring passage in step 3, and a state diagram in which the sample liquid flows into a mixing cavity from the measuring passage in step 4 according to the first embodiment.

FIG. 19 shows a state diagram of the analyzing device oscillated in step 6 of the first embodiment, and a state diagram in which the turntable is rotationally driven in a clockwise direction to cause the sample liquid to flow into a measuring chamber and a reserving cavity.

FIG. 20 shows a state diagram of the analyzing device oscillated in step 8 of the first embodiment, and a state diagram in which the turntable is rotationally driven in the clockwise direction in step 9 to cause diluted plasma having reacted with the reagent of an operation cavity to flow into the separating cavity, and aggregates generated in the operation cavity are centrifugally separated by keeping a high-speed rotation.

FIG. 21 shows a state diagram in which the turntable is stopped, the diluted plasma flows into the measuring passage, and a fixed quantity of the diluted plasma is retained in the measuring passage in step 10 of the first embodiment, and a state diagram in which the diluted plasma retained in the measuring passage flows into the measuring chamber in step 11.

FIG. 22 shows a state diagram in which a reaction of the diluted plasma in the measuring chamber and reagents is started in step 12 of the first embodiment, and a state diagram of the agitation of the reagents and the diluted plasma in step 13.

FIG. 23 shows an enlarged perspective view in which the diluent from the diluent container flows into the reserving cavity through a discharging passage in step 2 of the first embodiment, and an enlarged perspective view in which the diluted plasma is transferred from the mixing cavity to the subsequent process through a capillary passage.

FIG. 24 shows an explanatory drawing of problems when the sample liquid remaining in the separating cavity is discharged to an overflow cavity, and a plan view of the principle part of the analyzing device as an improvement example of the first embodiment.

FIG. 28 shows a plan view of a liquid level state of a mixing cavity before the oscillation of an analyzing device according to a third example of the first embodiment, a plan view of a liquid level state of the mixing cavity after oscillation, and a D-D sectional view of the mixing cavity.

FIG. 30 shows a plan view of a liquid level state of a mixing cavity before the oscillation of an analyzing device according to a fourth example of the first embodiment, a plan view of a liquid level state of the mixing cavity after oscillation, and a G-G sectional view of the mixing cavity.

FIG. 37 shows a perspective view of a portion around the inlet of a capillary passage 37 from a mixing cavity 39 and a perspective view of a second embodiment.

FIG. 38 is a perspective view showing the microchannel configuration of the base substrate of an analyzing device according to a third embodiment of the present invention.

FIG. 39 is a plan view showing the microchannel configuration of the base substrate of the analyzing device according to the third embodiment.

FIG. 40 is a perspective view showing the microchannel configuration of the base substrate of an analyzing device according to a fourth embodiment of the present invention.

FIG. 41 is a plan view showing the microchannel configuration of the base substrate of the analyzing device according to the fourth embodiment.

FIG. 42 is a plan view showing a modification of the third embodiment of the present invention according to a fifth embodiment.

FIG. 47 is a plan view showing the microchannel configuration of the base substrate of the analyzing device according to the seventh embodiment.

FIG. 53 shows A-A, B-B, and C-C sectional views of FIG. 50.

FIG. 54 shows a process diagram of a transfer process according to the ninth embodiment.

FIG. 56 is a plan view showing the microchannel configuration of the base substrate of the analyzing device according to the tenth embodiment.

FIG. 60 is a perspective view showing a base substrate according to the related art.

FIG. 61 is a plan view showing the microchannel configuration of an analyzing device according to the related art.

FIG. 62 shows a process diagram of a transfer process according to the related art.

FIG. 63 shows a plan view and a sectional view of Patent Literature 4.

DESCRIPTION OF EMBODIMENTS

First Embodiment

FIGS. 1 to 6 show an analyzing device.

Figure 3:
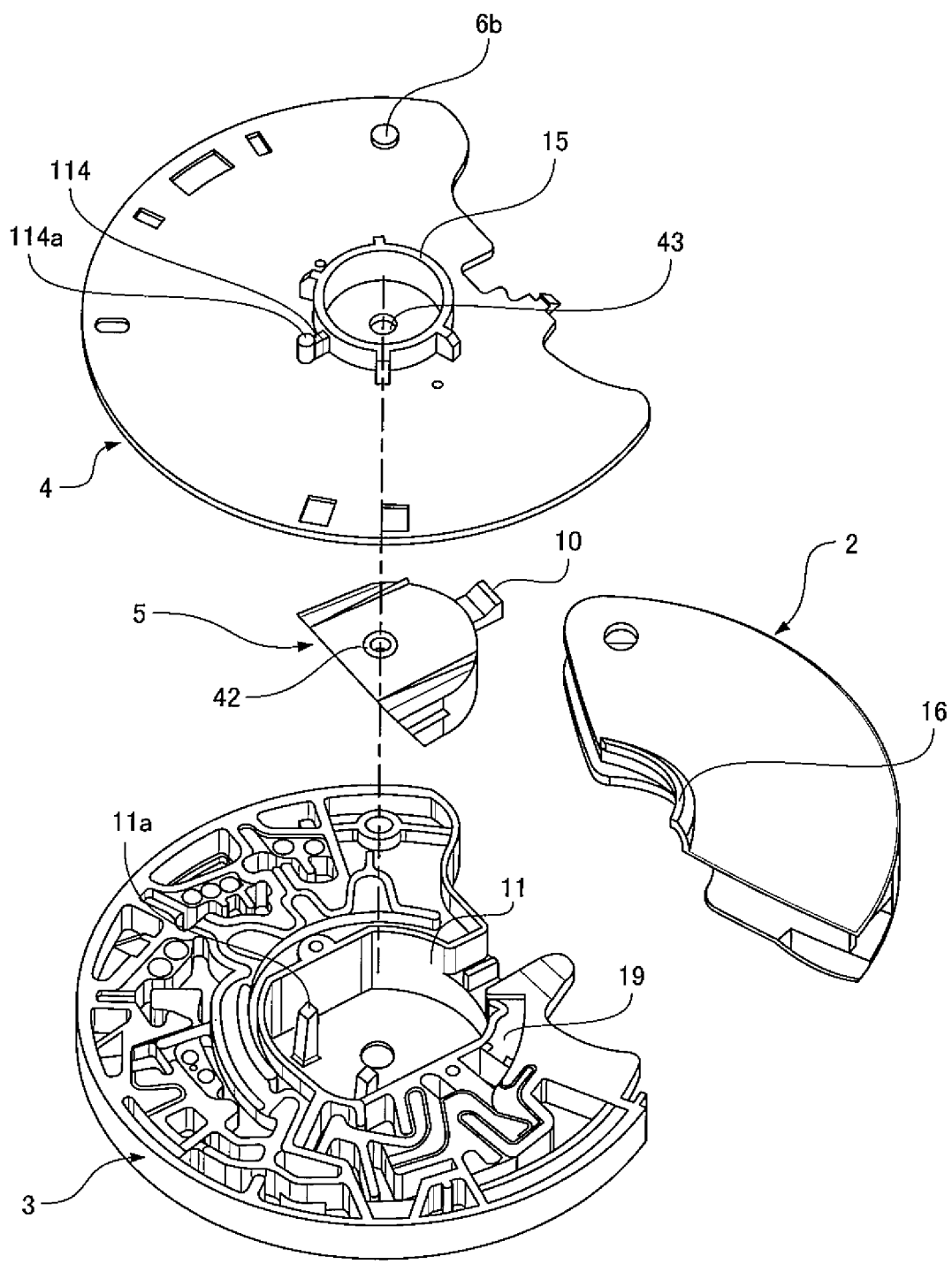
FIG. 3 is an exploded perspective view showing the analyzing device according to the first embodiment.

FIGS. 1(a) and 1(b) show an analyzing device 1 with an opened and closed protective cap 2. FIGS. 2(a) and 2(b) are a front view and a bottom view of the analyzing device 1. FIG. 3 is an exploded view of the analyzing device 1 with the underside of FIG. 1(a) placed face up.

The analyzing device 1 is made up of four components of a base substrate 3 having a microchannel structure formed on one surface of the base substrate 3, the microchannel structure having a minutely uneven surface, a cover substrate 4 covering the surface of the base substrate 3, a diluent container 5 for retaining a diluent, and the protective cap 2 for preventing splashes of a sample liquid.

On the bottom of the analyzing device 1, that is, on the cover substrate 4, a rotary support section 15 is formed that protrudes on the bottom of the analyzing device 1 and acts as a centering fitting part. On the inner periphery of the protective cap 2, a rotary support section 16 is formed. In the analyzing device 1 with the protective cap 2 closed, the rotary support section 16 is formed in contact with the outer periphery of the rotary support section 15. On the cover substrate 4, a projecting section 114 is formed as a detent locking section having the proximal end connected to the rotary support section 15 and the other end extending to the outer periphery of the analyzing device 1.

The base substrate 3 and the cover substrate 4 are joined to each other with the diluent container 5 or the like set in the base substrate 3 and the cover substrate 4, and the protective cap 2 is attached to the joined base substrate 3 and cover substrate 4.

The cover substrate 4 covers the openings of several recessed sections formed on the top surface of the base substrate 3, thereby forming multiple storage areas and the passages of the microchannel structure connecting the storage areas, which will be described later.

In necessary ones of the storage areas, reagents required for various analyses are set beforehand. One side of the protective cap 2 is pivotally supported such that the protective cap 2 can be opened and closed in engagement with shafts 6a and 6b formed on the base substrate 3 and the cover substrate 4. When a sample liquid to be inspected is blood, the passages of the microchannel structure receiving a capillary force have clearances of 50 μm to 300 μm.

The outline of an analyzing process using the analyzing device 1 is that a sample liquid is dropped into the analyzing device 1 in which the diluent has been set, at least a portion of the sample liquid is diluted with the diluent, and then measurement is conducted.

Figure 4:
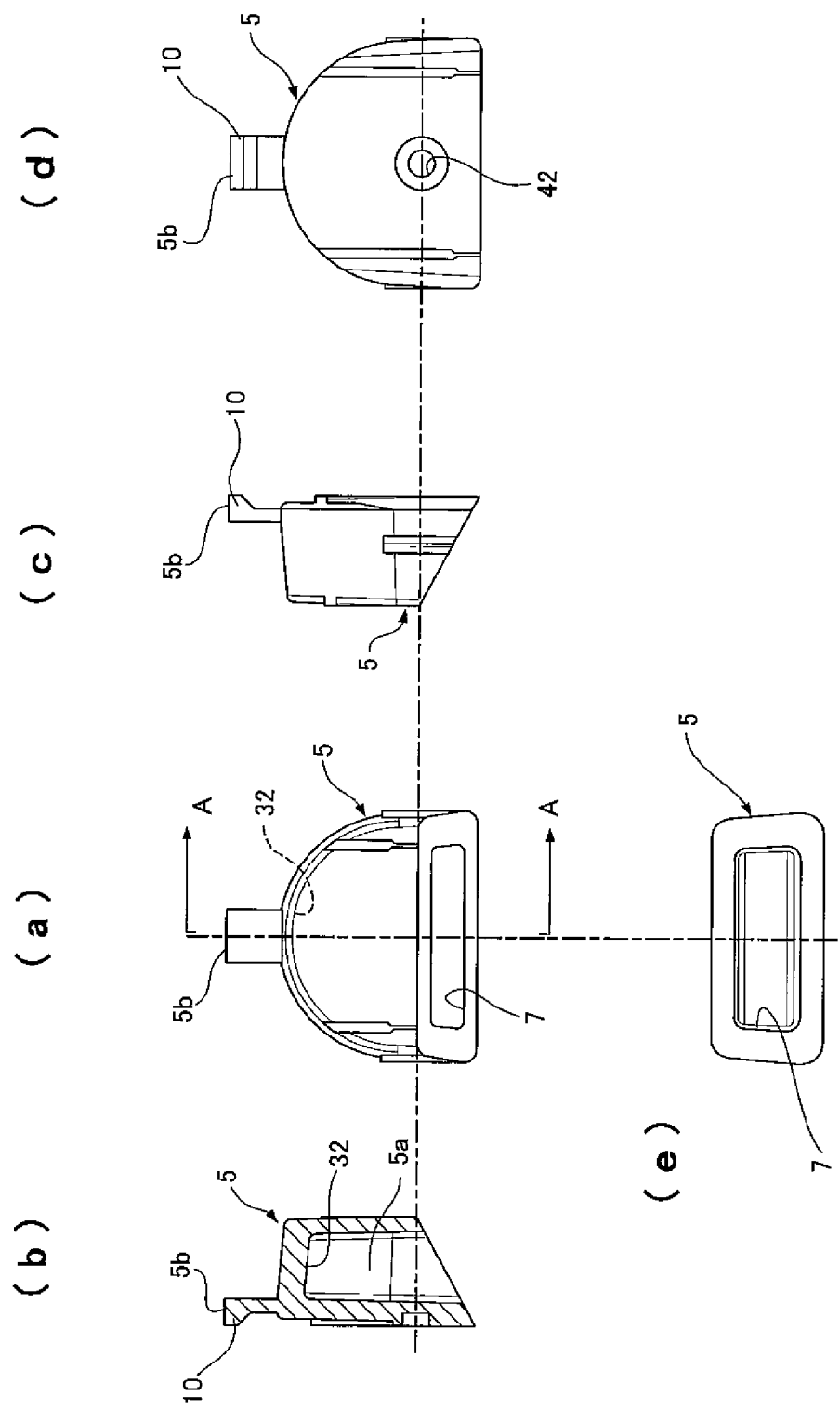
FIG. 4 shows a front view, an A-A sectional view, a side view, a rear view, and a front view of a diluent container according to the first embodiment.

FIG. 4 shows the shape of the diluent container 5.

FIG. 4(a) is a plan view, FIG. 4(b) is an A-A sectional view of FIG. 4(a), FIG. 4(c) is a side view, FIG. 4(d) is a rear view, and FIG. 4(e) is a front view taken from an opening 7. After an interior 5a of the diluent container 5 is filled with a diluent 8 as shown in FIG. 6(a), the opening 7 is enclosed with an aluminum seal 9 serving as a sealing member. On the opposite side of the diluent container 5 from the opening 7, a latch section 10 is formed. The diluent container 5 is set in a diluent container storage part 11 formed between the base substrate 3 and the cover substrate 4, and is accommodated movably between a liquid retaining position shown in FIG. 6(a) and a liquid discharging position shown in FIG. 6(c).

FIG. 5 shows the shape of the protective cap 2.

FIG. 5(a) is a plan view, FIG. 5(b) is a side view, FIG. 5(c) is B-B sectional view of FIG. 5(a), and FIG. 5(d) is a rear view of the protective cap according to the first embodiment. In the protective cap 2, a locking groove 12 is formed. In the closed state of FIG. 1(a), the latch section 10 of the diluent container 5 can be engaged with the locking groove 12 as shown in FIG. 6(a).

FIG. 6(a) shows the analyzing device 1 before use. In this state, the protective cap 2 is closed and the latch section 10 of the diluent container 5 is engaged with the locking groove 12 of the protective cap 2 to lock the diluent container 5 at the liquid retaining position, so that the diluent container 5 does not move in the direction of arrow J. The analyzing device 1 in this state is supplied to a user.

Figure 6:
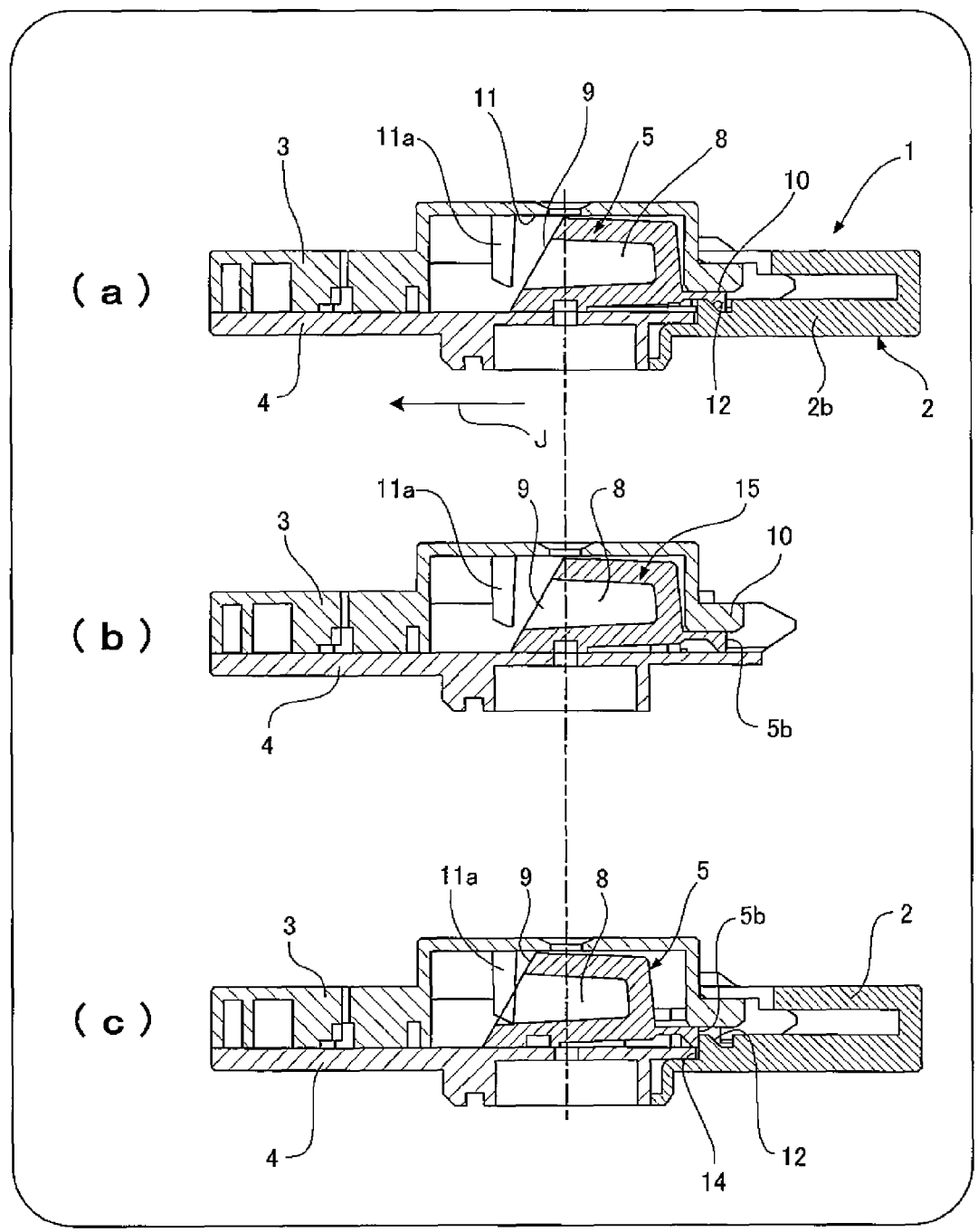
FIG. 6 shows sectional views of the closed diluent container, the opened protective cap, and a discharged diluent.

When the sample liquid is dropped, the protective cap 2 is opened as shown in FIG. 1(*b*) against the engagement with the latch section 10 in FIG. 6(*a*). At this point, a bottom 2*b* of the protective cap 2 is elastically deformed with the locking groove 12 formed on the bottom 2*b*, thereby disengaging the latch section 10 of the diluent container 5 from the locking groove 12 of the protective cap 2 as shown in FIG. 6(*b*).

In this state, the sample liquid is dropped to an exposed inlet 13 of the analyzing device 1 and then the protective cap 2 is closed. At this point, by closing the protective cap 2, a wall surface 14 forming the locking groove 12 comes into contact with a surface 5*b* of the latch section 10 of the diluent container 5 on the protective cap 2, and the wall surface 14 presses the diluent container 5 in the direction of arrow J (a direction that comes close to the liquid discharging position). The diluent container storage part 11 has an opening rib 11*a* formed as a section projecting from the base substrate 3. When the diluent container 5 is pressed by the protective cap 2, the aluminum seal 9 provided on the inclined seal face of the opening 7 of the diluent container 5 is collided with and broken by the opening rib 11*a* as shown in FIG. 6(*c*).

Figure 7:
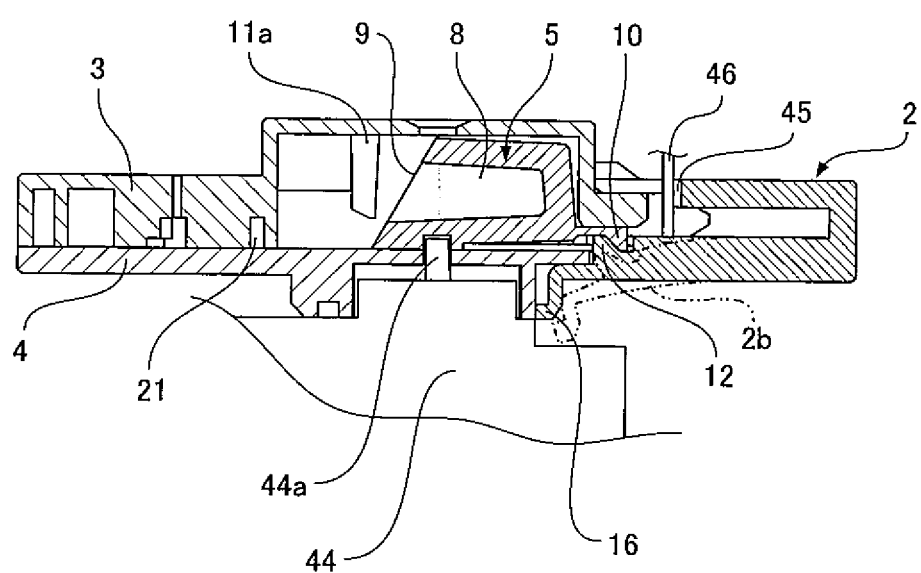
FIG. 7 is a sectional view showing a step of setting the analyzing device in a shipment state according to the first embodiment.

FIG. 7 shows a manufacturing process in which the analyzing device 1 is set at the shipment state of FIG. 6(*a*). First, before the protective cap 2 is closed, a groove 42 (see FIGS. 3 and 4(*d*)) provided on the undersurface of the diluent container 5 and a hole 43 provided on the cover substrate 4 are aligned with each other, and a projecting section 44*a* of a locking member 44 is engaged with the groove 42 of the diluent container 5 through the hole 43 at the liquid retaining position. The projecting section 44*a* is provided separately from the base substrate 3 or the cover substrate 4. The diluent container 5 is set so as to be locked at the liquid retaining position. Further, from a notch 45 (see FIG. 1) formed on the top surface of the protective cap 2, a pressing member 46 is inserted and presses the bottom of the protective cap 2 to elastically deform the protective cap 2. In this state, the protective cap 2 is closed and then the pressing member 46 is removed, so that the analyzing device 1 can be set in the state of FIG. 6(*a*).

The present embodiment described an example in which the groove 42 is provided on the undersurface of the diluent container 5. The groove 42 may be provided on the top surface of the diluent container 5 and the hole 43 may be provided on the base substrate 3 in alignment with the groove 42 such that the projecting section 44*a* of the locking member 44 is engaged with the groove 42.

Further, the locking groove 12 of the protective cap 2 is directly engaged with the latch section 10 of the diluent container 5 to lock the diluent container 5 at the liquid retaining position. The locking groove 12 of the protective cap 2 and the latch section 10 of the diluent container 5 may be indirectly engaged with each other to lock the diluent container 5 at the liquid retaining position.

Figure 8:
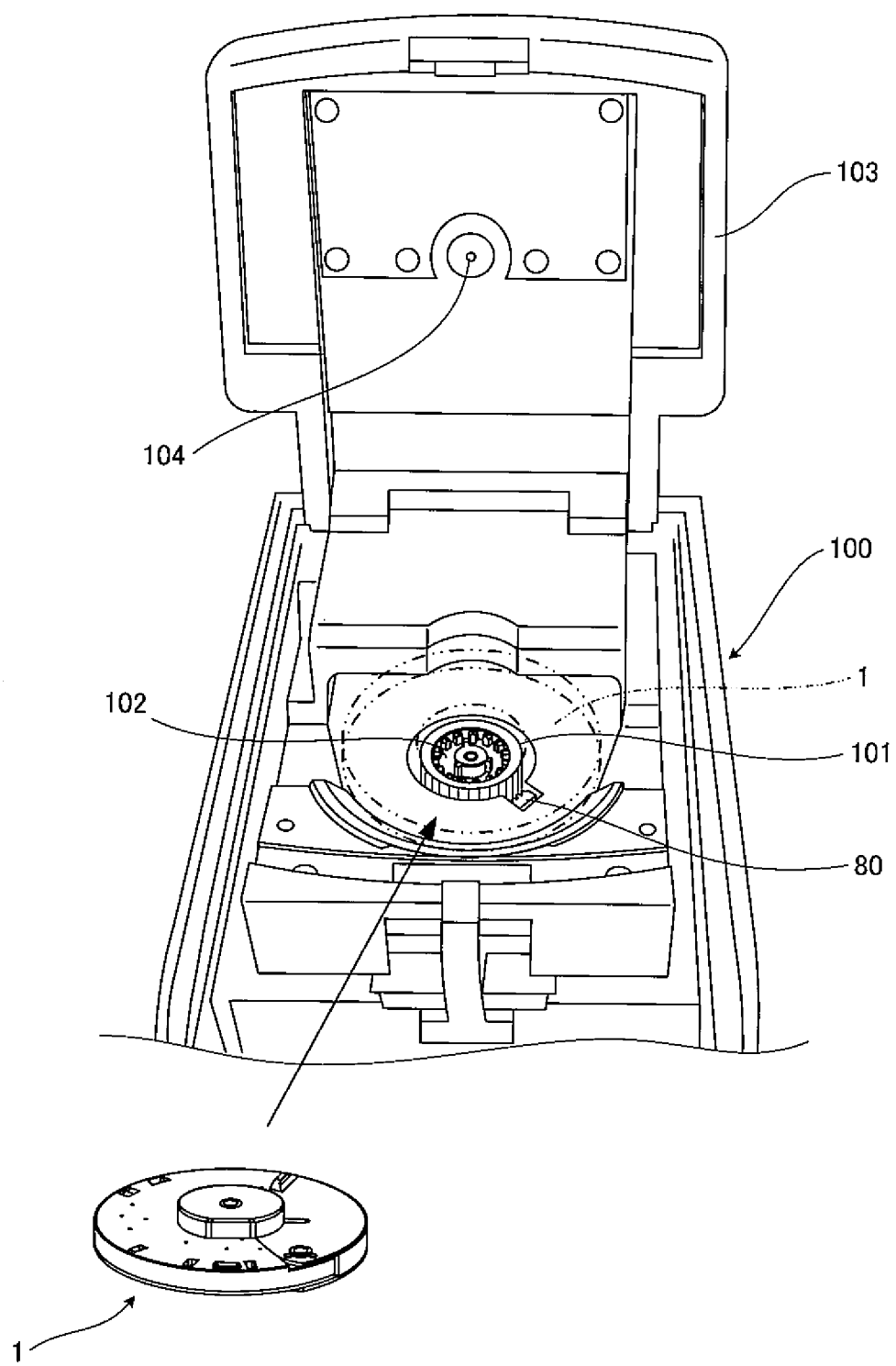
FIG. 8 is a perspective view showing the opened door of an analyzing apparatus according to the first embodiment.
Figure 9:
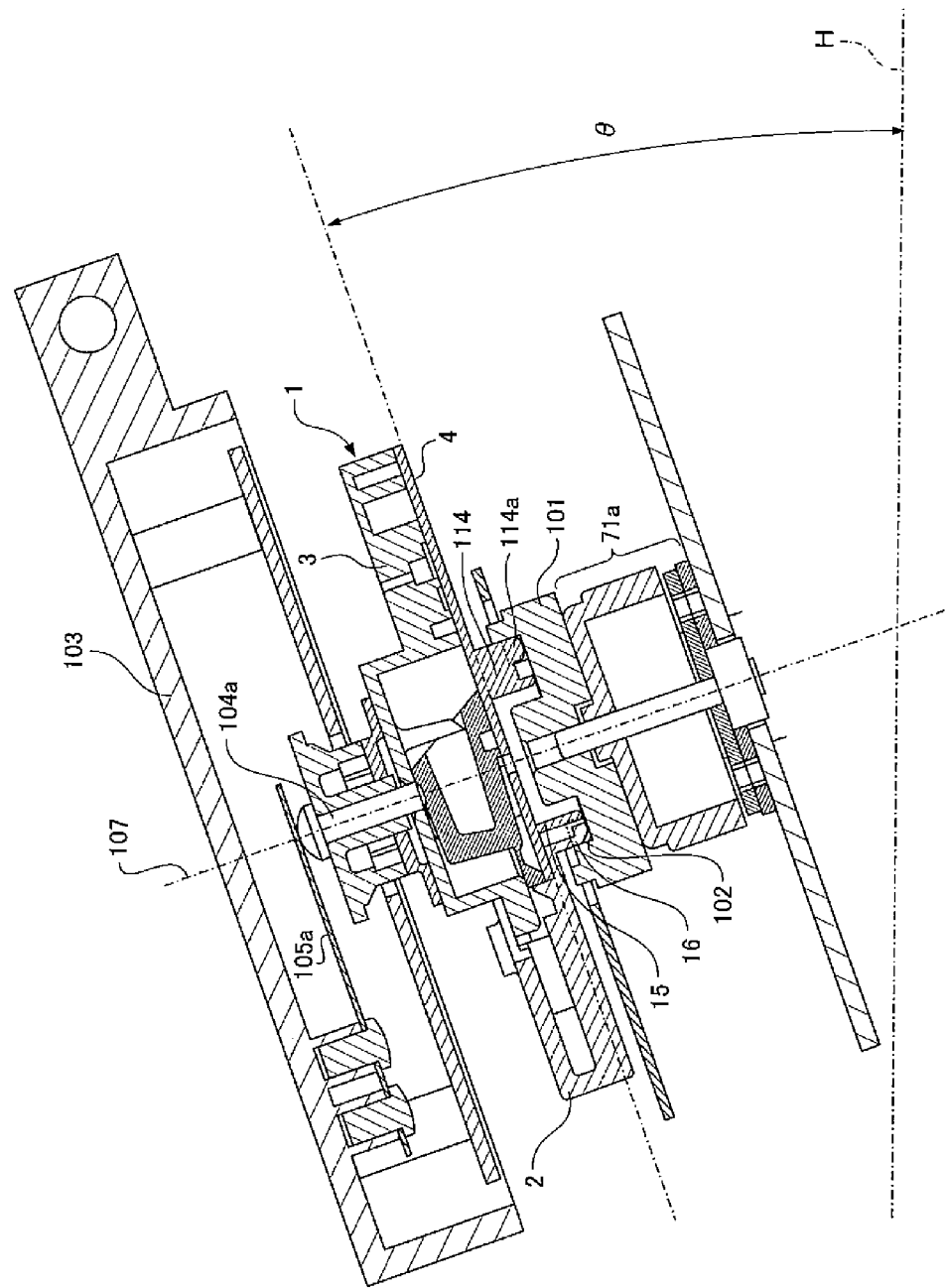
FIG. 9 is a sectional view showing the analyzing apparatus according to the first embodiment.

As shown in FIGS. 8 and 9, the analyzing device 1 is set on a turntable 101 of an analyzing apparatus 100.

In the present embodiment, the turntable 101 is attached around a rotation axis 107 tilted as shown in FIG. 9 and is tilted by angle θ with respect to horizontal line H. The direction of gravity to a solution in the analyzing device 1 can be controlled according to the rotation stop position of the analyzing device 1.

Figure 32:
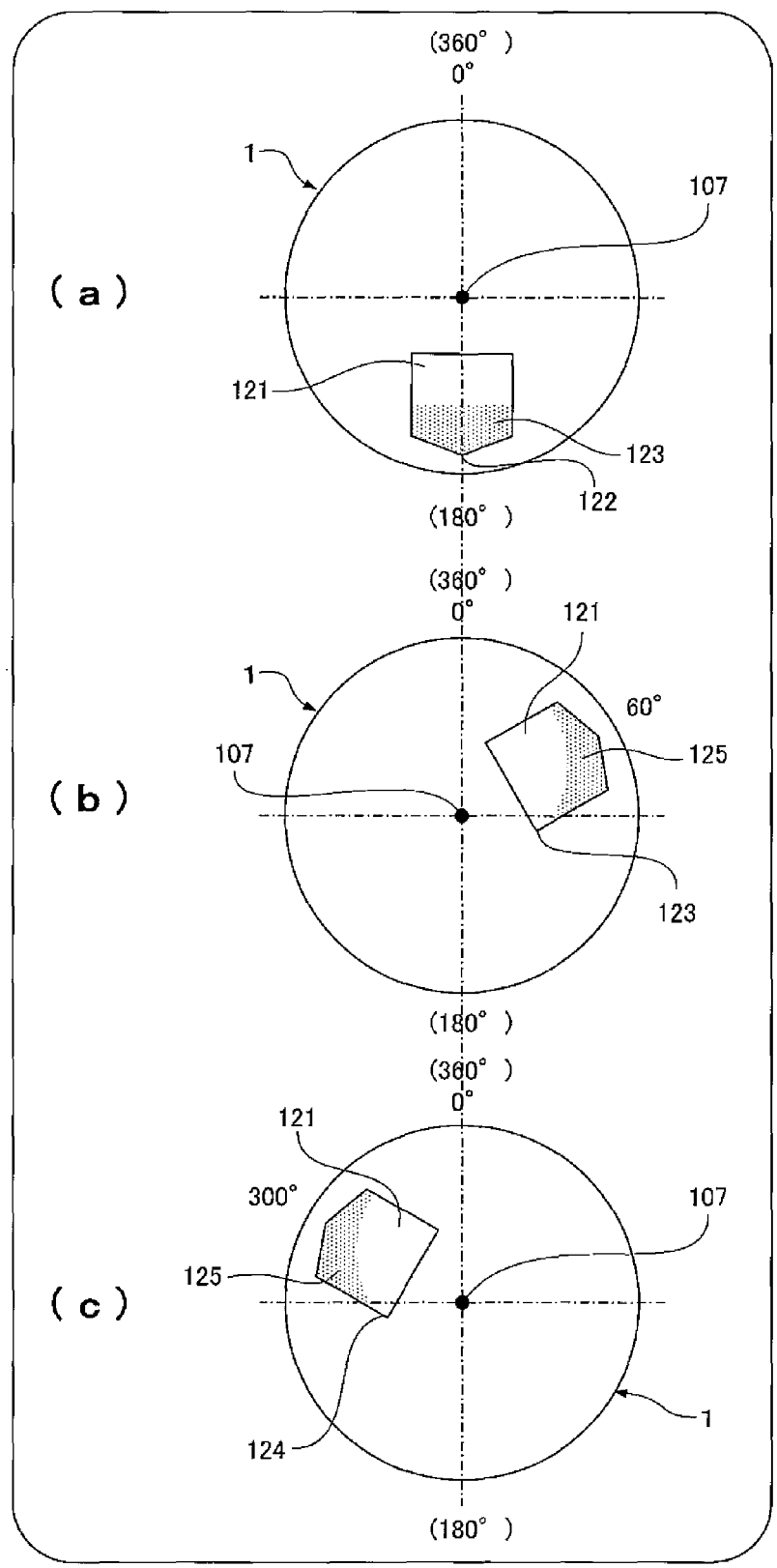
FIG. 32 shows a plan view of the analyzing device when the turntable is stopped around 180° and a plan view of the analyzing device when the turntable is stopped around 60° and 300°.

To be specific, when the analyzing device 1 is stopped at the position of FIG. 32(*a*) (a position around 180° when a position directly above the analyzing device 1 in FIG. 32(*a*) is 0° (360°)), an underside 122 of an operation cavity 121 is directed downward when viewed from the front. Thus a force of gravity is applied to a solution 125 in the operation cavity 121 toward the outer periphery (underside 122) of the analyzing device 1.

When the analyzing device 1 is stopped at a position around 60° as shown in FIG. 32(*b*), an upper left side 123 of the operation cavity 121 is directed downward when viewed from the front. Thus a force of gravity is applied to the upper left of the solution 125 in the operation cavity 121. Similarly, at a position around 300° in FIG. 32(*c*), an upper right 124 of the operation cavity 121 is directed downward when viewed from the front. Thus a force of gravity is applied to the upper right of the solution 125 in the operation cavity 121.

In this way, the rotation axis 107 is tilted and the analyzing device 1 is stopped at any position, so that a solution is driven to be transferred in the analyzing device 1 in a predetermined direction.

A force of gravity to a solution in the analyzing device 1 can be set by adjusting the angle θ of the rotation axis. It is desirable to set a force of gravity depending on the relationship between a quantity of transferred liquid and the adhesion of applied liquid on a wall surface in the analyzing device 1.

The angle θ is desirably set at 10° to 45°. When the angle θ is smaller than 10°, a force of gravity applied to the solution is so small that a driving force for transfer may not be obtained. When the angle θ is larger than 45°, a load applied to the rotation axis 107 may increase or the solution transferred by a centrifugal force may unexpectedly move under its own weight, resulting in an uncontrollable state.

On the top surface of the turntable 101, a circular groove 102 is formed. In a state in which the analyzing device 1 is set on the turntable 101, the rotary support section 15 formed on the cover substrate 4 of the analyzing device 1 and the rotary support section 16 formed on the protective cap 2 are engaged with the circular groove 102, so that the analyzing device 1 is accommodated.

After the analyzing device 1 is set on the turntable 101, a door 103 of the analyzing apparatus is closed before a rotation of the turntable 101, so that the set analyzing device 1 is pressed to the turntable 101 by a clamper 104 provided on the door 103, at a position on the rotation axis of the turntable 101 by a biasing force of a spring 105*a* that serves as an urging member. The analyzing device 1 rotates with the turntable 101 that is rotationally driven by a rotational drive unit 106. Reference numeral 107 denotes the rotation axis of the turntable 101.

Figure 10:
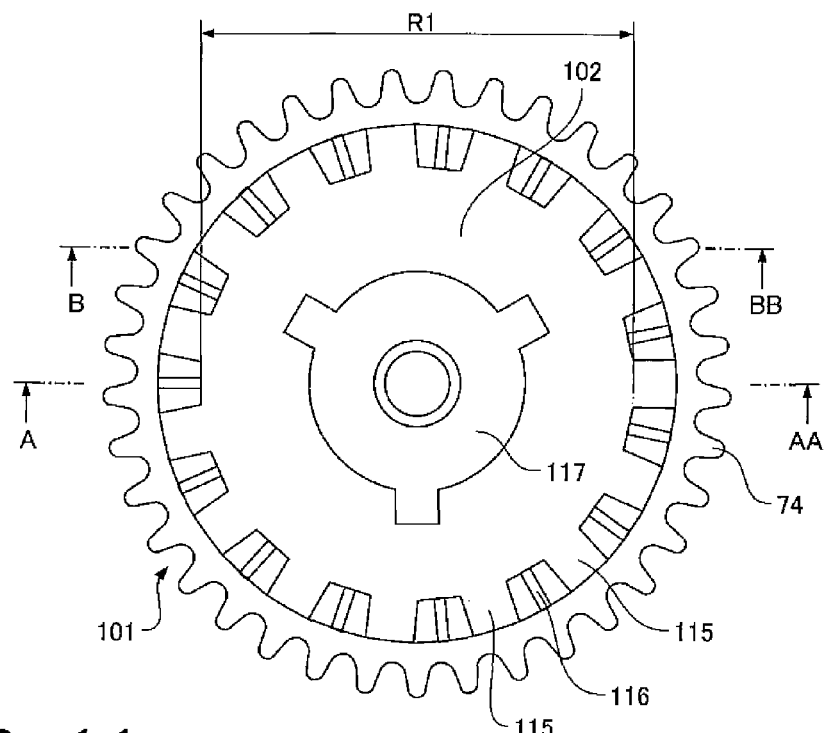
FIG. 10 is an enlarged plan view showing a turntable according to the first embodiment.
Figure 11:
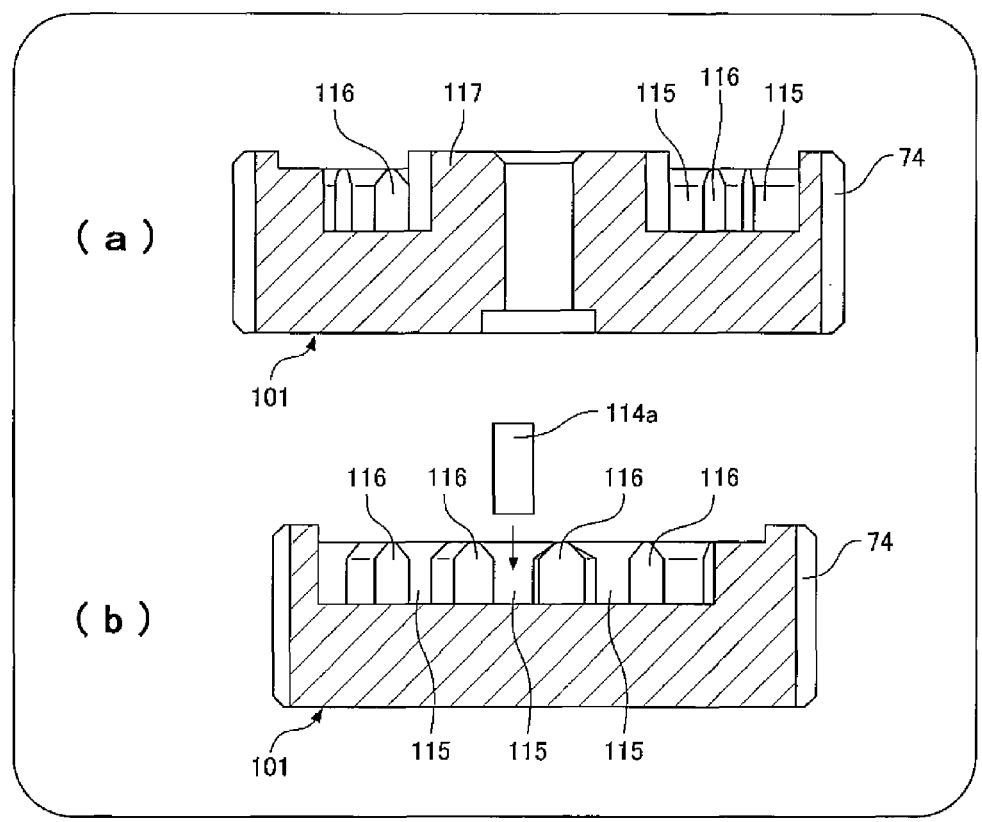
FIG. 11 shows an A-AA sectional view and a B-BB sectional view of the turntable according to the first embodiment.

As shown in FIGS. 10 and 11(*a*), on the inner periphery of the circular groove 102 of the turntable 101, a plurality of grooves 115 are provided at regular intervals as detent locking sections on the turntable 101. FIG. 11(*a*) is an A-AA sectional view of FIG. 10 and FIG. 11(*b*) is a B-BB sectional view of FIG. 10. Partitions 116 between the grooves 115 of the turntable 101 have angular tops. Further, an internal diameter R1 of the partitions 116 between the grooves 115 is larger than an external diameter R2 of the rotary support section 15 that is provided at the center of the bottom of the analyzing device 1 and is accommodated in the circular groove 102 of the turntable 101.

With this configuration, when the analyzing device 1 is set on the turntable 101, as shown in FIG. 9, a central projecting section 117 formed as a centering fitting section at the center of the circular groove 102 of the turntable 101 is located inside the rotary support section 15 of the analyzing device 1, and the central projecting section 117 acts as a centering fitting section for centering the analyzing device 1 and the turntable 101. At this point, as shown in FIGS. 9 and 12, an end 114a of the projecting section 114 of the analyzing device 1 is engaged with any one of the grooves 115 formed at regular intervals on the inner periphery of the circular groove 102 of the turntable 101, so that the analyzing device 1 does not slip in the circumferential direction of the turntable 101.

The protective cap 2 is attached to prevent the sample liquid applied around the inlet 13 from being splashed to the outside by a centrifugal force during analysis.

The components constituting the analyzing device 1 are desirably made of resin materials enabling low material cost with high mass productivity. The analyzing apparatus 100 analyzes the sample liquid according to an optical measurement method for measuring light having passed through the analyzing device 1. Thus the base substrate 3 and the cover substrate 4 are desirably made of transparent synthetic resins including PC, PMMA, AS, and MS.

The diluent container 5 is desirably made of crystalline synthetic resins such as PP and PE that have low moisture permeability. This is because the diluent container 5 has to contain the diluent 8 for a long time period. The protective cap 2 may be made of any materials as long as high moldability is obtained. Inexpensive resins such as PP, PE, and ABS are desirable.

The base substrate 3 and the cover substrate 4 are desirably joined to each other according to a method hardly affecting the reaction activity of a reagent retained in the storage area. Thus methods such as ultrasonic welding and laser welding are desirable by which a reactive gas and a solvent are hardly generated during joining.

On a part where a solution is transferred by a capillary force in a small clearance between the base substrate 3 and the cover substrate 4 that are joined to each other, hydrophilic treatment is performed to increase the capillary force. To be specific, hydrophilic treatment is performed using a hydrophilic polymer, a surface-active agent, and so on. In this case, hydrophilicity is a state in which a contact angle is less than 90° relative to water. More preferably, the contact angle is less than 40°.

Figure 13:
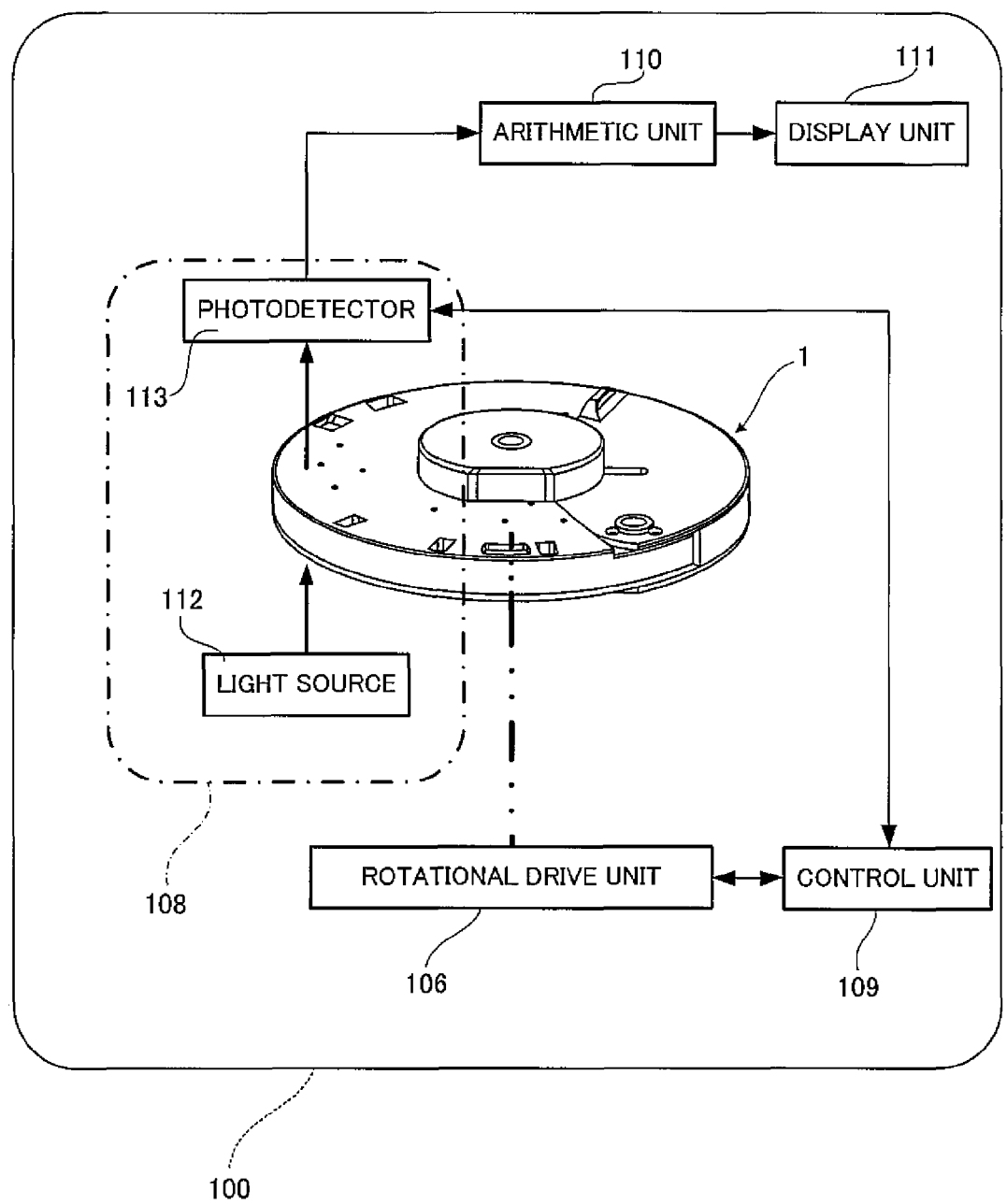
FIG. 13 is a structural diagram of the analyzing apparatus according to the first embodiment.

FIG. 13 shows the configuration of the analyzing apparatus 100.

The analyzing apparatus 100 is made up of the rotational drive unit 106 for rotating the turntable 101, an optical measurement unit 108 for optically measuring a solution in the analyzing device 1, a control unit 109 for controlling, e.g., the rotation speed and direction of the turntable 101 and the measurement timing of the optical measurement unit, an arithmetic unit 110 for calculating a measurement result by processing a signal obtained by the optical measurement unit 108, and a display unit 111 for displaying the result obtained by the arithmetic unit 110.

The rotational drive unit 106 can rotate the analyzing device 1 through the turntable 101 about the rotation axis 107 in any direction at a predetermined rotation speed and can further oscillate the analyzing device 1 such that the analyzing device 1 laterally reciprocates at a predetermined stop position with respect to the rotation axis 107 with a predetermined amplitude range and a predetermined period.

The optical measurement unit 108 includes a light source 112 for emitting light of a specific wavelength to the measurement section of the analyzing device 1, and a photodetector 113 for detecting the quantity of light having passed through the analyzing device 1 out of the light emitted from the light source 112.

The analyzing device 1 is rotationally driven by the turntable 101, and the sample liquid drawn into the analyzing device 1 from the inlet 13 is transferred in the analyzing device 1 by using a centrifugal force generated by rotating the analyzing device 1 about the rotation axis 107 located inside the inlet 13 and the capillary force of a capillary passage provided in the analyzing device 1. The microchannel structure of the analyzing device 1 will be specifically described below along with an analyzing process.

Figure 14:
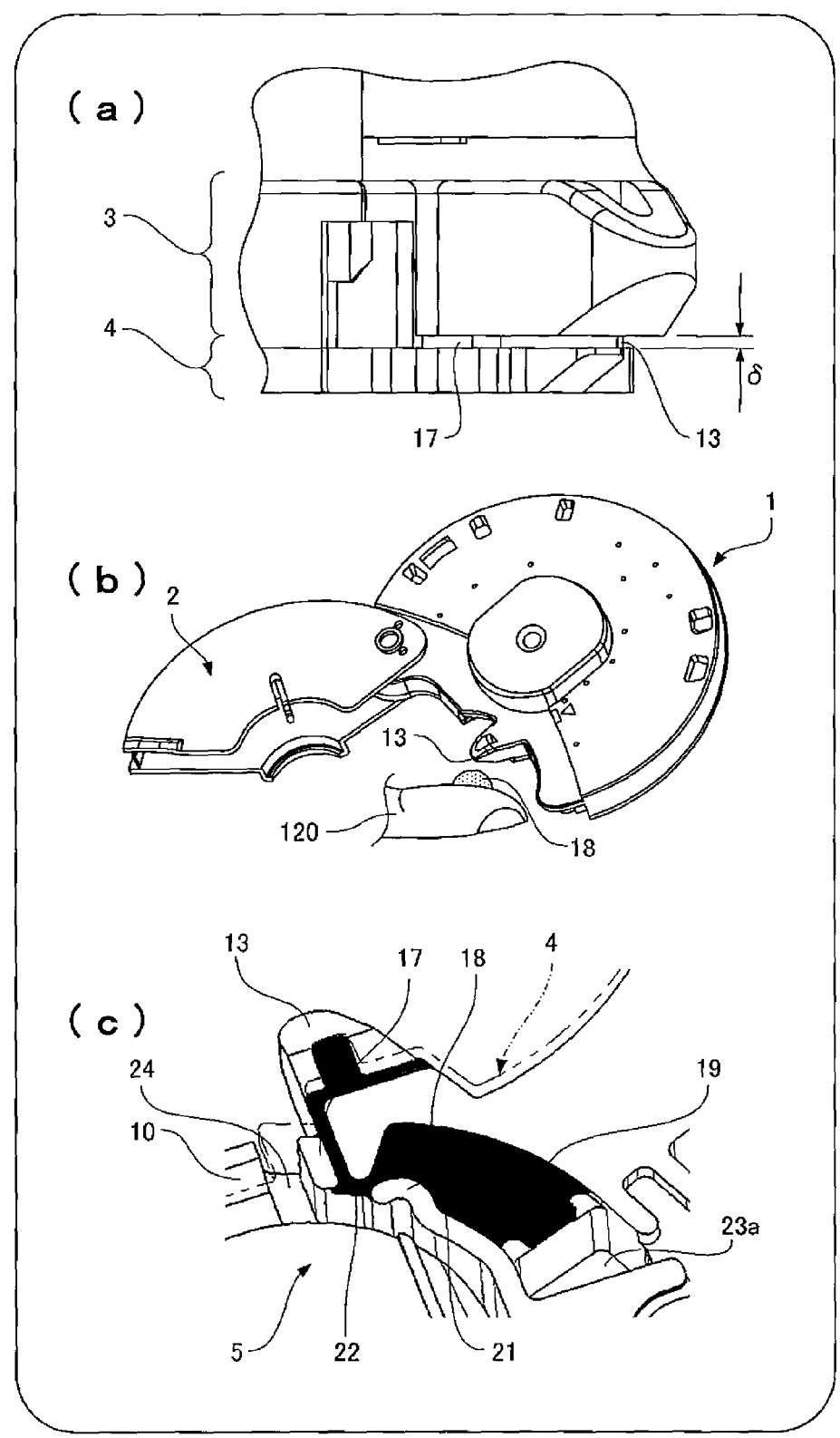
FIG. 14 shows an enlarged perspective view of a portion around the inlet of the analyzing device, a perspective view showing that the protective cap is opened and a sample liquid is collected from a finger tip, and an enlarged perspective view of the microchannel structure of the analyzing device that is viewed from the turntable through a cover substrate.

FIG. 14 shows a part around the inlet 13 of the analyzing device 1.

FIG. 14(a) is an enlarged view of the inlet 13 viewed from the outside of the analyzing device 1. FIG. 14(b) shows that the protective cap 2 is opened and a sample liquid 18 is collected from a fingertip 120. FIG. 14(c) shows the microchannel structure viewed from the turntable 101 through the cover substrate 4.

The inlet 13 projects to the outer periphery of the analyzing device 1 from the rotation axis 107 set in the analyzing device 1 and the inlet 13 is connected to a capillary cavity 19 through a guide section 17 receiving a capillary force with a small clearance δ that is formed between the base substrate 3 and the cover substrate 4 so as to extend to the inner periphery of the analyzing device 1. The capillary cavity 19 can retain a required quantity of the sample liquid 18 by a capillary force. With this configuration, the protective cap 2 is opened and the sample liquid 18 is directly applied into the inlet 13, so that the sample liquid applied around the inlet 13 is drawn into the analyzing device 1 by the capillary force of the guide section 17.

On the guide section 17, the capillary cavity 19, and the connected section, a bending section 22 is formed that changes the direction of a passage with a recessed section 21 formed on the base substrate 3.

When viewed from the guide section 17, a receiving cavity 23a is formed behind the capillary cavity 19 such that the receiving cavity 23a has a clearance in which a capillary force is not applied. Partially on the sides of the capillary cavity 19, the bending section 22, and the guide section 17, a cavity 24 is formed that has one end connected to a separating cavity 23 and the other end opened to the atmosphere. By the effect of the cavity 24, the sample liquid collected from the inlet 13 passes through the guide section 17 and preferentially flows along the side walls of the capillary cavity 19 so as to avoid the cavity 24. Thus when air bubbles are entrained at the inlet 13, the air is discharged to the cavity 24 in a section where the guide section 17 is adjacent to the cavity 24, so that the sample liquid 18 can be collected without entraining air bubbles.

Figure 15:
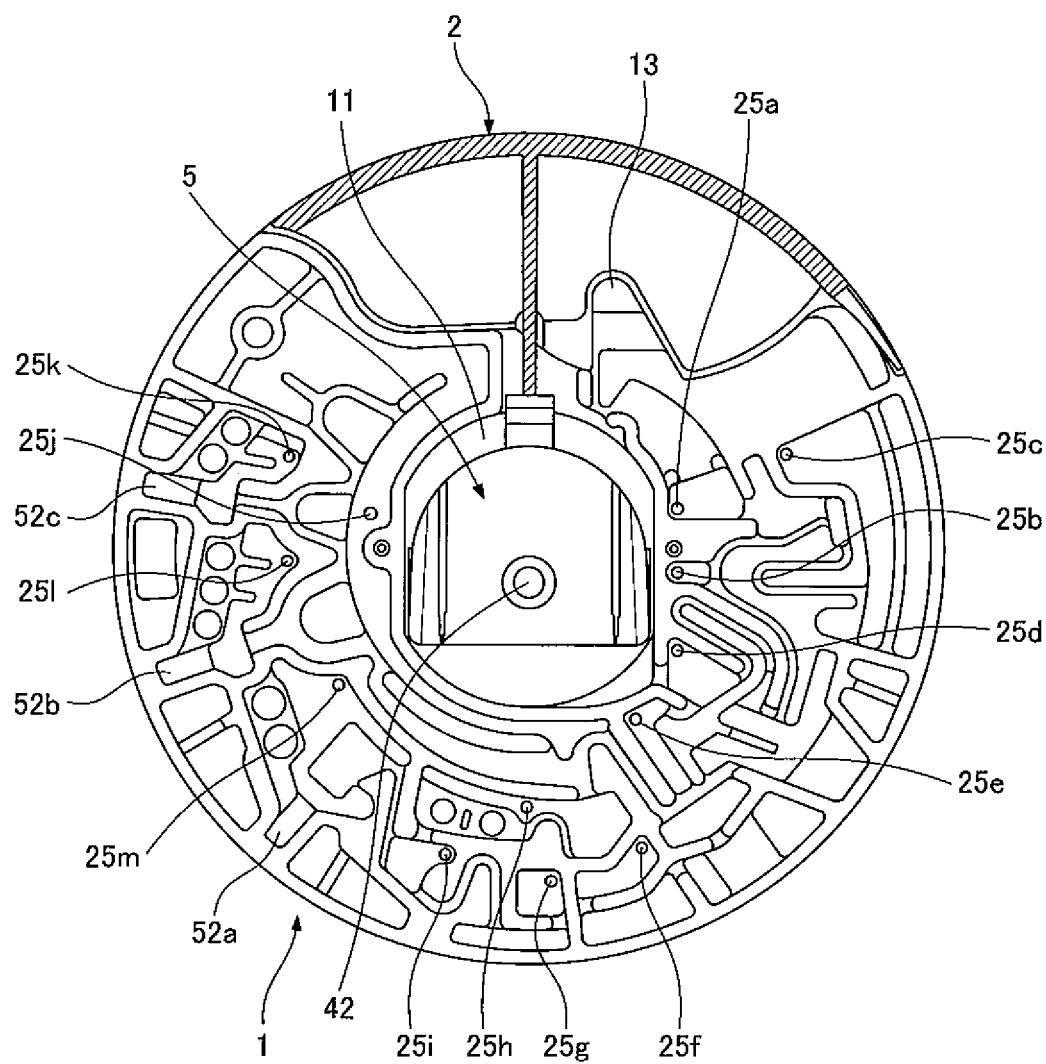
FIG. 15 is a state diagram showing a state before the analyzing device containing the dropped sample liquid is set on the turntable according to the first embodiment.

FIG. 15 shows a state before the analyzing device 1 containing the dropped sample liquid 18 is set on the turntable 101 and is rotated thereon. At this point, as shown in FIG. 6(c), the aluminum seal 9 of the diluent container 5 has been collided with and broken by the opening rib 11a. Reference characters 25a to 25m denote air holes formed on the base substrate 3.

As shown in FIG. 16, at a point of an overflow cavity for transferring a liquid in a direction (arrow K), along which a centrifugal force is obtained, from the rotation axis 107 to the outer periphery of the analyzing device 1, a capillary passage 37 for circumferentially transferring a liquid from an upstream process to a downstream process is provided across the overflow cavity. The liquid is discharged over the capillary passage 37 by the centrifugal force. To be specific, a reserving cavity 27 and a mixing cavity 39 are disposed in the circumferential direction (arrow K) from the center to the outer periphery of the analyzing device 1. On the sides of the reserving cavity 27 and the mixing cavity 39, overflow cavities 29a and 29b and a chamber 29c are disposed in the circumferential direction. Between the overflow cavities 29a and 29b, the capillary passage 37 is formed across the flowing direction of an excessive diluent supplied to the chamber 29c.

The analyzing device 1 further includes a sealing overflow cavity 29d between an atmospheric-side overflow cavity 29e communicating with the atmosphere and the chamber 29c. The sealing overflow cavity 29d communicates with the chamber 29c via a first overflow passage 28c and communicates with the atmospheric-side overflow cavity 29e via a second overflow passage 28d.

The following will describe the analyzing process along with the configuration of the control unit 109 that controls the operation of the rotational drive unit 106.

Step 1

As shown in FIG. 16(a), the analyzing device 1 in which a sample liquid to be inspected has been dropped into the inlet 13 is set on the turntable 101 in a state in which the sample liquid is retained in the capillary cavity 19 and the aluminum seal 9 of the diluent container 5 has been broken.

Step 2

The door 103 is closed and then the turntable 101 is rotationally driven in a clockwise direction (direction C2), so that the retained sample liquid overflows at the position of the bending section 22. The sample liquid in the guide section 17 is discharged to the protective cap 2, and then as shown in FIG. 16(b), the sample liquid 18 in the capillary cavity 19 flows into separating cavities 23b and 23c through the receiving cavity 23a and is centrifugally separated into a plasma component 18a and a blood cell component 18b by the separating cavities 23b and 23c.

As shown in FIGS. 16(b) and 23(a), the diluent 8 from the diluent container 5 flows into the reserving cavity 27 through a discharging passage 26. When the diluent 8 having flowed into the reserving cavity 27 exceeds a predetermined quantity, an excessive quantity of the diluent 8 flows into the overflow cavity 29a through an overflow passage 28a, passes over the capillary passage 37, and flows into the chamber 29c, which serves as a reference measuring chamber, through the overflow cavity 29b and an overflow passage 28b.

As in the reserving cavity 27, when the diluent having flowed into the chamber 29c exceeds a predetermined quantity, an excessive quantity of the diluent flows into the sealing overflow cavity 29d, which serves as a blocking overflow cavity, through the first overflow passage 28c serving as a reference-side overflow passage.

Figure 17:
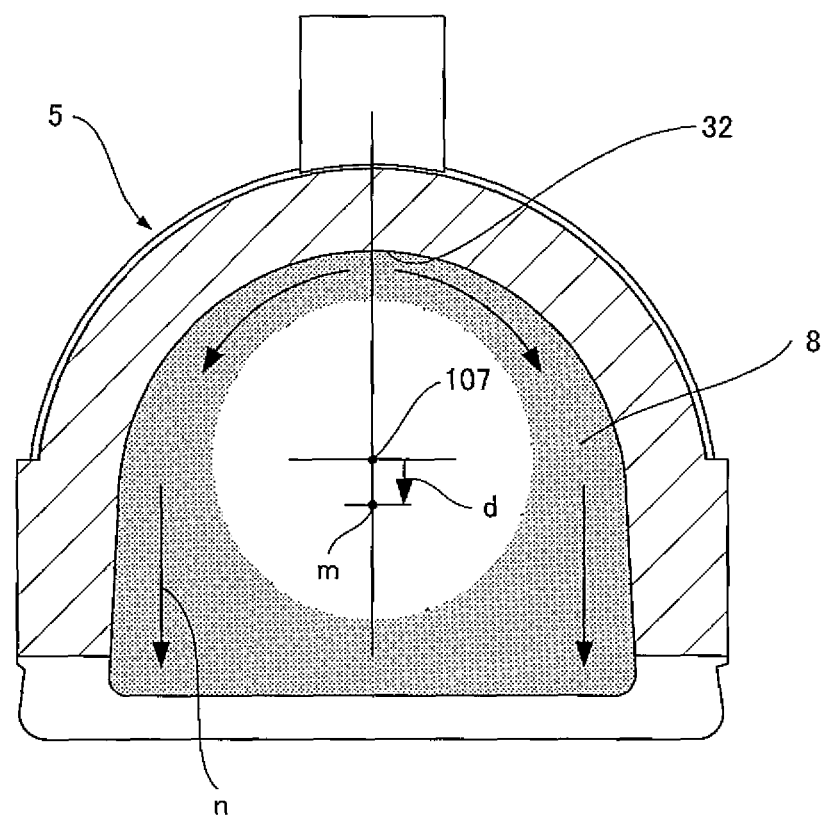
FIG. 17 is an enlarged sectional view for explaining the discharge of a liquid from the diluent container according to the first embodiment.

As shown in FIGS. 4(a) and 4(b), the bottom of the diluent container 5 on the opposite side from the opening 7 sealed with the aluminum seal 9 is formed of a curved surface 32. At the liquid discharging position of the diluent container 5 in the state of FIG. 16(b), a center m of the curved surface 32 is offset, as shown in FIG. 17, by a distance d from the rotation axis 107 to the discharging passage 26. The flow of the diluent 8 to the curved surface 32 is changed to a flow (arrow n) from the outside to the opening 7 along the curved surface 32, and then the diluent 8 is efficiently discharged to the diluent container storage part 11 from the opening 7 of the diluent container 5.

Step 3

Next, when the rotation of the turntable 101 is stopped, the plasma component 18a is sucked into a capillary cavity 33 formed on the wall surface of the separating cavity 23b and flows, as shown in FIG. 18(a), into a measuring passage 38 through a connecting passage 30 communicating with the capillary cavity 33, so that a fixed quantity of the plasma component 18a is retained.

In the present embodiment, a filling confirming area 38a is formed at the outlet of the measuring passage 38 so as to extend to the inner periphery of the analyzing device 1. Before advancing to the subsequent process, the analyzing device 1 is slowly rotated at around 100 rpm and the presence or absence of the plasma component 18a can be optically detected in a state in which the filling confirming area 38a retains the plasma component 18a. The filling confirming area 38a in the analyzing device 1 has a rough inner surface that scatters light passing through the filling confirming area 38a. When the filling confirming area 38a is not filled with the plasma component 18a, the quantity of transmitted light decreases. When the filling confirming area 38a is filled with the plasma component 18a, the liquid is also applied to the minutely uneven surface. Thus the scattering of light is suppressed and the quantity of transmitted light increases. The presence or absence of the plasma component 18a can be detected by detecting a difference in light quantity.

The sample liquid in the separating cavities 23b and 23c is sucked into a connecting passage 34 that is siphon-shaped and connects the separating cavity 23c and an overflow cavity 36b. The diluent 8 is similarly sucked into a connecting passage 41 that is siphon-shaped and connects the reserving cavity 27 and the mixing cavity 39.

In this configuration, a flow preventing groove 32a at the outlet of the connecting passage 41 is formed to prevent the diluent 8 from flowing from the connecting passage 41 to the measuring passage 38. The flow preventing groove 32a is formed with a thickness of about 0.2 mm to 0.5 mm on the base substrate 3 and the cover substrate 4.

The capillary cavity 33 is formed from the outermost position of the separating cavity 23b to the inner periphery of the analyzing device 1. In other words, the outermost position of the capillary cavity 33 is extended outside a separation interface 18c of the plasma component 18a and the blood cell component 18b in FIG. 16(b).

By setting the position of the outer periphery of the capillary cavity 33 thus, the outer end of the capillary cavity 33 is immersed in the plasma component 18a and the blood cell component 18b that have been separated in the separating cavity 23b. Since the plasma component 18a has a lower viscosity than the blood cell component 18b, the plasma component 18a is preferentially sucked by the capillary cavity 33. The plasma component 18a can be transferred to the measuring passage 38 through the connecting passage 30.

After the plasma component 18a is sucked, the blood cell component 18b is also sucked following the diluted plasma component 18a. Thus the plasma component 18a can be replaced with the blood cell component 18b in the capillary cavity 33 and a path halfway to the connecting passage 30. When the measuring passage 38 is filled with the plasma component 18a, the transfer of the liquid is stopped also in the connecting passage 30 and the capillary cavity 33, so that the blood cell component 18b does not enter the measuring passage 38.

Hence, it is possible to minimize a loss of the transferred liquid as compared with the configuration of the related art, thereby reducing a quantity of the sample liquid required for measurement.

FIG. 24 shows an enlarged view of the connecting passage 34 and a part around the connecting passage 34, which will be specifically described below.

In the related art, in order to prevent the sample liquid remaining in the separating cavities 23b and 23c from being sucked into the capillary cavity 33 and transferred to the subsequent process as shown in FIG. 24(a), the connecting passage 34 is provided that is siphon-shaped, is connected to the outermost position (r1) of the separating cavity 23c, and has a radial position (r2) at the outlet where r1<r2 is established. After the sample liquid is sucked into the connecting passage 34, the turntable 101 is rotated to discharge the sample liquid remaining in the separating cavities 23b and 23c to the overflow cavity 36b by a siphon action. However, when the sample liquid is blood, the blood cell component 18b passing through the connecting passage 34 is varied in transport speed among individuals. Thus it is necessary to start a rotation in the subsequent process in consideration of a time period until the blood cell component 18b reaches the outlet of the connecting passage 34. It has been found that the blood cell component 18b having early reached the outlet of the connecting passage 34 is clotted during a standby time before the subsequent process and then the blood cell component 18b clogs at the outlet of the connecting passage 34 and cannot be discharged at the start of the rotation in the subsequent process. In order to avoid this phenomenon, the position (r2) at the outlet of the connecting passage 34 may be further extended to the outer periphery of the analyzing device 1 to prevent the blood cell component 18b from reaching the outlet of the connecting passage 34 and suppress the clotting of the blood cell component 18b. However, this configuration is not suitable for the size reduction of the analyzing device 1.

In the present embodiment, as shown in FIG. 24(b), a liquid retaining section 34a is provided from the outlet of the connecting passage 34 in the circumferential direction and to the inner periphery of the analyzing device 1. By providing the liquid retaining section 34a thus, the blood cell component 18b at the outlet of the connecting passage 34 flows into the liquid retaining section 34a. Thus the transfer of the blood cell component 18b is not stopped at the outlet of the connecting passage 34.

Since the width (w2) of the liquid retaining section 34a is larger than the width (w1) of the connecting passage 34, a surface tension is not applied in one direction on the liquid end of the blood cell component 18b, distributing a driving force. The blood cell component 18b decreases in transport speed after flowing into the liquid retaining section 34a, so that variations in transport speed among individuals can be absorbed with a small area.

As shown in FIG. 24(c), a liquid retaining connecting passage 34b may be provided from the outlet of the connecting passage 34 to the inner periphery of the analyzing device 1. Provided at the outlet of the liquid retaining connecting passage 34b are an opened-to-atmosphere cavity 31a and an air hole 25n communicating with the atmosphere in the cavity 31a.

This configuration can achieve the same effect as the configuration of FIG. 24(b).

Step 4

When the turntable 101 is rotationally driven in the clockwise direction (direction C2), as shown in FIG. 18(b), the plasma component 18a retained in the measuring passage 38 overflows at the position of the opened-to-atmosphere cavity 31 and only a fixed quantity of the plasma component 18a flows into the mixing cavity 39. The diluent 8 in the reserving cavity 27 also flows into the mixing cavity 39 through the siphon-shaped connecting passage 41.

The sample liquid 18 in the separating cavities 23b and 23c, the connecting passage 30, and the capillary cavity 33 flows into an overflow cavity 36a through the siphon-shaped connecting passage 34 and a backflow preventing passage 35.

Step 5

Next, the rotation of the turntable 101 is stopped, the analyzing device 1 is set at the position of FIG. 18(b), and the turntable 101 is controlled at a frequency of 40 Hz to 80 Hz so as to oscillate the analyzing device 1 by about ±1 mm, thereby agitating the diluent 8 transferred into the mixing cavity 39 and diluted plasma 40 to be measured, the diluted plasma 40 containing the plasma component 18a.

Step 6

After that, the analyzing device 1 is set at the position of FIG. 19(a), the turntable 101 is controlled at a frequency of 80 Hz to 200 Hz so as to oscillate the analyzing device 1 by about ±1 mm, and the diluted plasma 40 retained in the mixing cavity 39 is transferred to the inlet of the capillary passage 37 formed inside the liquid level of the diluted plasma 40. FIG. 37(a) is a perspective view showing a part around the inlet of the capillary passage 37 from the mixing cavity 39.

The diluted plasma 40 transferred to the inlet of the capillary passage 37 is sucked into the capillary passage 37 by a capillary force and then is sequentially transferred to the capillary passage 37, measuring passages 47a, 47b, and 47c, and an overflow passage 47d.

Referring to FIGS. 25 to 31, the configuration of the mixing cavity 39 and a method of transferring a solution will be specifically described below according to the present embodiment.

FIG. 25(a) is a plan view showing a state of a liquid level in the mixing cavity 39 before oscillation. FIG. 25(b) is a plan view showing a state of the liquid level in the mixing cavity 39 after oscillation. FIG. 25(c) is an A-A sectional view of the mixing cavity 39 shown in FIG. 25(b).

The mixing cavity 39 is formed of an inclined wall surface narrowing from the inner periphery toward the outermost position of the mixing cavity 39. The diluted plasma 40 can be retained at the liquid level (d1) and the capillary passage for transferring the diluted plasma 40 to the subsequent process has an inlet 37a at a position (do) inside the liquid level d1. The mixing cavity 39 operated in the present embodiment can contain about several tens μl. Thus a large surface tension is applied to the wall surface of the mixing cavity 39 and the mixing cavity 39 is hardly affected by a force of gravity.

Figure 25:
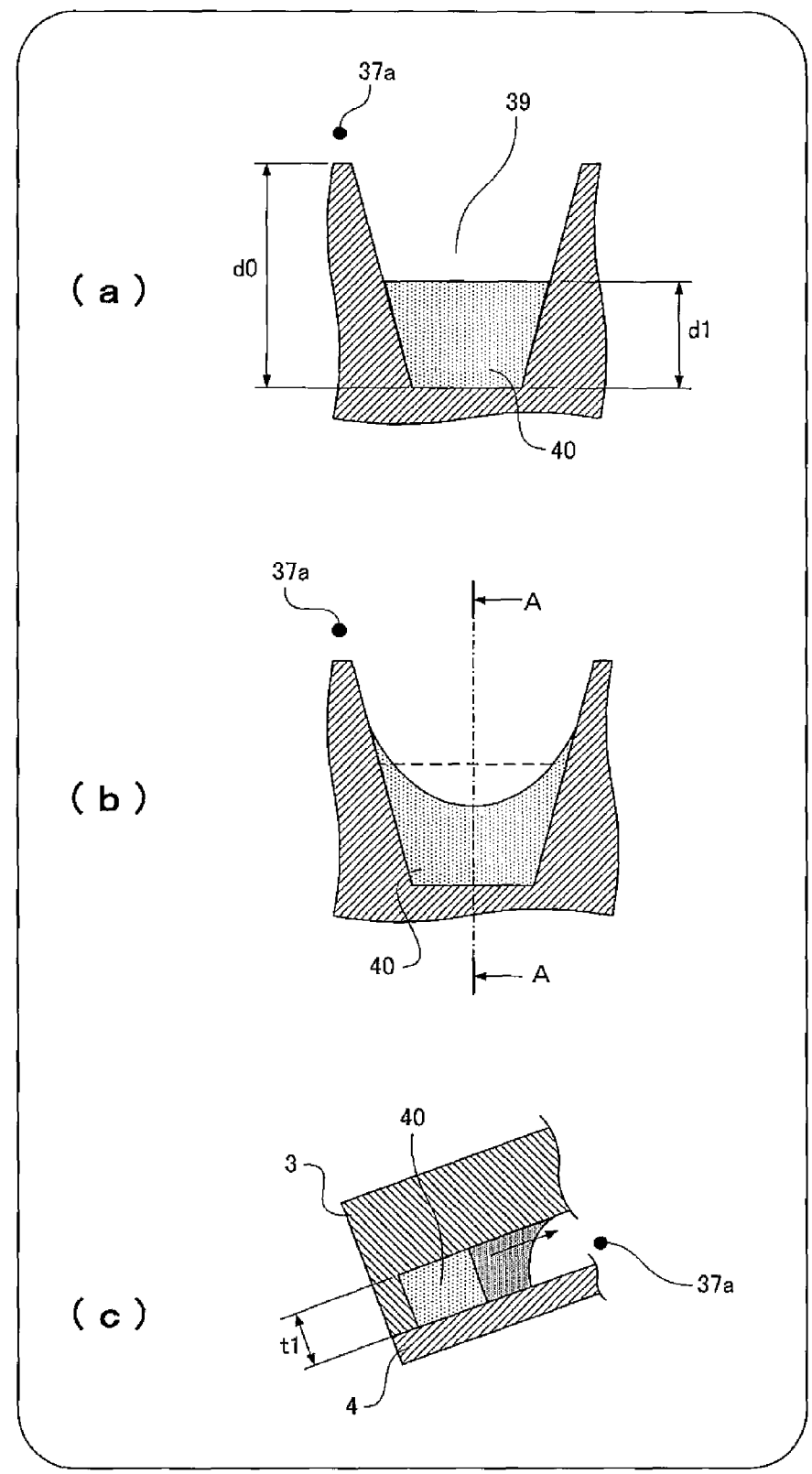
FIG. 25 shows a plan view of a liquid level state of the mixing cavity before oscillation for the explanation of the configuration of the mixing cavity and problems of a transferring method of a solution, a plan view of a liquid level state of the mixing cavity after oscillation, and an A-A sectional view of the mixing cavity.

The following will describe a movement of the diluted plasma 40 retained in the mixing cavity 39 serving as an operation cavity, in the case where the analyzing device 1 is oscillated at the position of the operation cavity 121 shown in FIG. 25(*a*).

As shown in FIG. 25(*b*), the liquid level of the diluted plasma 40 in the mixing cavity 39 is laterally moved by an inertial force of oscillation, so that the diluted plasma 40 forms the liquid level that is pulled to the wall surfaces of the mixing cavity 39.

Therefore, the liquid level pulled to the wall surfaces is increased toward the inner periphery of the mixing cavity by repeatedly oscillating the analyzing device 1, so that the diluted plasma 40 can be transferred to the inlet 37*a* of the capillary passage.

However, in the case where the mixing cavity 39 has a uniform thickness (t1), as shown in FIG. 28(*c*), the liquid level of the diluted plasma 40 increases along the top surface (a surface on the base substrate 3), so that the diluted plasma 40 cannot reach the inlet 37*a* of the capillary passage provided near the bonded interface between the base substrate 3 and the cover substrate 4.

First Example

Figure 26:
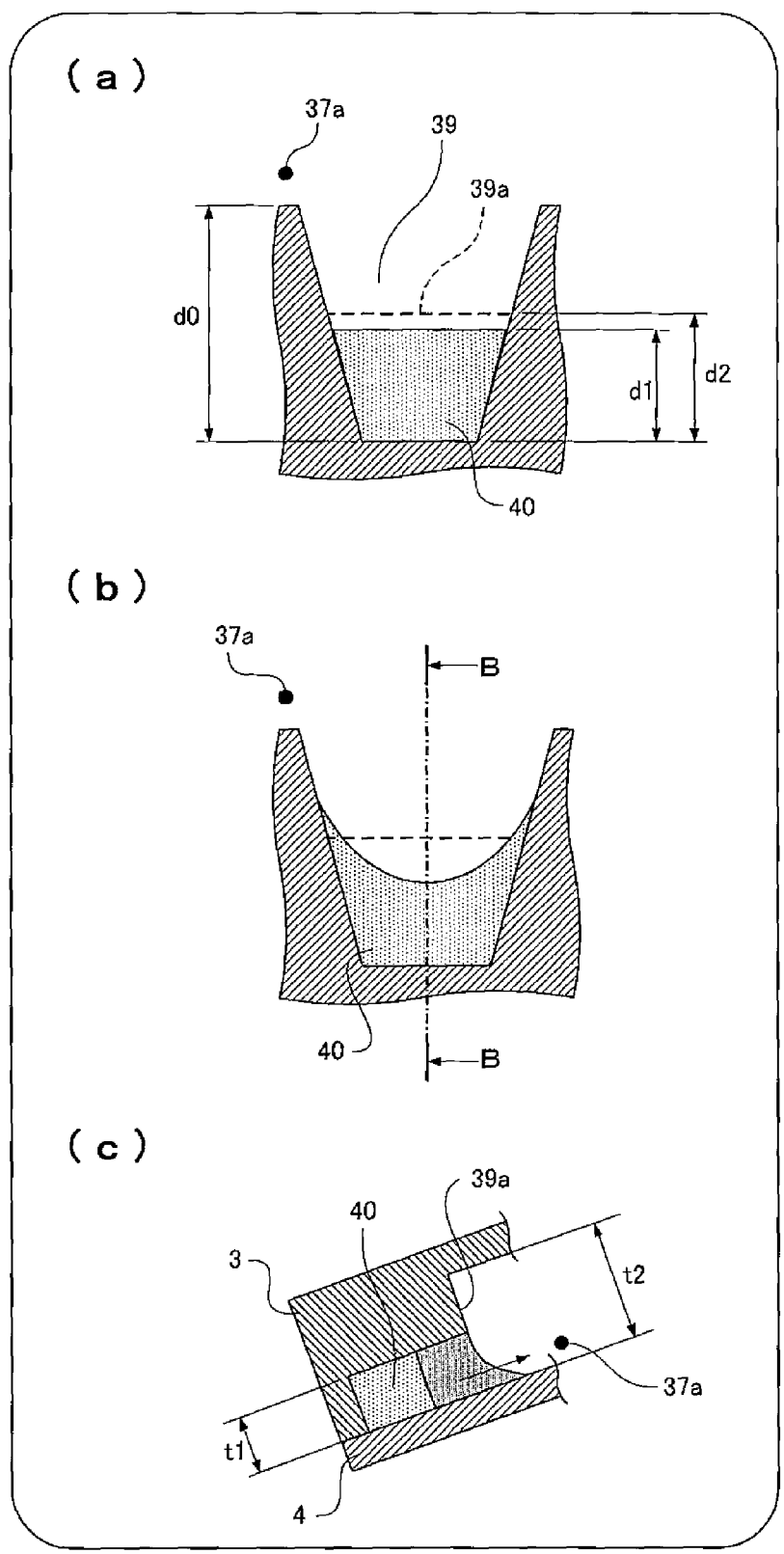
FIG. 26 shows a plan view of a liquid level state of a mixing cavity before the oscillation of an analyzing device according to a first example of the first embodiment, a plan view of a liquid level state of the mixing cavity after oscillation, and a B-B sectional view of the mixing cavity.

Therefore, in the present embodiment, the liquid level is controlled by the configuration of FIG. 26. FIG. 26(*a*) is a plan view showing a state of a liquid level in a mixing cavity 39 before oscillation. FIG. 26(*b*) is a plan view showing a state of the liquid level in the mixing cavity 39 after oscillation. FIG. 26(*c*) is a B-B sectional view of the mixing cavity 39 shown in FIG. 26(*b*).

In the mixing cavity 39, a step 39*a* is formed such that diluted plasma 40 has a larger thickness at an inner position (d2) than the liquid level (d1) of the diluted plasma 40 (t1<t2).

By oscillating this configuration, an increase in liquid level on the wall surfaces of the mixing cavity 39 is suppressed by the step 39*a* provided on the top surface of the mixing cavity 39 and the liquid level on the bottom surface of the mixing cavity 39 is increased to the inner periphery with respect to the step 39*a*. This is because the step 39*a* is provided so as to apply a surface tension in a different direction from the extending direction of the liquid level. Thus the diluted plasma 40 can reach an inlet 37*a* of a capillary passage.

In step 5, however, it is necessary to retain a plasma component 18*a* and a diluent 8 in the mixing cavity 39 and reliably agitate the plasma component 18*a* and the diluent 8 by oscillations. Thus in order to prevent the liquid level from reaching the inlet 37*a* of the capillary passage and prevent the diluted plasma 40 from being sucked into a capillary passage 37 during the oscillations of step 5, it is necessary to provide a sufficient distance between the position of the inlet 37*a* (d0) of the capillary passage and a liquid level position (d1). Particularly, in the case of several tens μl of liquid in the present embodiment, the liquid level can be increased only by a short distance to the inner periphery by oscillations in the configuration of FIG. 26. Thus the liquid level cannot reach the inlet 37*a* of the capillary passage 37 or a sufficient distance cannot be obtained to the inlet 37*a* of the capillary passage, so that the diluted plasma 40 may be sucked into the capillary passage 37 during agitation.

Second Example

Figure 27:
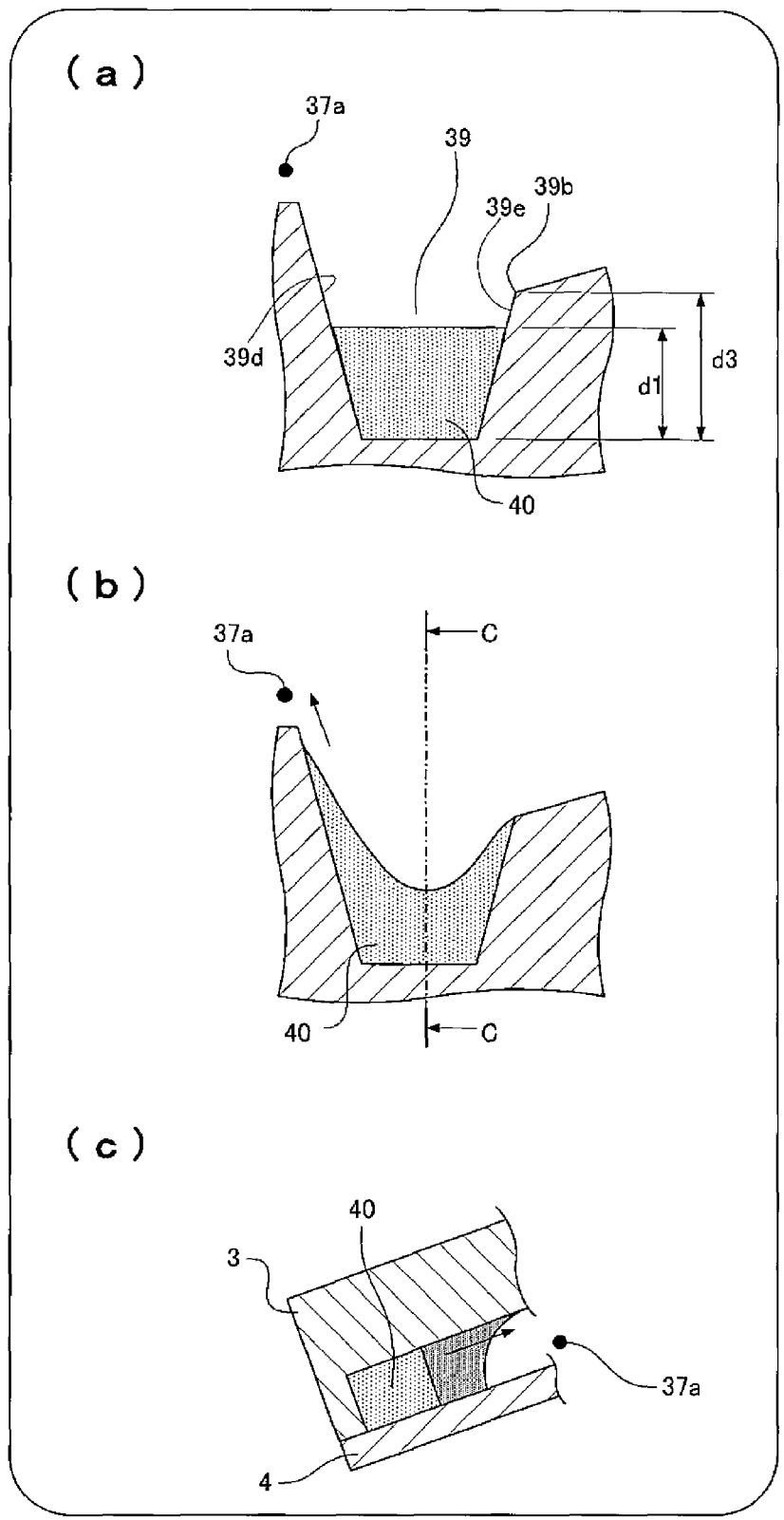
FIG. 27 shows a plan view of a liquid level state of a mixing cavity before the oscillation of an analyzing device according to a second example of the first embodiment, a plan view of a liquid level state of the mixing cavity after oscillation, and a C-C sectional view of the mixing cavity.

Referring to FIG. 27, the following will describe a configuration for increasing the extended distance of a liquid level only on one side of a mixing cavity 39 by oscillation.

FIG. 27(*a*) is a plan view showing a state of a liquid level in the mixing cavity 39 before oscillation. FIG. 27(*b*) is a plan view showing a state of the liquid level in the mixing cavity 39 after oscillations. FIG. 27(*c*) is a C-C sectional view of the mixing cavity 39 shown in FIG. 27(*b*).

The mixing cavity 39 has a bending section 39*b* at a position (d3) inside the liquid level (d1) of diluted plasma 40, on a side wall 39*e* opposed to a side wall 39*d* on which an inlet 37*a* of a capillary passage is provided. The bending section 39*b* opens the mixing cavity 39 toward the inner periphery.

By oscillating this configuration, on the side wall 39*e* opposed to the side wall 39*d* on which the inlet 37*a* of the capillary passage of the mixing cavity 39 is provided, an increase in the liquid level is suppressed by the bending section 39*b* provided on the wall surface, whereas the liquid level is further increased to the inner periphery on the wall surface on which the inlet 37*a* of the capillary passage is provided. This is because the bending section 39*b* is provided to apply a surface tension in a different direction from the extending direction of the liquid level. Thus even when the inlet 37*a* of the capillary passage is sufficiently separated, the liquid level can reach the inlet 37*a*.

Third Example

In FIG. 28, the configurations of FIG. 26 and FIG. 27 are combined to control a liquid level. The liquid level in the configuration of FIG. 26 moves as illustrated in FIGS. 26 and 27.

Fourth Example

Figure 29:
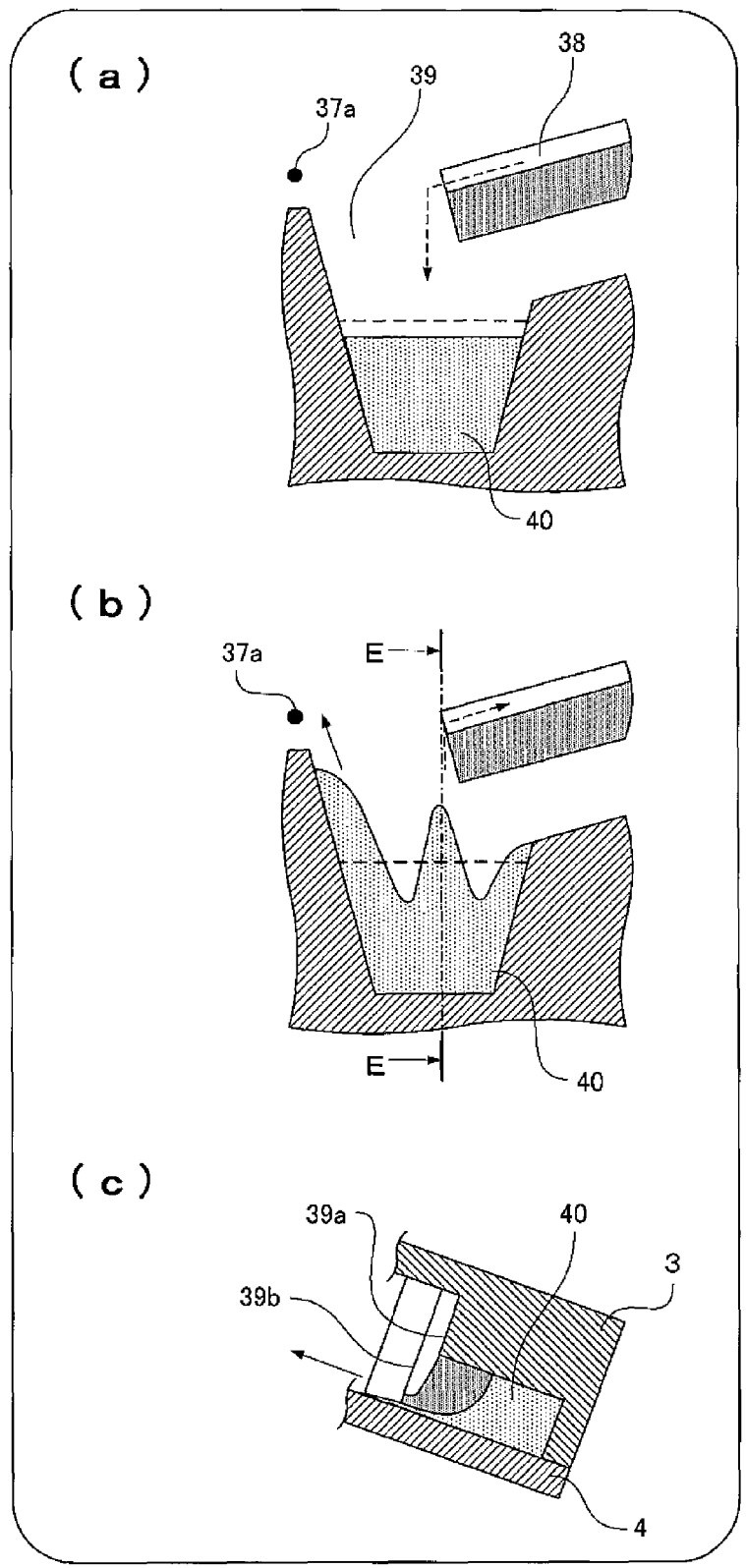
FIG. 29 shows a plan view of a liquid level state of the mixing cavity before oscillation, for the explanation of problems of the size reduction of the analyzing device, a plan view showing a liquid level state of the mixing cavity after oscillation, and an E-E sectional view of the mixing cavity.

In order to further reduce the size of an analyzing device 1, as shown in FIG. 29(*a*), the outlet of a measuring passage 38 may be formed near the liquid level of diluted plasma 40 retained in a mixing cavity 39.

A plasma component 18*a* retained in the measuring passage 38 is transferred to the mixing cavity 39 by a centrifugal force generated by a rotation of the analyzing device 1. At this point, the plasma component 18*a* is transferred while moistening the surface of a cover substrate 4. The surface moistened once decreases in surface tension and thus liquid easily spreads over the surface. Therefore, as shown in FIG. 29(*b*), the oscillated mixing cavity 39 may cause the diluted plasma 40 to spread to a path where the plasma component 18*a* has passed, reach the outlet of the measuring passage 38, and flow backward into the measuring passage 38.

For this reason, in the present embodiment, the liquid level is also controlled by the configuration of FIG. 30.

FIG. 30(*a*) is different from FIG. 29(*a*) in that the cover substrate 4 includes a recessed section (hollow) 39*c*. The recessed section 39*c* is formed inside the liquid level (d1) of the diluted plasma 40 and is formed over a region (around the outlet of the measuring passage 38 and a bending section 39*b*) where the diluted plasma 40 should not spread on the surface of the cover substrate 4. At this point, on a wall surface where an inlet 37*a* of a capillary passage is provided, a region 39*f* is left that has a width w and includes no recessed sections.

With this configuration, even when the mixing cavity 39 is oscillated, the liquid level increasing to a path having been moistened by the transferred plasma component 18*a* can be suppressed by a surface tension applied to the step of the recessed section 39*c*, so that the liquid level of the diluted plasma 40 can reach the inlet 37*a* of the capillary passage.

It is more effective to perform water-repellent finishing with a repellent on the inner surface of the recessed section 39c formed on the cover substrate 4.

Figure 31:
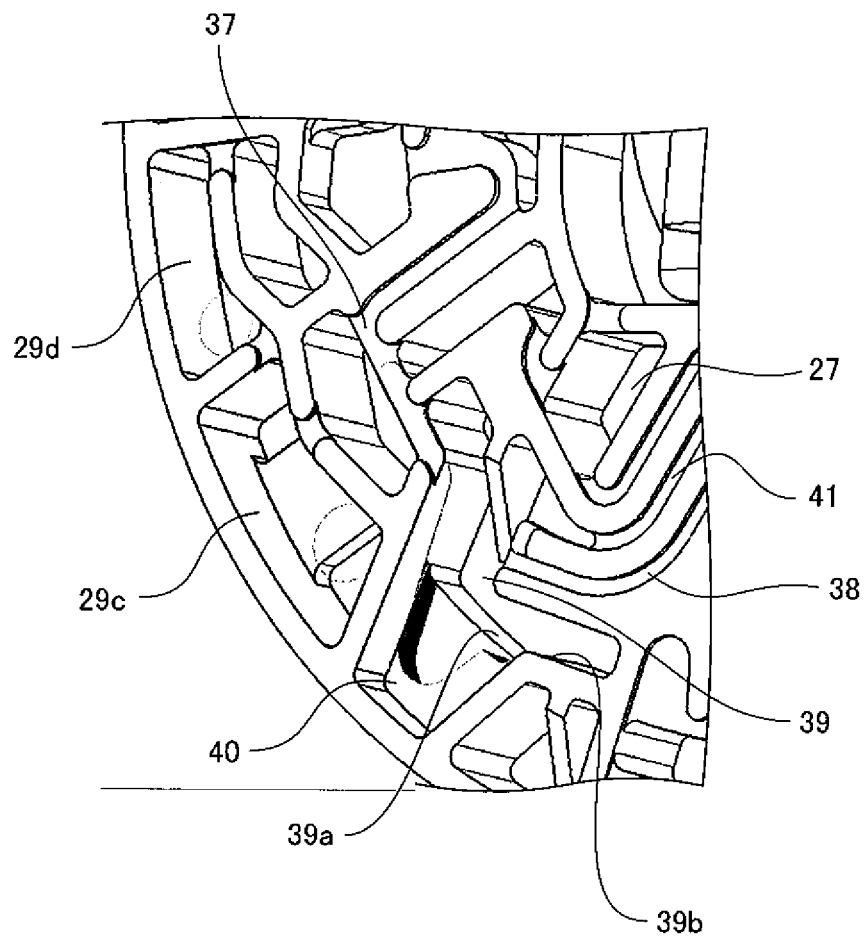
FIG. 31 is an enlarged perspective view showing a liquid level state of the mixing cavity at the start of the suction of diluted plasma from the mixing cavity to a capillary passage according to the fourth example.

FIG. 31 shows a state of the liquid level in the mixing cavity 39 at the start of the suction of the diluted plasma 40 from the mixing cavity 39 into a capillary passage 37.

Oscillations around the position of FIG. 19(a) can efficiently suck the diluted plasma 40 from the mixing cavity 39. Further, in the capillary passage 37, a transport speed is increased by a capillary force and a force of gravity applied to the diluted plasma flowing into the capillary passage 37.

In a time period during which the diluted plasma 40 passes through the capillary passage 37 and reaches measuring passages 47a, 47b, and 47c and an overflow passage 47d, repeated oscillations can suppress a surface tension of the diluted plasma 40 in the mixing cavity 39 with an inertial force of oscillation, thereby further increasing the transport rate.

Figure 33:
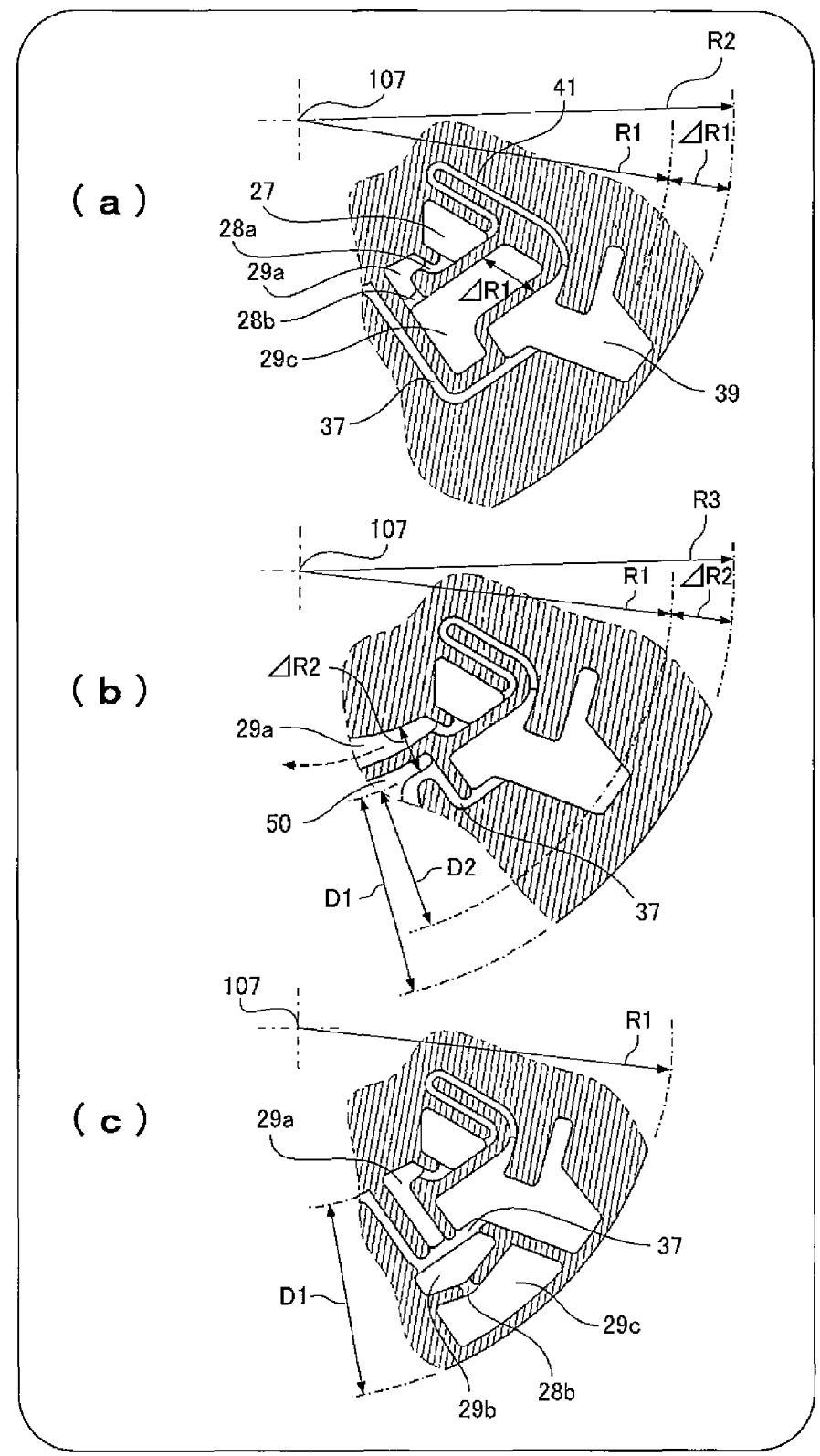
FIG. 33 shows an explanatory drawing of a layout in which the overflow cavity is disposed between the reserving cavity and the mixing cavity according to the first embodiment.

Following the explanation of the configuration of the mixing cavity 39 and the transfer method of the solution in accordance with FIGS. 25 to 31, the size reduction of the analyzing device 1 in the present embodiment will be described below in accordance with FIGS. 23 and 33.

FIG. 33(a) shows a layout of an overflow cavity 29c disposed between a reserving cavity 27 and the mixing cavity 39.

When a diluent 8 transferred to the reserving cavity 27 exceeds a predetermined quantity, the diluent 8 flows into an overflow cavity 29a through an overflow passage 28a and then flows into the overflow cavity 29c through an overflow passage 28b.

In this configuration, it is necessary to form the overflow cavity 29c next to the outer periphery position of the reserving cavity 27 to reduce the size of the analyzing device 1.

In FIG. 33(a), the plasma component 18a and the diluent 8 are transferred from the right of the mixing cavity 39. Thus it is difficult to transfer the mixed diluted plasma 40 from the right of the mixing cavity 39 to the subsequent process and it is necessary to transfer the diluted plasma 40 to the left of the mixing cavity 39.

However, the capillary passage 37 has to develop to the left through the outer periphery of the overflow cavity 29c. Thus the position of the mixing cavity 39 is determined by the radial position of the capillary passage 37. The overflow cavity 29c disposed between the reserving cavity 27 and the mixing cavity 39 expands the outside shape of the analyzing device 1 to R2 by a distance ΔR1.

Further, the capillary passage 37 disposed on the outer periphery has a long path developing to the inner periphery, increasing a loss of the diluted plasma 40.

FIG. 33(b) is a layout showing the overflow cavity 29a extended in a circumferential direction.

Since the overflow cavity 29a is extended in the circumferential direction, the mixing cavity 39 can be disposed next to the reserving cavity 27 on the inner periphery. However, the overflow cavity 29a is disposed on the left area and thus an inner position where the capillary passage 37 can develop is shifted to the outer periphery by ΔR2. Thus a space D1 containing a passage and a cavity for the subsequent process is reduced by ΔR2 to a space D2, so that it is difficult to arrange the passage and the cavity. Consequently, the outside shape of the analyzing device 1 is increased by ΔR2 to R3.

Therefore, in the present embodiment, the size of the analyzing device 1 is reduced by the configuration of FIG. 33(c).

In FIG. 33(c), when the diluent 8 transferred to the reserving cavity 27 exceeds a predetermined quantity, the diluent 8 flows into the overflow cavity 29a through the overflow passage 28a and then flows into the overflow cavity 29c, which is disposed at the outermost position, through the capillary passage 37, an overflow cavity 29b, and the overflow passage 28b toward the outside of the overflow cavity 29a in the radial direction.

The mixing cavity 39 is adjacent to the outer periphery of the reserving cavity 27, and the capillary passage 37 passes between the overflow cavity 29a and the overflow cavity 29b in the circumferential direction. In other words, in addition to the path for transferring the diluent 8 to the outer periphery by a centrifugal force, a path transfers the diluent 8 in the circumferential direction by a capillary force.

With this layout, as shown in FIG. 23(a), a centrifugal force is applied along arrow Y in measurement of the diluent 8. The diluent 8 passing through the overflow cavity 29a is transferred to the chamber 29c without flowing into the mixing cavity 39 connected to one circumferential end of the capillary passage 37.

In the case where the diluted plasma 40 is transferred from the mixing cavity 39 to the subsequent process through the capillary passage 37, as shown in FIG. 23(b), a capillary force is applied along arrow X. Thus the diluted plasma 40 can be transferred without flowing into the overflow cavities 29a and 29b formed next to the capillary passage 37.

At this point, the diluent 8 transferred to the chamber 29c and an sealing overflow cavity 29d is supplied to a second overflow passage 28d, the overflow passage 28b, and a first overflow passage 28c at the stop of the rotation of the analyzing device 1, so that the outlets of the chamber 29c and the sealing overflow cavity 29d are sealed from the atmosphere and a negative pressure is generated in the cavities. The second overflow passage 28d serves as an atmospheric-side overflow passage connected to an atmosphere-side overflow cavity 29e serving as an atmospheric-side overflow cavity communicating with the atmosphere. With this configuration, even when a liquid is transferred from the mixing cavity 39 to the capillary passage 37 during oscillations, the diluent 8 does not flow out of the chamber 29c and the diluted plasma 40 can be developed to the subsequent process. In the chamber 29c and the sealing overflow cavity 29d, air bubbles 51a and 51b are formed.

With the analyzing device 1 configured thus according to the present embodiment, a necessary passage pattern can be arranged without using unnecessary regions such as ΔR1 and ΔR2, thereby reducing the size of the analyzing device 1.

In the present embodiment, the path for transferring a discharged liquid during the measurement of the diluent 8 crosses the path for transferring the mixed diluted plasma 40 to the subsequent process. The paths are not always used in limited processes.

Step 7

Further, when the turntable 101 is rotationally driven in the clockwise direction (direction C2), as shown in FIG. 19(b), the diluted plasma 40 retained in the measuring passages 47a, 47b, and 47c overflows at the positions of bending sections 48a, 48b, 48c, and 48d that are connected to an opened-to-atmosphere cavity 50 communicating with the atmosphere, and then only a fixed quantity of the diluted plasma 40 flows into measuring chambers 52b and 52c and a reserving cavity 53.

The diluted plasma 40 retained in the overflow passage 47d at this point flows into an overflow cavity 54 through a backflow preventing passage 55. At this point, the diluted plasma 40 in the capillary passage 37 flows into the chamber 29c through the sealing overflow cavity 29b and the overflow passage 28b.

On a part of the side wall of the measuring passage 47a, a recessed section 49 is formed near the bending section 48a so as to communicate with the opened-to-atmosphere cavity 50. Thus the adhesion of liquid on the wall surface decreases near the bending section 48a, so that the liquid is drained well at the bending section 48a.

A measuring chamber 52a and the measuring chambers 52b and 52c are extended in a direction along which a centrifugal force is applied. To be specific, the measuring chambers are extended from the center of rotation to the outermost periphery of the analyzing device 1 so as to have small widths in the circumferential direction of the analyzing device 1.

The bottoms of the outer peripheries of the multiple measuring chambers 52a to 52c are arranged at the same radius of the analyzing device 1. Thus in measurements of the multiple measuring chambers 52a to 52c, it is not necessary to provide multiple light sources 112 of the same wavelength and multiple photodetectors 113 at different radius distances for the respective light sources 112, thereby reducing the cost of an apparatus. Since measurement can be conducted using different wavelengths in the same measurement cell, the sensitivity of measurement can be improved by selecting the optimum wavelength according to the concentration of a mixed solution.

Figure 34:
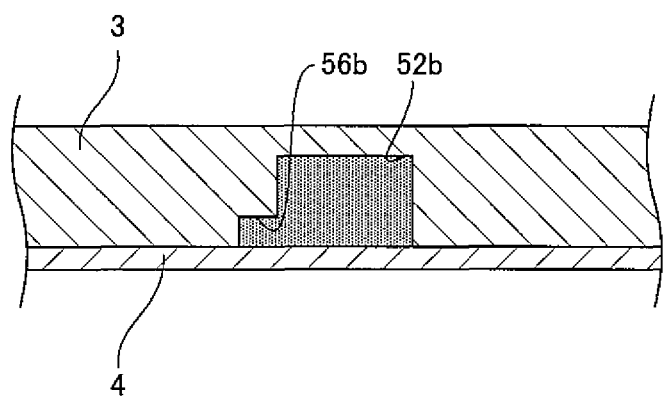
FIG. 34 is a sectional view of the analyzing device taken along line F-F of FIG. 19 according to the first embodiment.

On one side walls of the measuring chambers 52a to 52c in the circumferential direction, capillary areas 56a to 56c are formed so as to extend from the outer periphery positions to the inner peripheries of the measuring chambers. FIG. 34 is an F-F sectional view of FIG. 19(b).

The suction capacity of the capillary area 56b is not so large as to fully accommodate the sample liquid retained in the measuring chamber 52b. Similarly, the capacities of the capillary areas 56a and 56c are not so large as to fully accommodate the sample liquid retained in the measuring chambers 52a and 52c.

The optical path lengths of the measuring chambers 52a to 52c are adjusted according to the range of absorbance obtained from a mixed solution after a reaction of a component to be tested and reagents.

Figure 35:
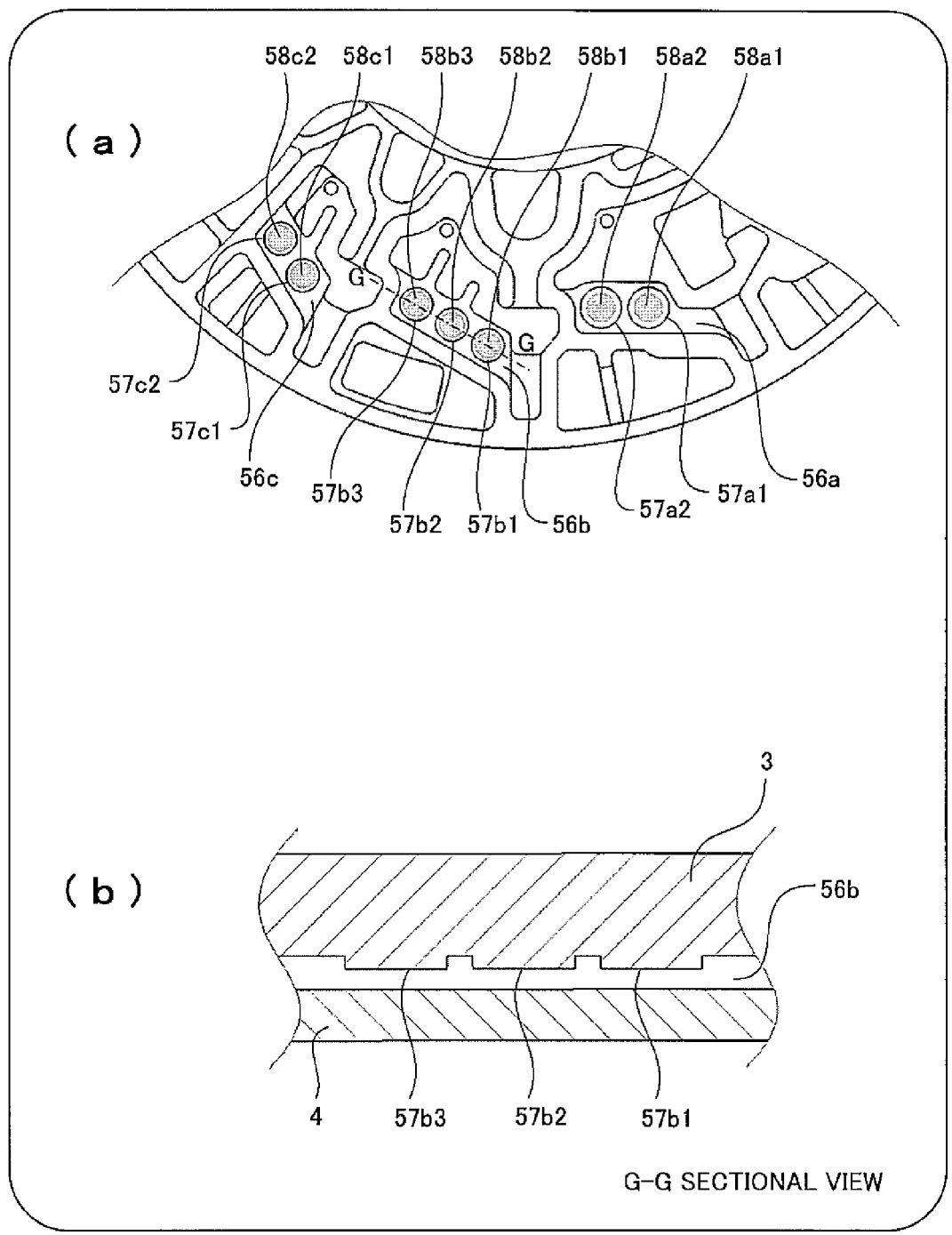
FIG. 35 shows an enlarged plan view of a state of reagents contained in capillary areas of the analyzing device and a G-G sectional view according to the first embodiment.

As shown in FIG. 35(a), in the capillary areas 56a, 56b, and 56c, reagents 58a1, 58a2, 58b1, 58b2, 58b3, 58c1, and 58c2 to be reacted with a component to be tested are respectively contained in reagent containing sections 57a1, 57a2, 57b1, 57b2, 57b3, 57c1, and 57c2 formed in the capillary areas 56a, 56b, and 56c. FIG. 35(b) is a G-G sectional view of FIG. 35(a).

The reagent containing sections 57b1, 57b2, and 57b3 are protruded from the capillary area 56b such that a clearance between the reagent containing sections 57b1, 57b2, and 57b3 and the cover substrate 4 is smaller than a clearance between the capillary area 56b and the cover substrate 4.

By applying the reagents 58b1, 58b2, and 58b3 to the reagent containing sections 57b1, 57b2, and 57b3, the expansion of the reagents 58b1, 58b2, and 58b3 can be suppressed by steps formed by the reagent containing sections 57b1, 57b2, and 57b3 and the capillary area 56b. Thus the different reagents can be contained without being mixed.

The clearance of the reagent containing sections 57b1, 57b2, and 57b3 is smaller than that of the capillary area 56b and thus liquid sucked into the capillary area 56b is reliably supplied into the reagent containing sections 57b1, 57b2, and 57b3. Consequently, the reagents 58b1, 58b2, and 58b3 can be reliably dissolved.

The capillary area 56b has a clearance of about 50 μm to 300 μm, which enables the application of a capillary force. Thus the reagent containing sections 57b1, 57b2, and 57b3 are protruded from the capillary area 56b only by about several tens μm. The capillary areas 56a and 56c have similar configurations.

Step 8

Next, the rotation of the turntable 101 is stopped, the analyzing device 1 is set at the position of FIG. 20(a), and the turntable 101 is controlled at a frequency of 60 Hz to 120 Hz so as to oscillate the analyzing device 1 by about ±1 mm, so that the diluted plasma 40 retained in the reserving cavity 53 is transferred to an operation cavity 61 by the action of a capillary force through a connecting section 59. The connecting section 59 is formed on the side wall of the reserving cavity 53 so as to be immersed under the liquid level of the diluted plasma 40.

Figure 36:
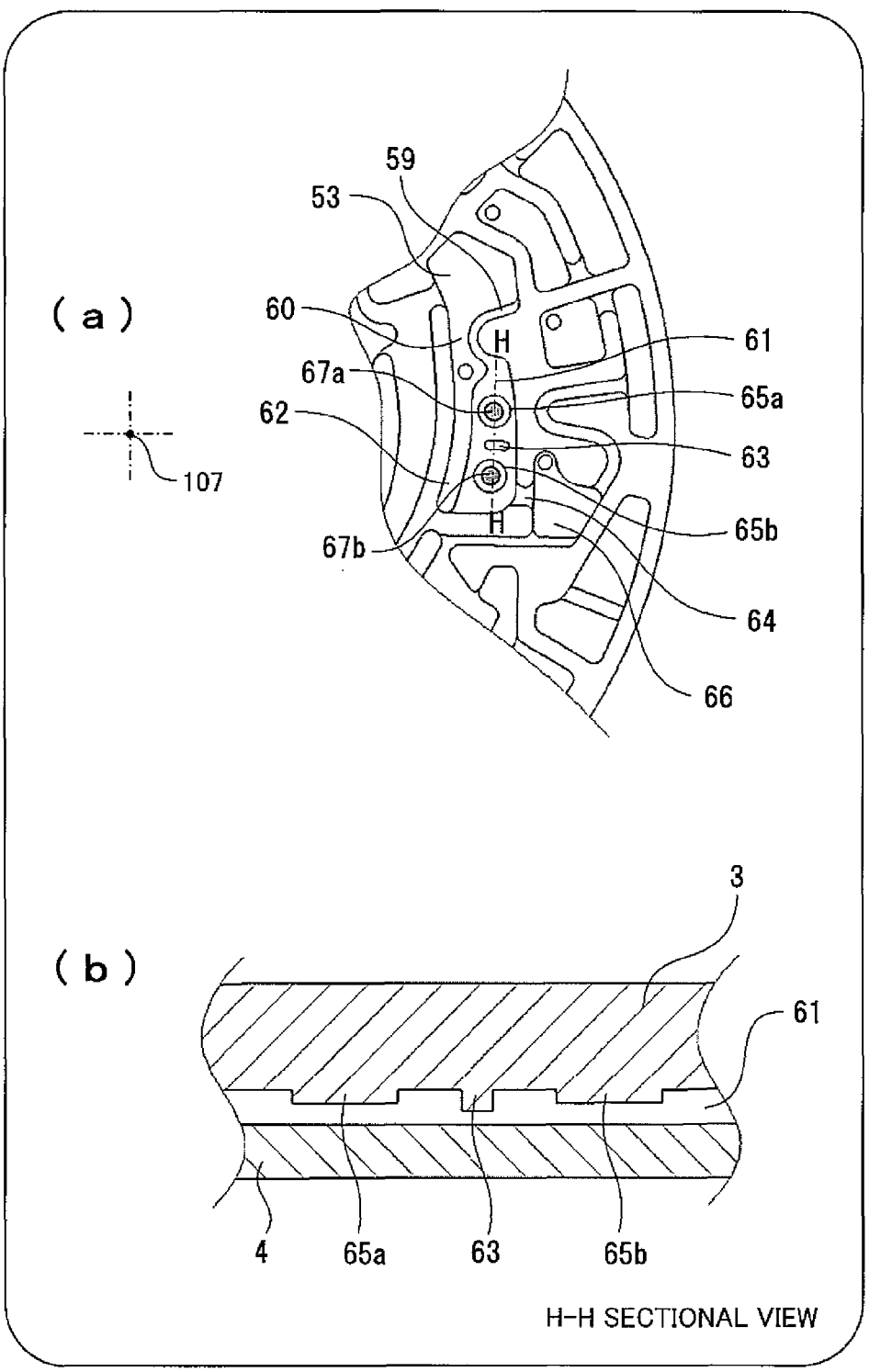
FIG. 36 shows an enlarged plan view of a state of reagents in the operation cavity of the analyzing device and an H-H sectional view according to the first embodiment.

Further, the turntable 101 is controlled at a frequency of 120 Hz to 200 Hz to agitate reagents 67a and 67b contained in the operation cavity 61 shown in FIG. 36(a) and the diluted plasma 40, so that a specific component in the diluted plasma 40 is reacted with the reagents.

The diluted plasma 40 transferred to the measuring chambers 52b and 52c is sucked into the capillary areas 56b and 56c by a capillary force as shown in FIG. 20(a). At this point, the reagents 58b1, 58b2, 58b3, 58c1, and 58c2 start dissolving and the specific component in the diluted plasma 40 starts reacting with the reagents.

As shown in FIG. 36(a), the operation cavity 61 is formed next to the reserving cavity 53 in the circumferential direction with respect to the rotation axis 107. A clearance of the operation cavity 61 from the cover substrate 4 enables the application of a capillary force, and the reagents 67a and 67b are contained in reagent containing sections 65a and 65b. In the operation cavity 61, an agitating rib 63 extended in the radial direction is formed around the reagents 67a and 67b, to be specific, between the reagents 67a and 67b.

As shown in FIG. 36(b), the cross sectional dimensions of the agitating rib 63 in the thickness direction of the cover substrate 4 are smaller than the cross sectional dimensions of the operation cavity 61 in the thickness direction of the cover substrate 4.

The reagent containing sections 65a and 65b are protruded from the operation cavity 61 such that a clearance between the reagent containing sections 65a and 65b and the cover substrate 4 is smaller than that of the operation cavity 61 from the cover substrate 4.

Since the clearance of the reagent containing sections 65a and 65b is smaller than that of the operation cavity 61, liquid flowing into the operation cavity 61 is reliably supplied to the reagent containing sections 65a and 65b. Thus the reagents 67a and 67b can be reliably dissolved. The reagent containing sections 65a and 65b are protruded from the operation cavity 61 only by about several tens μm.

On the inner periphery side of the operation cavity 61, a cavity 62 is formed that is connected to the reserving cavity 53 via a communicating section 60. The clearance of the cavity 62 from the cover substrate 4 does not enable the application of a capillary force. Further, the cavity 62 communicates with the atmosphere through the air hole 25h formed near the communicating section 60.

The reserving cavity 53 and the operation cavity 61 are connected via the connecting section 59 that is extended from the side wall of the reserving cavity 53 through the communicating section 60. The clearance of the connecting section 59 from the cover substrate 2 enables the application of a capillary force. In this configuration, the end of the connecting section 59 is circumferentially extended farther than the liquid level of the diluted plasma 40 contained in the reserving cavity 53, with respect to the rotation axis.

On the outer periphery of the operation cavity 61, a separating cavity 66 is formed. The separating cavity 66 is connected to the operation cavity 61 via a connecting passage 64. The cross sectional dimensions of the connecting passage 64 from the cover substrate 4 in the thickness direction form a clearance enabling the application of a capillary force. The cross sectional dimensions are regulated so as to have a larger capillary force than that of the operation cavity 61.

Although the space of the operation cavity 61 filled with the diluted plasma 40 is as large as the clearance, a small space 61a not filled with the diluted plasma 40 is left.

In the state of FIG. 20(a), the diluted plasma 40 comes into contact with the reagents 67a and 67b and the reagents 67a and 67b dissolve in the diluted plasma 40. In this state, the analyzing device 1 is oscillated by a predetermined angle with respect to the rotation axis 107, so that the diluted plasma 40 in the operation cavity 61 is moved by the space 61a in the operation cavity 61 and collides with the agitating rib 63 during agitation, achieving more reliable agitation. Thus even when the reagents have high specific gravities, it is possible to effectively prevent precipitation of the reagents.

Step 9

Next, the turntable 101 is rotationally driven in the clockwise direction (direction C2), so that as shown in FIG. 20(b), the diluted plasma having reacted with the reagents of the operation cavity 61 passes through the connecting passage 64 and flows into the separating cavity 66. Further, by keeping the high-speed rotation, aggregates generated in the operation cavity 61 are centrifugally separated. In the present embodiment, in a reaction of a component to be inspected and the reagents, a component inhibiting the reaction is removed in an upstream process. By reacting the diluted plasma with the reagents in the operation cavity 61, a specific component inhibiting a reaction in a downstream process is coagulated and aggregates are removed by centrifugal separation in the subsequent process.

Further, a mixed solution of the reagents retained in the capillary areas 56b and 56c and the diluted plasma is transferred to the outer peripheries of the measuring chambers 52b and 52c by a centrifugal force, so that the reagents and the diluted plasma are agitated.

In this configuration, the analyzing device 1 is repeatedly rotated and stopped to accelerate the agitation of the reagents and the diluted plasma. Thus it is possible to reliably perform agitation in a short time as compared with agitation performed only by diffusion.

Step 10

Next, when the rotation of the turntable 101 is stopped, the diluted plasma 40 is sucked into a capillary cavity 69 formed on the wall surface of the separating cavity 66 and flows, as shown in FIG. 21(a), into a measuring passage 80 through a connecting passage 70 communicating with the capillary cavity 69, so that a fixed quantity of the diluted plasma 40 is retained.

Moreover, the diluted plasma 40 containing the aggregates in the separating cavity 66 is sucked into a siphon-shaped connecting passage 68 that connects the separating cavity 66 and an overflow cavity 81a.

The mixed solution of the reagents and the diluted plasma in the measuring chambers 52b and 52c is sucked into the capillary areas 56b and 56c again by a capillary force.

As shown in FIG. 21(a), the outermost position of the capillary cavity 69 is extended to the outer periphery of the analyzing device 1 so as to be immersed in the diluted plasma retained in the separating cavity 66.

The capillary cavity 69 formed thus preferentially sucks the supernatant diluted plasma rather than a precipitate having a high specific gravity, so that the diluted plasma 40 free of precipitates can be transferred to the measuring passage 80 through the connecting passage 70.

Step 11

When the turntable 101 is rotationally driven in the clockwise direction (direction C2), as shown in FIG. 21(b), the diluted plasma 40 retained in the measuring passage 80 overflows at the position of a bending section 84 that is connected to an opened-to-atmosphere cavity 83 communicating with the atmosphere, and then only a fixed quantity of the diluted plasma 40 flows into the measuring chamber 52a.

The diluted plasma 40 in the separating cavity 66, the connecting passage 70, and the capillary cavity 69 flows into the overflow cavity 81a through the siphon-shaped connecting passage 68.

The mixed solution of the reagents retained in the capillary areas 56b and 56c and the diluted plasma is transferred to the outer peripheries of the measuring chambers 52b and 52c by a centrifugal force, so that the reagents and the diluted plasma are agitated.

At this point, the diluted plasma 40 transferred to the overflow cavity 81a is supplied to an overflow passage 82c when the rotation of the analyzing device 1 is stopped, the overflow passage 82c being connected to an overflow cavity 81b communicating with the atmosphere. Thus the outlet of the overflow cavity 81a is sealed from the atmosphere and a negative pressure is generated in the cavity 81a. It is therefore possible to prevent the diluted plasma 40 from passing through the connecting passage 68 from the overflow cavity 81a.

Step 12

Next, when the rotation of the turntable 101 is stopped, as shown in FIG. 22(a), the diluted plasma 40 transferred to the measuring chamber 52a is sucked into the capillary area 56a by a capillary force. At this point, the reagents 58a1 and 58a2 start dissolving and the specific component in the diluted plasma 40 starts reacting with the reagents.

Further, a mixed solution of the reagents and the diluted plasma in the measuring chambers 52b and 52c is sucked into the capillary areas 56b and 56c again by a capillary force.

Step 13

When the turntable 101 is rotationally driven in the clockwise direction (direction C2), as shown in FIG. 22(b), a mixed solution of the reagents retained in the capillary areas 56a, 56b, and 56c and the diluted plasma is transferred to the outer peripheries of the measuring chambers 52a, 52b, and 52c by a centrifugal force, so that the reagents and the diluted plasma are agitated.

The operations of steps 11 and 12 are repeatedly performed for the diluted plasma 40 transferred to the measuring chamber 52a, thereby accelerating the agitation of the reagents and the diluted plasma 40. Thus it is possible to reliably perform agitation in a short time as compared with agitation performed only by diffusion.

Step 14

The analyzing device 1 is rotationally driven in a counterclockwise direction (direction C1) or the clockwise direction (direction C2) and the measuring chambers 52a, 52b, and 52c pass between the light source 112 and the photodetector 113. At this point, the arithmetic unit 110 reads a detected value of the photodetector 113 and calculates the concentration of the specific component. When the diluted plasma 40 flows into the measuring chambers 52a, 52b, and 52c in steps 7 and 11, the arithmetic unit 110 reads a detected value of the photodetector 113 during the passage of the measuring chambers 52a, 52b, and 52c between the light source 112 and the photodetector 113, so that absorbance can be calculated before a reaction with the reagents. In the calculation of the arithmetic unit 110, the absorbance is used as reference data of the measuring chambers 52a, 52b, and 52c, improving the accuracy of measurement.

Second Embodiment

In the first embodiment, when the diluted plasma 40 is transferred to a downstream process through the capillary passage 37, as shown in FIG. 37(a), the analyzing device 1 is tilted and stopped at a position where the diluted plasma 40 in the mixing cavity 39 comes into contact with the inlet of the capillary passage 37. In a second embodiment of FIG. 37(b), when a capillary passage 37b extending to the bottom of a mixing cavity 39 is formed on the side wall of the mixing cavity 39, diluted plasma 40 in the mixing cavity 39 can be transferred to the inlet of a capillary passage 37 through the capillary passage 37b. Thus it is not necessary to tilt the analyzing device 1 as shown in FIG. 37(a).

In the foregoing embodiments, optical access is made in the measuring chambers and a component is measured according to attenuation. A component is similarly measured by electrically accessing a reactant of a reagent and a sample in the measuring chambers.

Third Embodiment

FIGS. 38 and 39 show a third embodiment of the present invention.

Figure 59:
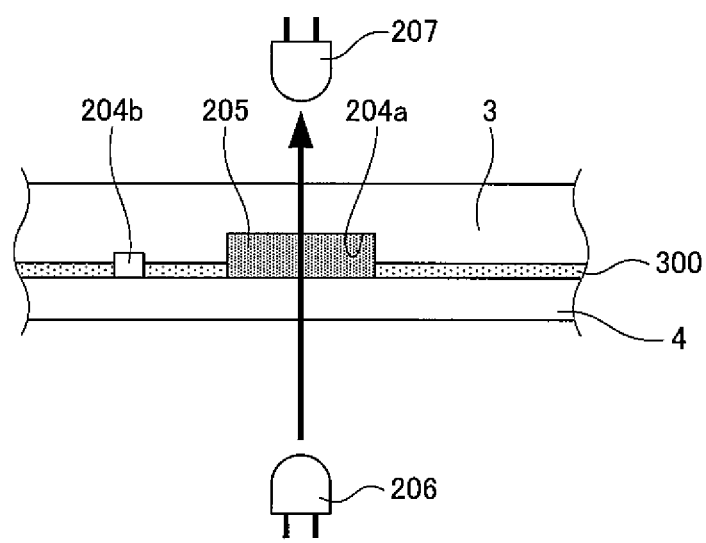
FIG. 59 is an enlarged sectional view showing an analyzing device of Patent Literature 3.

The analyzing device is similar to FIG. 59 of the related art in that a base substrate 3 having microchannels 204a and 204b and a cover substrate 4 closing the opening of the base substrate 3 are bonded to each other. The arrangement of a measuring chamber 210 relative to a liquid storage chamber 209 on the base substrate 3 and the connection of the measuring chamber 210 and an overflow chamber 211 are different from those of FIG. 61.

FIG. 38 is a perspective view showing the principle part of the base substrate 3. FIG. 39 is a plan view of FIG. 38.

An inlet 216 of the overflow chamber 211 is disposed in the same radial direction of rotation as an overflow port 214 of the measuring chamber 210. The inlet 216 of the overflow chamber 211 and the overflow port 214 of the measuring chamber 210 are connected via a third capillary passage 217c extending along the same radial direction of rotation. In FIG. 39, reference character L1 in the measuring chamber 210 denotes a liquid level of a sample liquid in a state in which a specified quantity of the sample liquid is sampled after the sample liquid flows into the measuring chamber 210 from the liquid storage chamber 209 through a first connecting passage 213a. An excessive sample liquid in the measuring chamber 210 exceeds the installation level of the third capillary passage 217c and flows into the overflow chamber 211, so that a fixed quantity of the sample liquid is sampled in the measuring chamber 210.

The outermost periphery of the measuring chamber 210 is connected to a measurement cell 212 via a siphon-shaped connecting passage 215 having a bent pipe disposed between the rotation axis of the analyzing device and the interface between the inlet 216 of the overflow chamber 211 and the capillary passage 217c. Reference numeral 208 denotes an inlet communicating with the atmosphere and reference numerals 218 and 219 denote air holes communicating with the atmosphere. The connecting passage 215 is 0.5 mm to 2 mm in width and is 50 µm to 200 µm in depth. The width and depth of the connecting passage 215 are not particularly limited as long as the connecting passage 215 can be filled with the sample liquid by a capillary force.

Comparing FIG. 61 and FIG. 39, the configuration of the present embodiment makes it possible to reduce a space S between the outer periphery of the liquid storage chamber 209 and the inner periphery of the measuring chamber 210 unlike in FIG. 61. In FIG. 61, the single measurement cell 212 is provided in the limited radial dimensions of the analyzing device, whereas in the third embodiment, the analyzing device having the same radial dimensions as in FIG. 61 may be provided with multiple measurement cells 212. In the case where the single measurement cell 212 is provided as in FIG. 61, the analyzing device can be reduced in size.

Further, a capillary valve 222 may be provided at a point of the connecting passage 215 to connect the measuring chamber 210 and the measurement cell 212, as indicated by a virtual line between the outermost position of the measuring chamber 210 and the measurement cell 212 in the radial direction of rotation.

The liquid storage chamber 209, the measuring chamber 210, the overflow chamber 211, and the measurement cell 212 are 0.3 mm to 2 mm in depth. The depths can be adjusted according to conditions (including an optical path length, a measured wavelength, the reaction concentration of the sample liquid, and the kind of reagent) for measuring the quantity and the absorbance of the sample liquid.

The cross sectional dimensions of the first connecting passage 213a in at least one of the thickness direction and the width direction are smaller than the cross sectional dimensions of the third capillary passage 217c in the thickness direction and the width direction such that the flow rate of liquid passing through the first connecting passage 213a is smaller than the flow rate of liquid passing through the third capillary passage 217c. To be specific, the first connecting passage 213a is a capillary tube that is 50 µm to 200 µm in depth and has cross sectional dimensions smaller than those of the third capillary passage 217c in the thickness direction. Thus when the sample liquid is transferred from the liquid storage chamber 209 to the measuring chamber 210 and is measured therein, it is possible to prevent the liquid level of the sample liquid retained in the connecting passage 215 from exceeding the innermost point of the connecting passage 215 and thus prevent the measured sample liquid from being transferred to the measurement cell 212, thereby further stabilizing a measuring process.

Fourth Embodiment

FIGS. 40 and 41 show a fourth embodiment of the present invention.

In FIG. 61 of the related art, the inlet 216 of the overflow chamber 211 is disposed inside the overflow port 214 of the measuring chamber 210 in the radial direction of rotation, and the inlet 216 of the overflow chamber 211 and the overflow port 214 of the measuring chamber 210 are connected via the capillary passage 217. In the fourth embodiment, as shown in FIG. 41, an inlet 216 of an overflow chamber 211 is disposed outside an overflow port 214 of a measuring chamber 210 in the radial direction of rotation, and the inlet 216 of the overflow chamber 211 and the overflow port 214 of the measuring chamber 210 are connected via a fourth capillary passage 217d. Other configurations are similar to those of FIG. 39 and components having the same effects are indicated by the same reference numerals.

In FIG. 41, reference character L1 in the measuring chamber 210 denotes a liquid level of a sample liquid in a state in which a specified quantity of the sample liquid is sampled in the measuring chamber 210 after the sample liquid flows from a liquid storage chamber 209. An excessive quantity of the sample liquid in the measuring chamber 210 from the liquid storage chamber 209 exceeds the installation level of the fourth capillary passage 217d and flows into the overflow chamber 211, so that a specified quantity of the sample liquid is sampled in the measuring chamber 210.

Comparing FIG. 61 and FIG. 41, the configuration of the fourth embodiment in FIG. 41 makes it possible to reduce a space S between the outer periphery of the liquid storage chamber 209 and the inner periphery of the measuring chamber 210 unlike in FIG. 61. In FIG. 61, the single measurement cell 212 is provided in the limited radial dimensions of the analyzing device, whereas in the fourth embodiment, the analyzing device having the same radial dimensions as in FIG. 61 can be provided with multiple measurement cells 212. In the case where the single measurement cell 212 is provided as in FIG. 61, the analyzing device can be reduced in size.

As in the third embodiment of FIG. 39, a capillary valve 222 may be provided at a point of a connecting passage 215 to connect the measuring chamber 210 and the measurement cell 212, as indicated by a virtual line between the outermost position of the measuring chamber 210 and the measurement cell 212 in the radial direction of rotation.

The liquid storage chamber 209, the measuring chamber 210, the overflow chamber 211, and the measurement cell 212 are 0.3 mm to 2 mm in depth. The depths can be adjusted according to conditions (including an optical path length, a measured wavelength, the reaction concentration of the sample liquid, and the kind of reagent) for measuring the quantity and the absorbance of the sample liquid.

The cross sectional dimensions of a first connecting passage 213a in at least one of the thickness direction and the width direction are smaller than the cross sectional dimensions of the fourth capillary passage 217d in the thickness direction and the width direction such that the flow rate of liquid passing through the first connecting passage 213a is smaller than the flow rate of liquid passing through the fourth capillary passage 217d. To be specific, the first connecting passage 213a is a capillary tube that is 50 μm to 200 μm in depth and has cross sectional dimensions smaller than those of the fourth capillary passage 217d in the thickness direction. Thus when the sample liquid is transferred from the liquid storage chamber 209 to the measuring chamber 210 and is measured therein, it is possible to prevent the liquid level of the sample liquid retained in the connecting passage 215 from exceeding the innermost point of the connecting passage 215 and thus prevent the measured sample liquid from being transferred to the measurement cell 212, thereby further stabilizing a measuring process.

Fifth Embodiment

In the third and fourth embodiments, the sample liquid is injected into the liquid storage chamber 209. When the sample liquid is a test object diluted with a diluent, it is necessary to provide a mixing device for mixing a fixed quantity of the test object and a fixed quantity of the diluent, a measuring chamber for measuring a fixed quantity from the diluent, and an overflow chamber for receiving an excessive quantity of the diluent, upstream of the liquid storage chamber 209 of the base substrate 3. In this case, in the third and fourth embodiments, configurations are further provided that are similar to specific configurations for metering the sample liquid in the measuring chamber, receiving an excessive sample liquid in the overflow chamber, and transferring the sample liquid metered in the measuring chamber to the subsequent stage of the measuring chamber, upstream of the liquid storage chamber 209 of the base substrate 3, so that the diluent can be metered and an excessive diluent can be received with a small space.

FIG. 42 shows a modification of the third embodiment as a specific example.

On a base substrate 3 of an analyzing device shown in FIG. 42, a first group G1 is formed for measuring a diluent and transferring the diluent to a mixing chamber 209c, a second group G2 is formed for measuring blood and transferring the blood to the mixing chamber 209c, and a third group G3 is formed for transferring a sample liquid mixed in the mixing chamber 209c to a measurement cell 212. The first, second, and third groups G1 to G3 have similar basic configurations. A diluent retaining section 209a and a blood retaining section 209b correspond to the liquid storage chamber 209 of the third embodiment. A diluent measuring chamber 210a, a blood metering chamber 210b, and a sample liquid measuring section 210c correspond to the measuring chamber 210 of the third embodiment. A diluent overflow chamber 211a, a blood discharging chamber 211b, and a sample liquid overflow chamber 211c correspond to the overflow chamber 211 of the third embodiment.

The diluent injected from an inlet 208a to the diluent retaining section 209a flows into the diluent measuring chamber 210a through a first connecting passage 213a. An excessive quantity of the diluent in the diluent measuring chamber 210a flows into the diluent overflow chamber 211a through a fifth capillary passage 217e corresponding to the third capillary passage 217c of the third embodiment. The diluent metered in the diluent measuring chamber 210a flows into the mixing chamber 209c through a siphon-shaped first connecting passage 215a.

Blood injected from an inlet 208b to the blood retaining section 209b flows into the blood metering chamber 210b through a second connecting passage 213b. An excessive quantity of the blood in the blood metering chamber 210b flows into the blood discharging chamber 211b through a sixth capillary passage 217f corresponding to the third capillary passage 217c of the third embodiment. The blood metered in the blood metering chamber 210b flows into the mixing chamber 209c through a siphon-shaped second connecting passage 215b.

The metered blood and the metered diluent are mixed in the mixing chamber 209c and flow into the sample liquid measuring section 210c through a siphon-shaped third connecting passage 215c. An excessive quantity of the sample liquid in the sample liquid measuring section 210c flows into the sample liquid overflow chamber 211c through a seventh capillary passage 217g corresponding to the third capillary passage 217c of the third embodiment. The metered sample liquid in the sample liquid measuring section 210c flows into the measurement cell 212 through a siphon-shaped fourth connecting passage 215d.

The fifth capillary passage 217e extending along the same radius connects the diluent measuring chamber 210a and the diluent overflow chamber 211a, thereby reducing a space between the diluent retaining section 209a and the diluent measuring chamber 210a in the first group G1. Further, the sixth capillary passage 217f extending along the same radius connects the blood metering chamber 210b and the blood discharging chamber 211b, thereby reducing a space between the blood retaining section 209b and the blood metering chamber 210b in the second group G2. Moreover, the seventh capillary passage 217g extending along the same radius connects the sample liquid measuring section 210c and the sample liquid overflow chamber 211c, thereby reducing a space between the mixing chamber 209c and the sample liquid measuring section 210c in the third group G3. Consequently, the chambers arranged in the radial direction can be arranged closer to the inner periphery of the analyzing device, reducing the size of the analyzing device.

As has been discussed, a fixed quantity of the sample liquid is measured and an excessive quantity of the sample liquid is received, or a fixed quantity of the diluent and a fixed quantity of the sample liquid are measured and an excessive quantity of the diluent and an excessive quantity of the sample liquid are received. In the case where only a fixed quantity of the diluent is measured and an excessive quantity of the diluent is received, the configurations of the third and fourth embodiments can be implemented only by replacing the sample liquid with the diluent.

Sixth Embodiment

Figure 43:
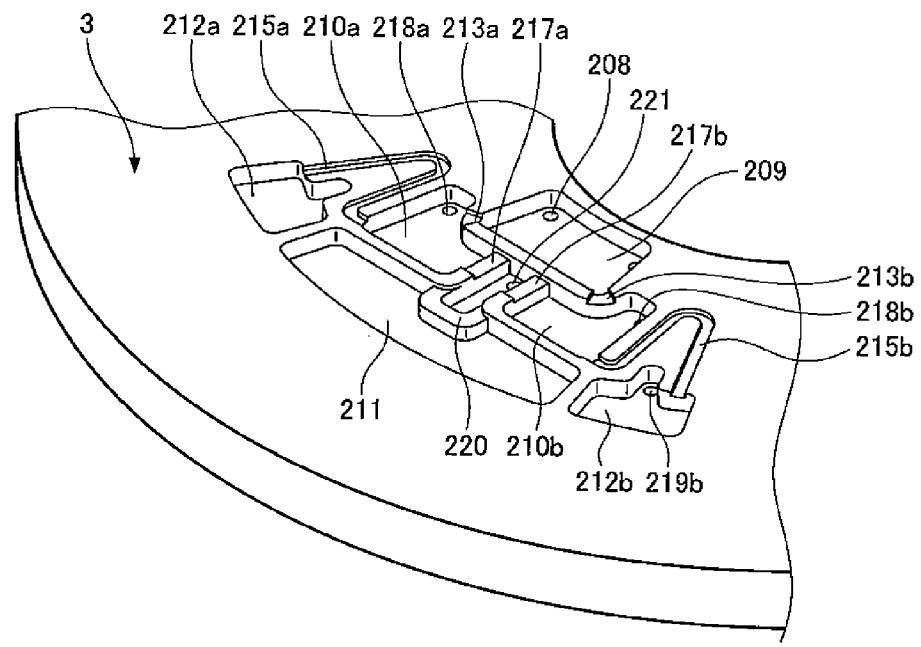
FIG. 43 is a perspective view showing the microchannel configuration of the base substrate of an analyzing device according to a sixth embodiment of the present invention.
Figure 44:
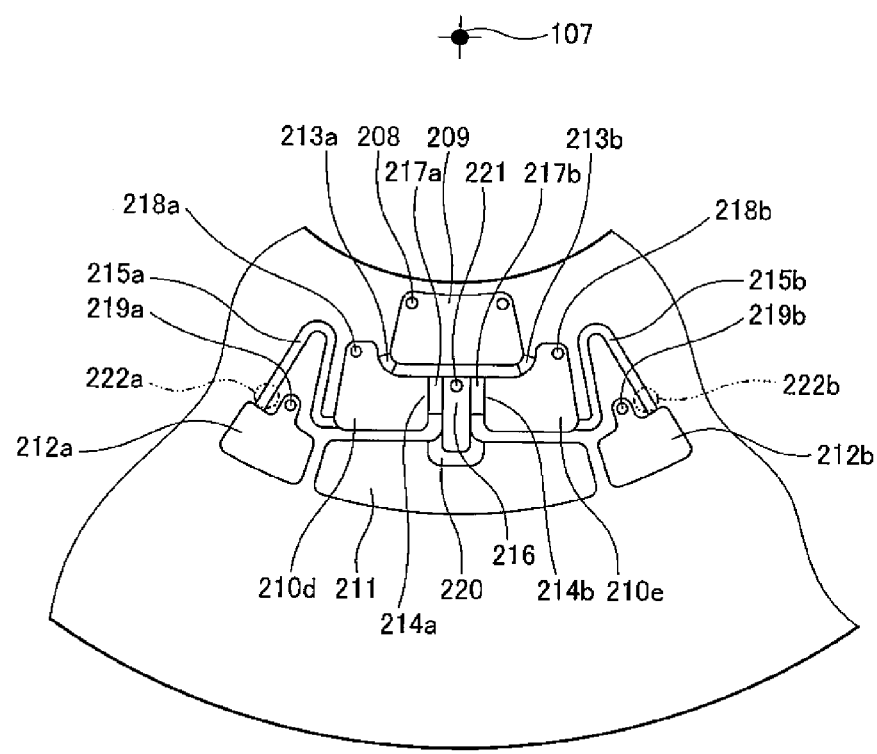
FIG. 44 is a plan view showing the microchannel configuration of the base substrate of the analyzing device according to the sixth embodiment.
Figure 45:
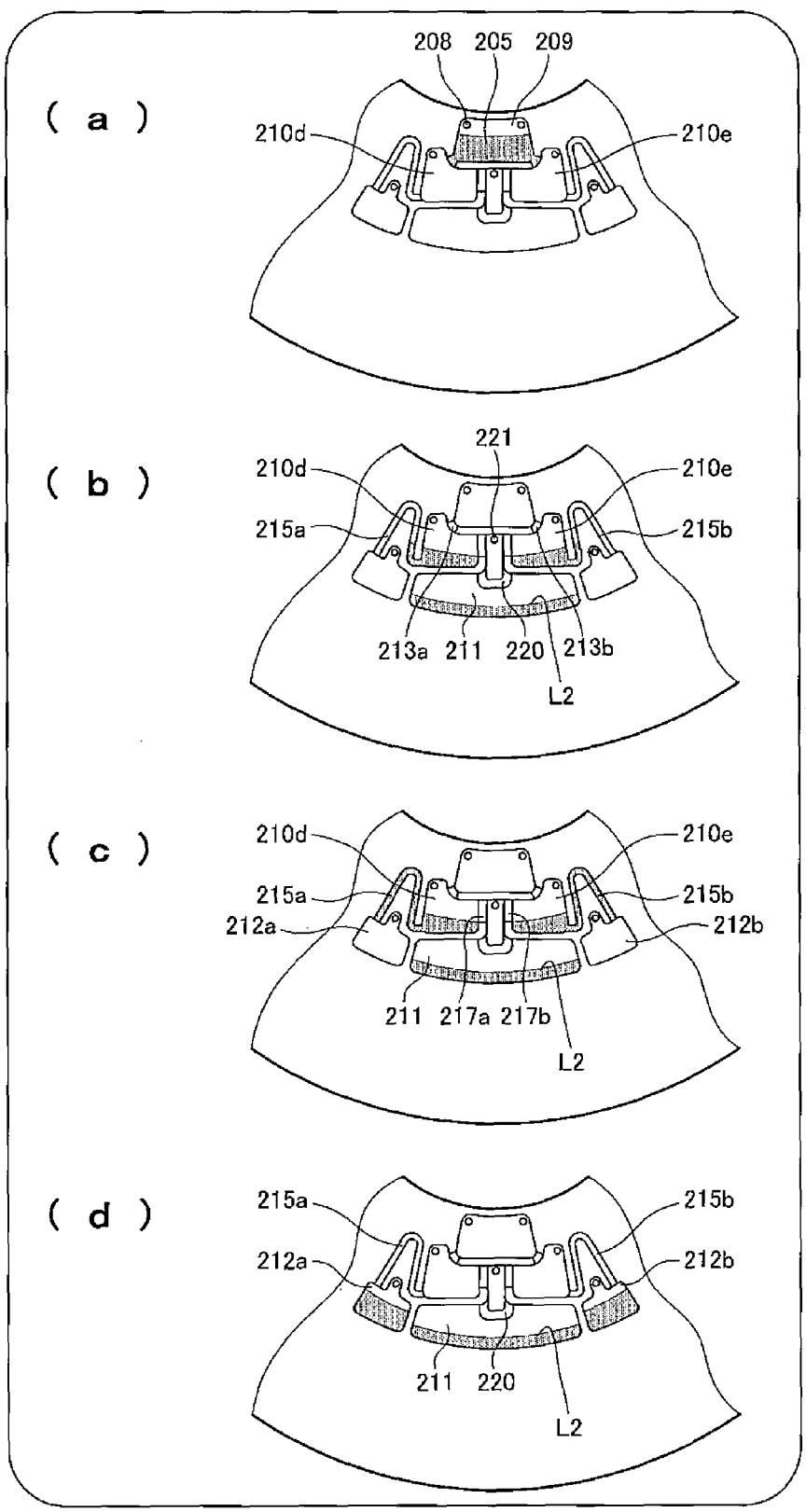
FIG. 45 shows a process diagram of a transfer process according to the sixth embodiment.

FIGS. 43, 44, and 45 show a sixth embodiment of the present invention.

FIG. 43 is a perspective view showing the principle part of a base substrate 3. FIG. 44 is a plan view of FIG. 43.

In the foregoing embodiments, the single measuring chamber 210, the single overflow chamber 211, and the single measurement cell 212 are provided for the single liquid storage chamber 209. The present embodiment is different from these embodiments in that an overflow chamber 211, first and second measuring chambers 210d and 210e, and first and second measurement cells 212a and 212b are provided for a liquid storage chamber 209.

As shown in FIGS. 43 and 44, with respect to a rotation axis 107 serving as the rotation axis of an analyzing device during analysis, the liquid storage chamber 209 containing a sample liquid to be analyzed is provided on the innermost periphery of the base substrate 3. Outside the liquid storage chamber 209 in the radial direction of rotation, the first measuring chamber 210d and the second measuring chamber 210e are formed. The first measuring chamber 210d is connected to the liquid storage chamber 209 via a first connecting passage 213a. The second measuring chamber 210e is connected to the liquid storage chamber 209 via a second connecting passage 213b.

On the base substrate 3, the overflow chamber 211 is formed between the first measuring chamber 210d and the second measuring chamber 210e. An inlet 216 of the overflow chamber 211 and a first overflow port 214a of the first measuring chamber 210d are connected via a first capillary passage 217a extending along the same radial direction of rotation. The inlet 216 of the overflow chamber 211 and a second overflow port 214b of the second measuring chamber 210e are connected via a second capillary passage 217b extending along the same radial direction of rotation.

The outermost periphery of the first measuring chamber 210d is connected to the first measurement cell 212a via a siphon-shaped first connecting passage 215a having a bent pipe disposed between the rotation axis of the analyzing device and the interface between the inlet 216 of the overflow chamber 211 and the first capillary passage 217a. The outermost periphery of the second measuring chamber 210e is connected to the second measurement cell 212b via a siphon-shaped second connecting passage 215b having a bent pipe disposed between the rotation axis of the analyzing device and the interface between the inlet 216 of the overflow chamber 211 and the second capillary passage 217b. The first and second connecting passages 215a and 215b are 0.5 mm to 2 mm in width and 50 μm to 200 μm in depth. The widths and depths of the first and second connecting passages 215a and 215b are not particularly limited as long as the connecting passages can be filled with the sample liquid by a capillary force.

The cross sectional dimensions of the first and second connecting passages 213a and 213b in at least one of the thickness direction and the width direction are smaller than the cross sectional dimensions of the first and second capillary passages 217a and 217b in the thickness direction and the width direction such that the flow rates of liquid passing through the first and second connecting passages 213a and 213b are smaller than the flow rates of liquid passing through the first and second capillary passages 217a and 217b. To be specific, the first and second connecting passages 213a and 213b are capillary tubes that are 50 μm to 200 μm in depth and have cross sectional dimensions smaller than those of the first and second capillary passages 217a and 217b in the thickness direction. Thus when the sample liquid is transferred from the liquid storage chamber 209 to a measuring chamber 210 and is measured therein, it is possible to prevent the liquid level of the sample liquid retained in a connecting passage 215 from exceeding the innermost point of the connecting passage 215 and thus prevent the measured sample liquid from being transferred to a measurement cell 212, thereby further stabilizing a measuring process.

The overflow chamber 211 further includes a sill 220 that limits the cross sectional dimensions of the overflow chamber 211 in the thickness direction to enable the application of a capillary force. Reference characters 218a, 218b, 219a, 219b, and 221 denote air holes communicating with the atmosphere. The air hole 221 is formed in an area where a capillary force is not applied inside the sill 220 of the overflow chamber 211. Thus an excessive quantity of the sample liquid smoothly flows from the first and second measuring chambers 210d and 210e to the overflow chamber 211.

FIGS. 45(a) to 45(d) show the transfer process of the analyzing device.

As shown in FIG. 45(a), the sample liquid is injected from an inlet 208 and is stored in the liquid storage chamber 209 and then the analyzing device is rotated, so that as shown in FIG. 45(b), the sample liquid can be transferred to the first and second measuring chambers 210d and 210e through the first and second connecting passages 213a and 213b. Portions of the sample liquid transferred to the first and second measuring chambers 210d and 210e overflow the first and second capillary passages 217a and 217b from the first and second overflow ports 214a and 214b and flow into the overflow chamber 211. At this point, the sample liquid in the first and second connecting passages 215a and 215b reaches only a position corresponding to a distance from the rotation axis of the analyzing device to the interface between the inlet 216 of the overflow chamber 211 and the first and second capillary passages 217a and 217b in the radial direction of rotation.

When the analyzing device is decelerated or stopped after the first and second measuring chambers 210d and 210e are filled with the sample liquid, as shown in FIG. 45(c), a capillary force is applied in the first and second connecting passages 215a and 215b and the sample liquid reaches the inlets of the first and second measurement cells 212a and 212b. At this point, the first and second measurement cells 212a and 212b have a large depth and receive a capillary force quite smaller than the capillary force of the first and second connecting passages 215a and 215b. Thus the sample liquid does not flow into the first and second measurement cells 212a and 212b.

Further, the provision of the sill 220 prevents the sample liquid from flowing backward from the overflow chamber 211 to the first and second measuring chambers 210d and 210e when the analyzing device is decelerated or stopped.

After the first and second connecting passages 215a and 215b are filled with the sample liquid, the analyzing device is rotated again, so that as shown in FIG. 45(d), the sample liquid retained in the first and second measuring chambers 210d and 210e is transferred to the first and second measurement cells 212a and 212b by a siphon action and is analyzed separately in the first and second measurement cells 212a and 212b.

On the base substrate 3, the single overflow chamber 211, the measuring chambers 210d and 210e, and the first and second measurement cells 212a and 212b are properly formed for the single liquid storage chamber 209. In the case where the analyzing device has the same radial dimensions as in FIG. 61, multiple measurement cells 212 may be provided.

Further, capillary valves 222a and 222b may be respectively provided at points of the first and second connecting passages 215a and 215b to connect the first and second measuring chambers 210d and 210e and the first and second measurement cells 212a and 212b, as indicated by virtual lines between the outermost positions of the first and second measuring chambers 210d and 210e and the first and second measurement cells 212a and 212b in the radial direction of rotation.

The liquid storage chamber 209, the first and second measuring chambers 210d and 210e, the overflow chamber 211, and the first and second measurement cells 212a and 212b are 0.3 mm to 2 mm in depth. The depths can be adjusted according to conditions (including an optical path length, a measured wavelength, the reaction concentration of the sample liquid, and the kind of reagent) for measuring the quantity and the absorbance of the sample liquid.

Seventh Embodiment

Figure 46:
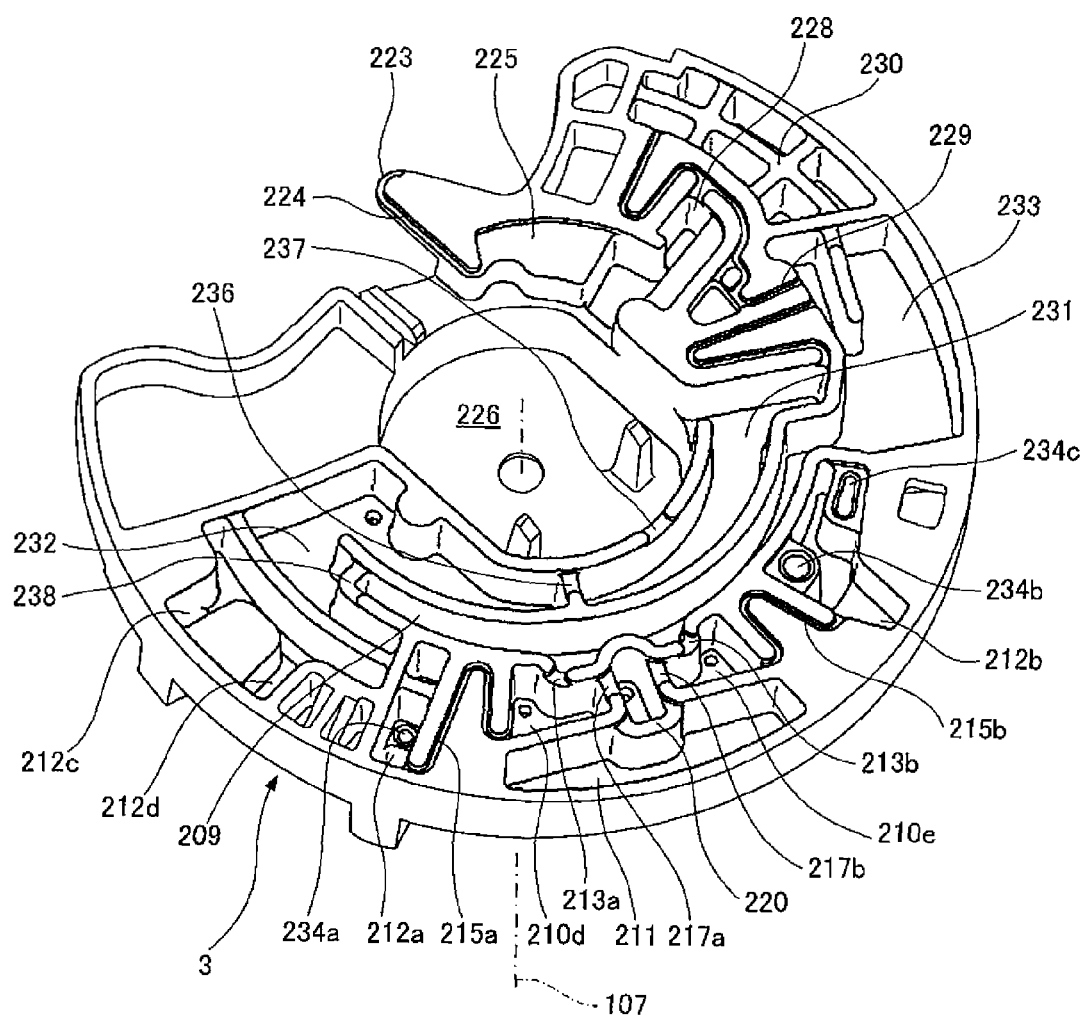
FIG. 46 is a perspective view showing the microchannel configuration of the base substrate of an analyzing device according to a seventh embodiment of the present invention.

FIGS. 46 and 47 show a seventh embodiment of the present invention.

The seventh embodiment shows a specific example of an analyzing device in which the configuration of the sixth embodiment is developed on a base substrate 3.

In the analyzing device formed by joining the base substrate 3 and a cover substrate (not shown in FIGS. 46 and 47) 4, blood dropped to a blood dropping section 223 is sucked into a blood retaining section 225 through a microchannel 224 formed between the base substrate 3 and the cover substrate 4. Further, a diluent is set in a diluent container (not shown) set in a diluent reservoir 226. In this state, the analyzing device is rotationally driven about a rotation axis 107, so that blood is metered in a blood metering chamber 229 through a blood separating section 228. Excessive blood is collected to a blood discharging section 230. The diluent is metered in a diluent metering chamber 231. An excessive diluent is collected to a diluent discharging section 232 through a capillary passage 236. The blood metered in the blood metering chamber 229 and the diluent metered in the diluent metering chamber 231 are mixed in a mixing section 233 and are transferred to a liquid storage chamber 209.

The diluted blood transferred as the sample liquid to the liquid storage chamber 209 is transferred to first and second measuring chambers 210d and 210e through first and second connecting passages 213a and 213b and is metered therein. Excessive diluted blood is collected to an overflow chamber 211 through first and second capillary passages 217a and 217b. The analyzing device is rotated again, so that the diluted blood metered in the first and second measuring chambers 210d and 210e is transferred to first and second measurement cells 212a and 212b from the first and second measuring chambers 210d and 210e through siphon-shaped first and second connecting passages 215a and 215b, and is analyzed separately in the first and second measurement cells 212a and 212b. In the first and second measurement cells 212a and 212b, reagents 234a, 234b, and 234c are set.

In the seventh embodiment, the diluent metering chamber 231 for measuring a fixed quantity of the diluent is curved around the diluent reservoir 226, the diluent discharging section 232 for receiving an excessive diluent from the diluent metering chamber 231 is also formed around the diluent reservoir 226, and the capillary passage 236 connecting the diluent metering chamber 231 and the diluent discharging section 232 is extended along the same radial direction of rotation like the first and second capillary passages 217a and 217b. This configuration effectively reduces the size of the analyzing device. In this case, the cross sectional dimensions of a connecting passage 237 in at least one of the thickness direction and the width direction are smaller than the cross sectional dimensions of the capillary passage 236 in the thickness direction and the width direction such that the flow rate of liquid passing through the connecting passage 237 connecting the diluent reservoir 226 and the diluent metering chamber 231 is smaller than the flow rate of liquid passing through the capillary passage 236. In the seventh embodiment, an excessive quantity of the sample liquid in the liquid storage chamber 209 passes through the diluent discharging section 232 through a capillary passage 238 and is received by third and fourth measurement cells 212c and 212d.

Eighth Embodiment

Figure 48:
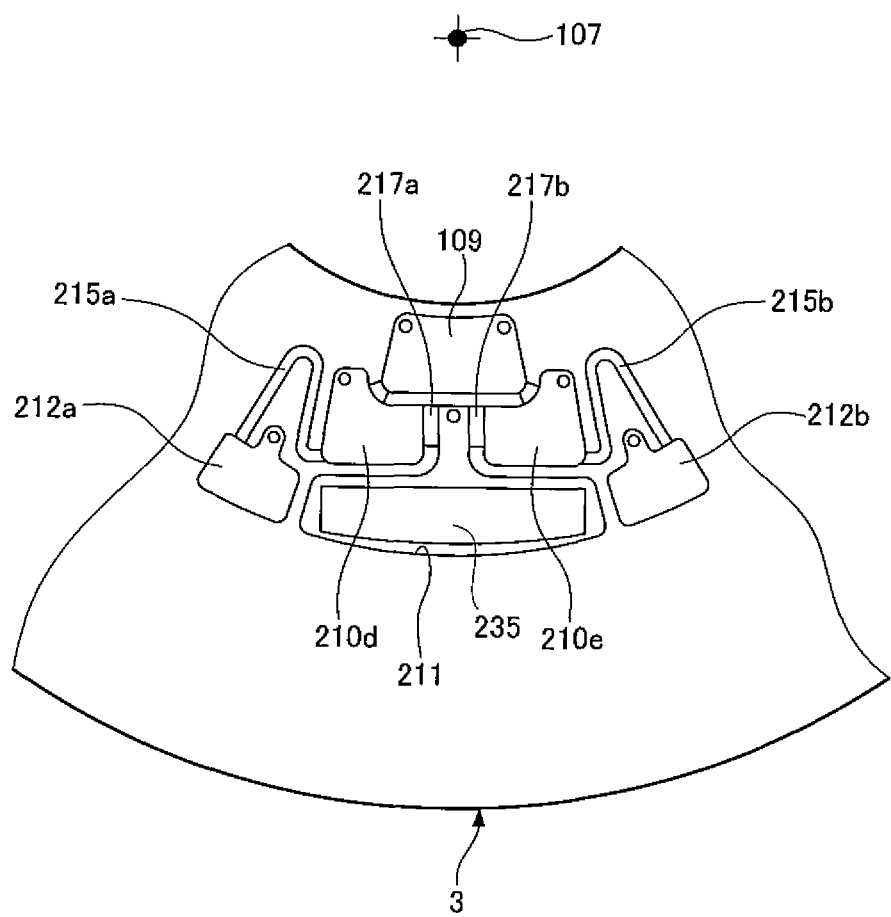
FIG. 48 is a plan view showing the microchannel configuration of the base substrate of an analyzing device according to an eighth embodiment.

FIG. 48 shows an eighth embodiment of the present invention.

In the seventh and eighth embodiments, the sill 220 is formed in the overflow chamber 211 to reduce a clearance from the cover substrate 4 to a space enabling the application of a capillary force. The sill 220 may be removed in the present embodiment.

In FIG. 48, an absorbent material 235 is disposed in an overflow chamber 211. A sample liquid flowing into the overflow chamber 211 is absorbed by the absorbent material 235. Thus when the analyzing device is decelerated or stopped, it is possible to prevent the sample liquid from flowing backward from the overflow chamber 211 to first and second measuring chambers 210d and 210e. The seventh embodiment may be similarly configured.

Ninth Embodiment

FIGS. 49 to 54 show a ninth embodiment of the present invention.

Figure 51:
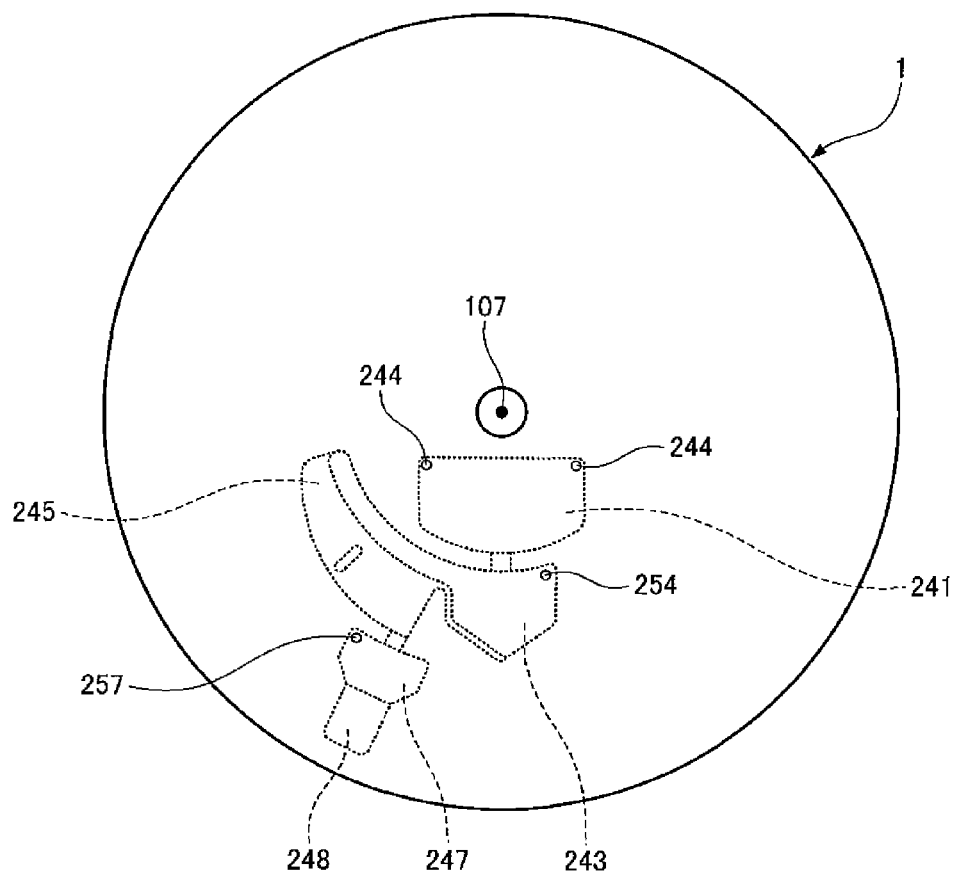
FIG. 51 is a plan view showing the analyzing device according to the ninth embodiment.

As shown in FIG. 51, an analyzing device 1 has a disc-like shape and is rotationally driven about a rotation axis 107. The rotation axis 107 is tilted such that the rotationally driven analyzing device 1 is tilted by a predetermined angle of 0° to 45° relative to a level. The predetermined angle is preferably 10° to 45°.

Figure 52:
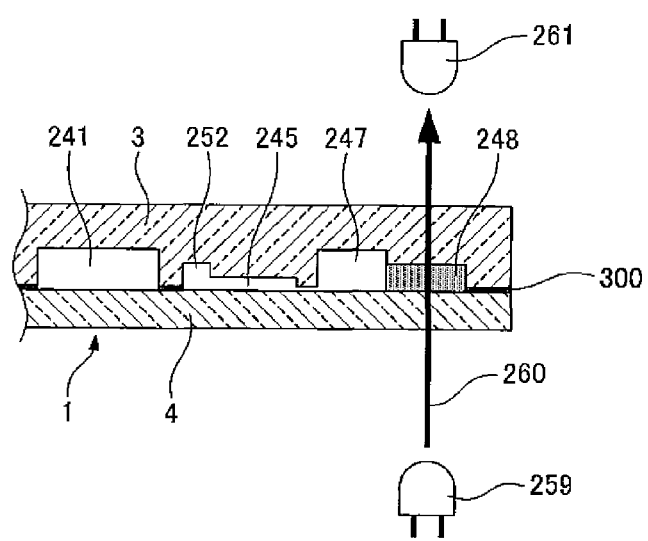
FIG. 52 is a sectional view showing the principle part of the analyzing device according to the ninth embodiment.

As shown in FIG. 52, the analyzing device 1 is configured such that a base substrate 3 is bonded via an adhesive layer 300 to a cover substrate 4 closing the opening of the base substrate 3. The base substrate 3 includes a microchannel liquid storage chamber 241, a first reserving cavity 243, an operation cavity 245, and second reserving cavities 247 and 248.

Figure 49:
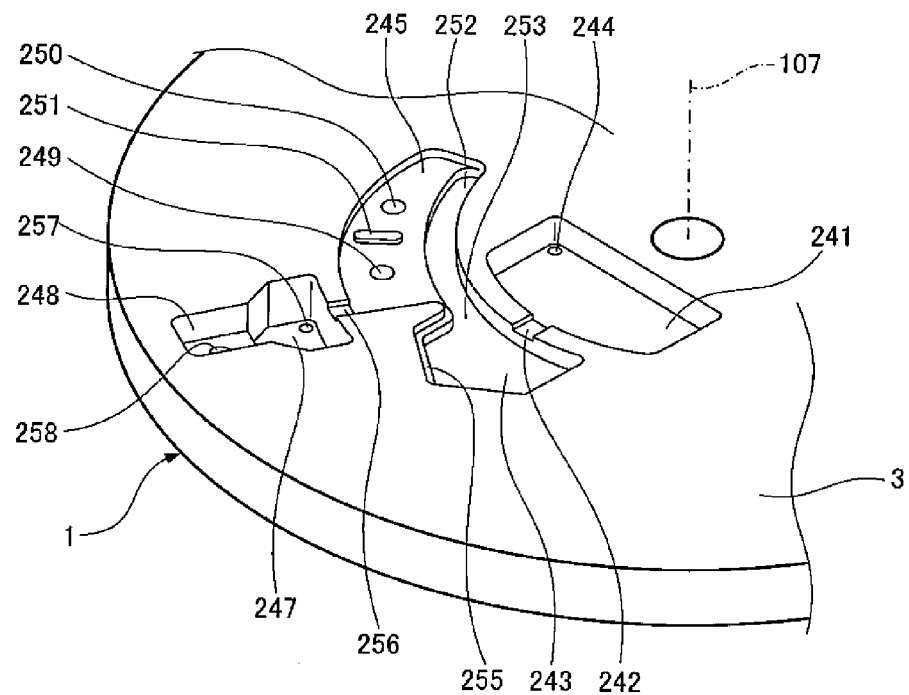
FIG. 49 is a principle part perspective view showing the microchannel configuration of the base substrate of an analyzing device according to a ninth embodiment of the present invention.
Figure 50:
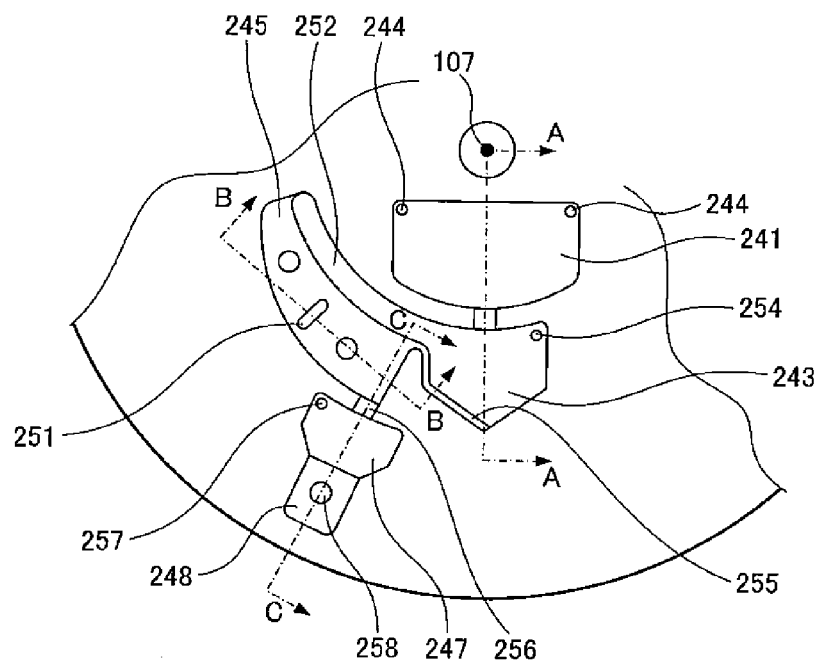
FIG. 50 is a principle part plan view showing the microchannel configuration of the base substrate of the analyzing device according to the ninth embodiment.

FIG. 49 is a perspective view showing the principle part of the base substrate 3. FIG. 50 is a plan view of FIG. 49. FIG. 53 shows an A-A sectional view, a B-B sectional view, and a C-C sectional view of FIG. 50.

The liquid storage chamber 241 is formed between the rotation axis and the first reserving cavity 243 of the base substrate 3. The liquid storage chamber 241 receives a sample liquid from a through hole 244. The liquid storage chamber 241 and the first reserving cavity 243 are connected via a communicating passage 242. As shown in FIG. 53(a), a clearance of the communicating passage 242 from the cover substrate 4 is formed so as to enable the application of a capillary force.

The operation cavity 245 is formed next to the first reserving cavity 243 of the base substrate 3 with respect to the rotation axis in the circumferential direction. A clearance of the operation cavity 245 from the cover substrate 4 is formed so as to enable the application of a capillary force and the operation cavity 245 contains first reagents 249 and 250. In the operation cavity 245, an agitating rib 251 is formed around the first reagents 249 and 250, to be specific, the agitating rib 251 extends between the first reagents 249 and 250 in the radial direction. The cross sectional dimensions of the agitating rib 251 relative to the cover substrate 4 in the thickness direction are smaller than the cross sectional dimensions of the operation cavity 245 relative to the cover substrate 4 in the thickness direction. On the inner periphery of the operation cavity 245, a cavity 252 is formed and is connected to the first reserving cavity 243 via a communicating section 253. A clearance of the cavity 252 from the cover substrate 4 is formed so as not to enable the application of a capillary force. Further, the cavity 252 communicates with the atmosphere via a through hole 254 formed in the first reserving cavity 243.

The first reserving cavity 243 and the operation cavity 245 are connected via a connecting section 255 extending from the side wall of the first reserving cavity 243 through the communicating section 253. As shown in FIG. 53(b), a clearance of the connecting section 255 from the cover substrate 4 is formed so as to enable the application of a capillary force. In this configuration, the end of the connecting section 255 is circumferentially extended farther than the liquid level of the sample liquid contained in the first reserving cavity 243, with respect to the rotation axis. More specifically, the end of the connecting section 255 is extended to the outermost periphery of the first reserving cavity 243.

On the outer periphery of the operation cavity 245, the second reserving cavities 247 and 248 are formed. Of the second reserving cavities 247 and 248, the inner second reserving cavity 247 is deeper than the outer second reserving cavity 248 and is connected via a connecting passage 256. As shown in FIG. 53(c), the cross sectional dimensions of the connecting passage 256 from the cover substrate 4 in the thickness direction form a clearance enabling the application of a capillary force. The cross sectional dimensions are regulated so as to have a larger capillary force than that of the operation cavity 245. Reference numeral 257 denotes a communicating hole that communicates with the atmosphere. The second reserving cavity 248 contains a second reagent 258.

FIGS. 54(a) to 54(d) show a transfer process of the reagents.

As shown in FIG. 54(a), a sample liquid 283 is injected into the liquid storage chamber 241, and then the analyzing device 1 is rotationally driven about the rotation axis 107, so that the sample liquid 283 is passed through the communicating passage 242 and is transferred to the first reserving cavity 243 by a centrifugal force.

When the rotation of the analyzing device 1 is decelerated in a state in which the sample liquid has been moved to the first reserving cavity 243, or when the analyzing device 1 is stopped with the outermost part of the first reserving cavity 243 directed downward as shown in FIG. 54(b), the sample liquid 283 in the first reserving cavity 243 is transferred to the operation cavity 245 through the connecting section 255 by a capillary force as shown in FIG. 54(c). The operation cavity 245 has a larger capillary force than the connecting section 255. In a state in which the sample liquid 283 has been sucked into the operation cavity 245, the space of the operation cavity 245 filled with the sample liquid 283 is as large as the clearance but a small space 246 not filled with the sample liquid 283 is left.

In the state of FIG. 54(c), the sample liquid 283 comes into contact with the first reagents 249 and 250 and the first reagents 249 and 250 dissolve in the sample liquid. In this state, the analyzing device 1 is oscillated by a predetermined angle with respect to the rotation axis 107, so that the sample liquid 283 in the operation cavity 245 is moved by the space 246 and collides with the agitating rib 251 during agitation, achieving more reliable agitation. Thus even when the reagents have high specific gravities, it is possible to effectively prevent precipitation of the reagents.

After sufficient agitation in FIG. 54(c), the analyzing device 1 is rotationally driven about the rotation axis 107, so that the sample liquid in the operation cavity 245 flows into the second reserving cavities 247 and 248 through the connecting passage 256 and is retained in the outer second reserving cavity 248 as shown in FIG. 54(d). Since the outer second reserving cavity 248 contains the second reagent 258, when the analyzing device 1 in the state of FIG. 54(d) is oscillated by a predetermined angle with respect to the rotation axis 107, the second reagent 258 is further dissolved in the sample liquid.

After the second reagent 258 is completely dissolved, as shown in FIG. 52, light 260 is transmitted from a light source 259 to the sample liquid in the second reserving cavity 248, which serves as an outer measurement spot, while the analyzing device 1 is rotated. Then, the light is read by a photodetector 261 and is analyzed.

With this configuration, even if the quantity of the sample liquid is small, it is possible to reliably move the sample liquid between the first reserving cavity 243 and the operation cavity 245 and dissolve the first reagents 249 and 250. Further, it is possible to transfer the sample liquid of the operation cavity 245 to the second reserving cavities 247 and 248 to dissolve the second reagent 258, achieving correct measurement.

Tenth Embodiment

In the ninth embodiment, the sample liquid is injected into the liquid storage chamber 241 and is detected in the second reserving cavity 248 at the end of the transfer of the sample liquid. A tenth embodiment shown in FIGS. 54 and 55 describes an analyzing device including a first reserving cavity 243, an operation cavity 245, and second reserving cavities 247 and 248 in a transfer process.

Constituent elements having the same functions as in the ninth embodiment are indicated by the same reference numerals.

Figure 55:
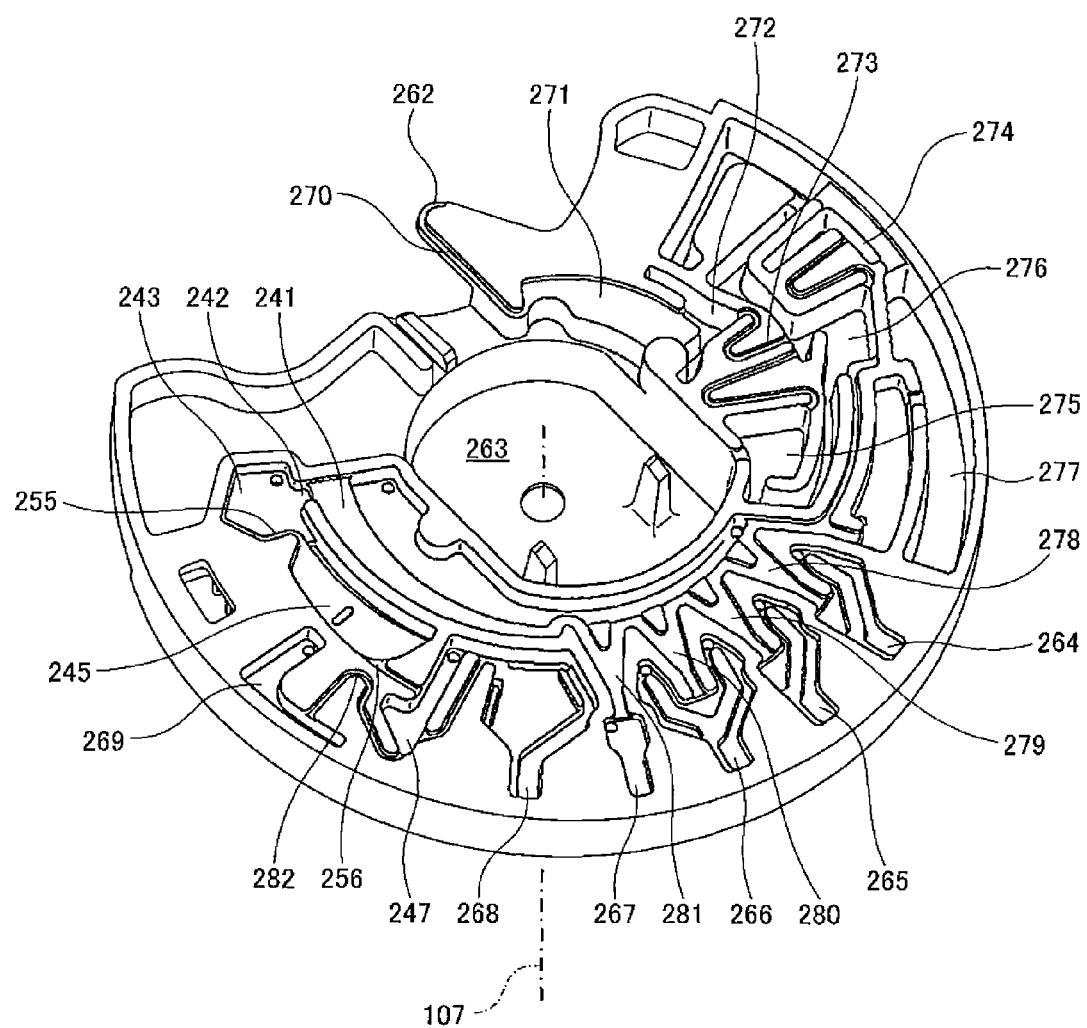
FIG. 55 is a perspective view showing the microchannel configuration of the base substrate of an analyzing device according to a tenth embodiment of the present invention.
Figure 57:
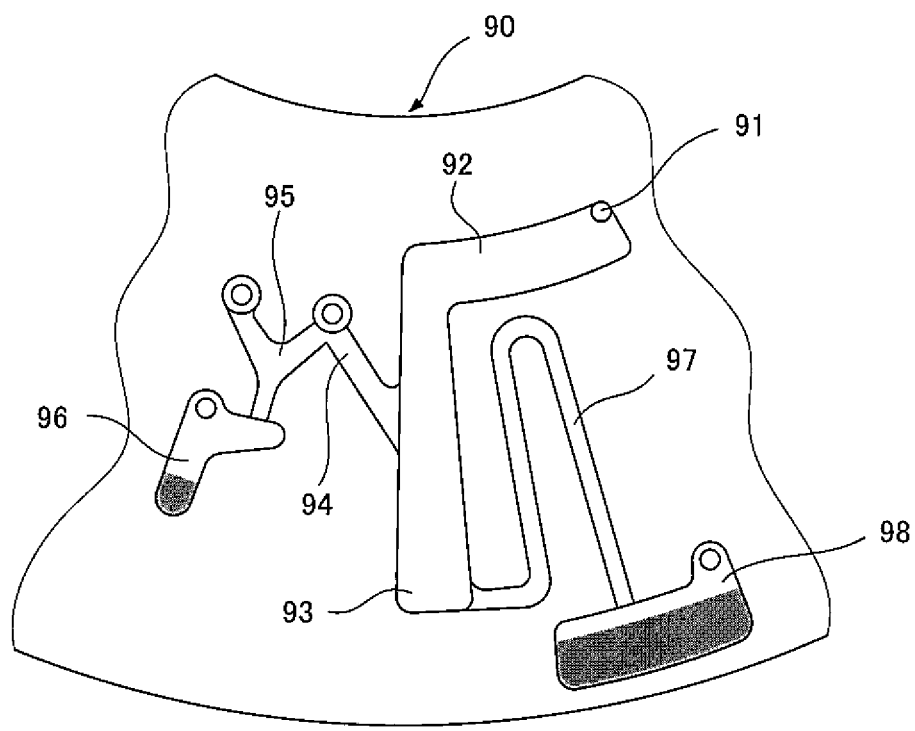
FIG. 57 is a structural diagram of Patent Literature 1.
Figure 58:
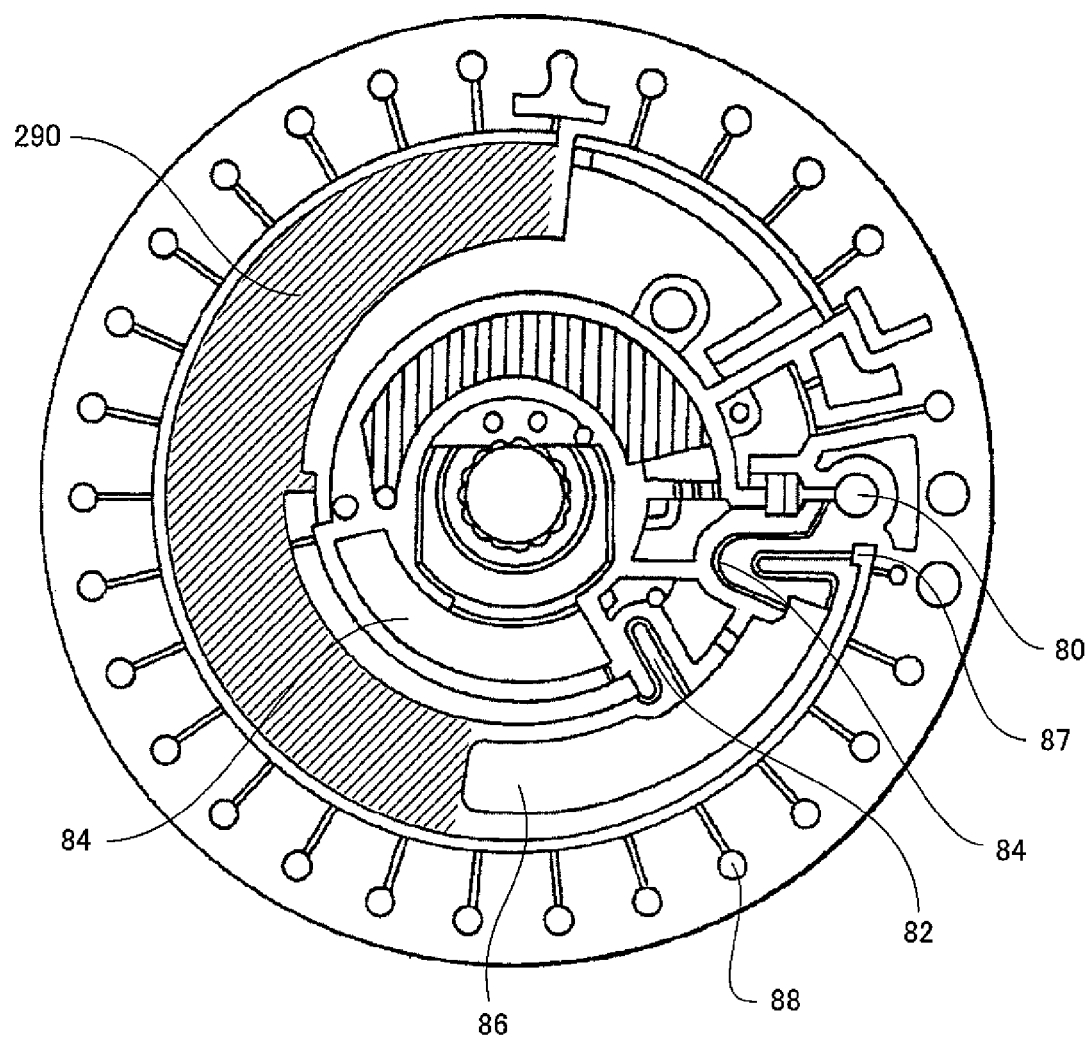
FIG. 58 is a structural diagram of Patent Literature 2.

In the tenth embodiment, a base substrate 3 and a cover substrate 4 are joined to each other as in the ninth embodiment. FIGS. 55 and 56 show the base substrate 3 of the tenth embodiment.

In the analyzing device, blood dropped as a sample liquid to a blood dropping section 262 is diluted with a diluent set in a diluent reservoir 263 and is transferred to measuring sections 264, 265, 266, 267, 268, and 269, and light 260 passing through the measuring sections 264 to 269 from a light source 259 is properly read by a photodetector 261 and is analyzed.

The blood dropped to the blood dropping section 262 is sucked into a blood retaining section 271 through a microchannel 270 formed between the base substrate 3 and the cover substrate 4. In this state, the analyzing device is rotationally driven about a rotation axis, so that the blood is metered in a blood metering chamber 273 through a blood separating section 272. Excessive blood is collected to a blood discharging section 274. The diluent is metered in a diluent metering chamber 275. An excessive diluent is collected to a discharging section 277 through a mixing section 276.

The blood metered in the blood metering chamber 273 and the diluent metered in the diluent metering chamber 275 are mixed in the mixing section 276 and are transferred to a liquid storage chamber 241.

The diluted blood transferred as the sample liquid to the liquid storage chamber 241 is metered in diluted blood metering chambers 278, 279, 280, and 281 in which a capillary force is applied.

The analyzing device is rotated again, so that the diluted blood metered in the diluted blood metering chambers 278 to 281 is transferred to the measuring sections 264 to 267. The diluted blood metered in the liquid storage chamber 241, in which a capillary force is applied, is transferred to the first reserving cavity 243 through a communicating passage 242. The diluted blood of the first reserving cavity 243 is sucked into the operation cavity 245 through a connecting section 255.

The operation cavity 245 contains reagents (not shown) as in the ninth embodiment. The measuring sections 264 to 266, and 268 also contain reagents.

By oscillating the analyzing device in this state, the reagents are dissolved by agitation and absorbance is measured in the rotation of the analyzing device. By rotating the analyzing device, the diluted blood in the operation cavity 245 is transferred to the second reserving cavity 247 through a connecting passage 256. The diluted blood in the second reserving cavity 247 is partially moved to the measuring section 268 and then is transferred to the measuring section 269 through a siphon-shaped passage 282, and absorbance is measured in the rotation of the analyzing device.

INDUSTRIAL APPLICABILITY

The present invention is useful for size reduction and improved performance of an analyzing device that is used for analyzing a component of a liquid collected from an organism or the like.

The invention claimed is:

1. An analyzing device having a microchannel structure for transferring a sample liquid, comprising:
   a rotation center around which the analyzing device is rotated;
   an outer periphery defining an outer contour of the analyzing device;
   a reserving cavity that measures a fixed quantity of a diluent, the reserving cavity being located at a distance from the rotation center;
   a mixing cavity located farther from the rotation center than the reserving cavity and connected to the reserving cavity via a connecting passage to receive the diluent from the reserving cavity and mix the sample liquid with the diluent;
   an overflow cavity located farther away from the rotation center than the reserving cavity and connected to the reserving cavity, wherein an excess quantity of the diluent flows from the reserving cavity into the overflow cavity;
   a chamber located farther from the rotation center than the overflow cavity, and connected to the reserving cavity via the overflow cavity, wherein the excess quantity of the diluent is transferred from the reserving cavity to the chamber via the overflow cavity when a centrifugal force is generated by a rotation of the analyzing device around the rotation center;
   a measurement spot located in a different circumferential location from the mixing cavity;
   a capillary passage that connects the mixing cavity to the measurement spot in a circumferential direction and transfers the sample liquid from the mixing cavity to the measuring spot by a capillary force; and
   a sealing overflow cavity between an atmospheric-side overflow cavity communicating with atmosphere and the chamber, the sealing overflow cavity communicating with the chamber via a first overflow passage and communicating with the atmospheric-side overflow cavity via a second overflow passage,
   wherein the portion of the capillary passage crosses the overflow cavity so that the overflow cavity is divided into two parts, with one part of the overflow cavity being closer to the rotation center than another part of the overflow cavity, the overflow cavity allowing the excess diluent to flow from the reserving cavity into the chamber over the capillary passage by the centrifugal force, wherein the measurement spot and the mixing cavity are located along the outer periphery at a generally common distance away from the rotation center, and wherein outlets of the chamber and the sealing overflow cavity are sealed from the atmosphere and a negative pressure is generated in the chamber and the sealing overflow cavity when the sample liquid is transferred from the mixing cavity through the capillary passage.

2. The analyzing device according to claim 1, wherein the measurement spot to which the sample liquid is transferred, is located closer to the rotation center than the mixing cavity.

3. The analyzing device according to claim 1, further comprising a base substrate and a cover substrate and a thickness defined between the base and cover substrates, wherein the base substrate has a raised floor in the capillary passage compared to a floor of the overflow cavity such that a thickness of the capillary passage is smaller than a thickness of the overflow cavity.

4. The analyzing device according to claim 1, wherein the reserving cavity is connected to the mixing cavity via a siphon-shaped connecting passage.

5. The analyzing device according to claim 1, wherein the portion of the capillary passage that connects the mixing cavity to the measurement spot divides the overflow cavity into the two parts.

* * * * *